(12) United States Patent
Hayashizaki et al.

(10) Patent No.: US 9,862,989 B2
(45) Date of Patent: Jan. 9, 2018

(54) NUCLEIC ACID PROBE, METHOD FOR DESIGNING NUCLEIC ACID PROBE, AND METHOD FOR DETECTING TARGET SEQUENCE

(71) Applicant: KABUSHIKI KAISHA DNAFORM, Yokohama-shi, Kanagawa (JP)

(72) Inventors: Yoshihide Hayashizaki, Tokyo (JP); Takeshi Hanami, Yokohama (JP); Takahiro Soma, Tokyo (JP); Yasumasa Kimura, Yokohama (JP); Hajime Kanamori, Yokohama (JP); Yasumasa Mitani, Yokohama (JP)

(73) Assignee: KABUSHIKI KAISHA DNAFORM, Kanagawa (JP)

( * ) Notice: Subject to any disclaimer, the term of this patent is extended or adjusted under 35 U.S.C. 154(b) by 44 days.

(21) Appl. No.: 14/414,806

(22) PCT Filed: Jul. 12, 2013

(86) PCT No.: PCT/JP2013/069213
§ 371 (c)(1),
(2) Date: Jan. 14, 2015

(87) PCT Pub. No.: WO2014/013954
PCT Pub. Date: Jan. 23, 2014

(65) Prior Publication Data
US 2015/0203902 A1 Jul. 23, 2015

(30) Foreign Application Priority Data

Jul. 16, 2012 (JP) .................... 2012-158229

(51) Int. Cl.
*C07H 21/04* (2006.01)
*C12Q 1/68* (2006.01)

(52) U.S. Cl.
CPC ......... *C12Q 1/6818* (2013.01); *C12Q 1/6827* (2013.01); *C12N 2330/30* (2013.01)

(58) Field of Classification Search
None
See application file for complete search history.

(56) References Cited

U.S. PATENT DOCUMENTS

| 2008/0227104 A1 | 9/2008 | Hayashizaki et al. |
| 2010/0092971 A1 | 4/2010 | Okamoto et al. |
| 2011/0151459 A1 | 6/2011 | Rothmann et al. |

FOREIGN PATENT DOCUMENTS

| EP | 0 639 647 | 2/1995 |
| JP | 7-023800 | 1/1995 |
| JP | 2009-171935 | 8/2009 |
| JP | 4370385 B2 | 11/2009 |
| JP | 2011-519570 | 7/2011 |
| JP | 4761086 B2 | 8/2011 |
| WO | 00/29613 | 5/2000 |
| WO | 02/29085 | 4/2002 |
| WO | 2008/111485 | 9/2008 |
| WO | 2 660 246 | 11/2013 |

OTHER PUBLICATIONS

Custom Synthesis Service of Novel Fluorescent Hybridazation Probe (Exciton Probe), [online] Issued by Kabushiki Kaisha DNAFORM, Mar. 22, 2012 [retrieval date: Aug. 12, 2013] Internet <URL:http://dnaform.jp/pdf/ExcitonProbe.pdf>—English Translation only.
Okamoto, "Live cell imaging of mRNA by chemically designed fluorescent nucleic acids", Experimental Medicine, vol. 26, No. 17 (extra issue), pp. 2850-2856, 2008—English Translation only.
Tyagi et al., "Molecular Beacons: Probes that Fluoresce upon Hybridization", Nat. Biotechnol., vol. 14, pp. 303-308, 1996.
Nazarenko et al., "A closed tube format for amplification and detection of DNA based on energy transfer", Nucleic Acids Res., vol. 25, No. 12, pp. 2516-2521, 1997.
Gelmini et al., "Quantitative polymerase chain reaction-based homogeneous assay with fluorogenic probes to measure c-erbB-2 oncogene amplification", Clin. Chem., vol. 43, No. 5, pp. 752-758, 1997.
Whitcombe et al., "Detection of PCR products using self-probing amplicons and fluorescence", Nat. Biotechnol., vol. 17, pp. 804-807, 1999.
Sambrook et al., "Molecular cloning : A laboratory manual", Protocol 15 Quantative PCR, p. 8.86, Cold Spring Harbor Laboratory Press, 2nd edition, 1989.
Rye et al., "High-sensitivity two-color detection of double-stranded DNA with a confocal fluorescence gel scanner using ethidium homodimer and thiazole orange", Nucleic Acids Res., vol. 19, No. 2, pp. 327-333, 1991.
Lee et al., "Thiazole Orange: A New Dye for Reticulocyte Analysis", Cytometry, vol. 7, pp. 508-517, 1986.
Svanvik et al., "Light-Up Probes: Thiazole Orange-Conjugated Peptide Nucleic Acid for Detection of Target Nucleic Acid in Homogeneous Solution", Analytical Biochemistry, vol. 281, pp. 26-35, 2000.
Hrdlicka et al., "Multilabeled Pyrene-Functionalized 2'-Amino-LNA Probes for Nucleic Acid Detection in Homogeneous Fluorescence Assays", J. Am.Chem. Soc., vol. 127, pp. 13293-13299, 2005 (with Supporting Information).

(Continued)

*Primary Examiner* — James Martinell
(74) *Attorney, Agent, or Firm* — Hamre, Schumann, Mueller & Larson, P.C.

(57) ABSTRACT

The present invention provides a nucleic acid probe that can achieve high detection sensitivity and high specificity in mutation detection, mismatch detection, etc. by the PCR method, a method for designing such a nucleic acid probe, and a method for detecting a target sequence. The nucleic acid probe includes a nucleic acid molecule, and the nucleic acid molecule includes a plurality of fluorescent dye moieties that exhibit an excitonic effect. At least two of the fluorescent dye moieties that exhibit an excitonic effect are bound to the same base or two adjacent bases in the nucleic acid molecule with each fluorescent dye moiety being bound via a linker (a linking atom or a linking atomic group). The extension-side end of the nucleic acid molecule is chemically modified, thereby preventing an extension reaction of the nucleic acid molecule.

30 Claims, 11 Drawing Sheets

(56) References Cited

OTHER PUBLICATIONS

Ashwell et al., "The synthesis and antiviral properties of (E)-5-(2-bromovinyl)-2'-deoxyuridine-related compounds", Tetrahedron, vol. 43, Iss. 20, pp. 4601-4608, 1987.

Carreon et al., "Thiazole Orange-Peptide Conjugates: Sensitivity of DNA Binding to Chemical Structure", Organic Letters, vol. 6, Iss. 4, pp. 517-519, 2004 (with Supporting Information).

Cradic et al., "Substitution of 3'-Phosphate Cap with a Carbon-Based Blocker Reduces the Possibility of Fluorescence Resonance Energy Transfer Probe Failure in Real-Time PCR Assays", Clinical Chemistry, vol. 50, No. 6, pp. 1080-1082, 2004.

2008 Price List, [online] issued by Eurogentec, p. 18, 2008 [retrieval date: Aug. 12, 2013] Internet <URL: http://www.eurogentec.Com/EGT/files/Glen-Research/GLENRES-PRICELIST.pdf>.

Okamoto, "ECHO probes: a concept of fluorescence control for practical nucleic acid sensing", Chem. Soc. Rev., vol. 40, pp. 5815-5828, 2011.

Ikeda et al., "Sequence Dependence of Fluorescence Emission and Quenching of Doubly Thiazole Orange Labeled DNA: Effective Design of a Hybridization-Sensitive Probe", Bioconjugate Chemistry, vol. 19, No. 8, pp. 1719-1725, 2008.

Sugizaki et al., "ECHO-LNA Conjugates: Hybridization-Sensitive Fluorescence and its Application toFluorescent Detection of Various RNA Strands", Bioconjugate Chemistry, vol. 21, No. 12, pp. 2276-2281 (2010).

Lezhava et al., "Exciton Primer-Mediated SNP Detection in SmartAmp2 Reactions", Human Mutation, vol. 31, No. 2, pp. 208-217 (2010).

Ikeda et al., "Exciton-Controlled Hybridization-Sensitive Fluorescent Probes: Multicolor Detection ofNucleic Acids", Angewandte Chemie, vol. 48, No. 35, pp. 6480-6484 (2009).

Kimura et al., "Effect of Thiazole Orange Doubly Labeled Thymidine on DNA Duplex Formation", Biochemistry, vol. 51, No. 31, pp. 6056-6067 (2012).

Hanami et al., "Eprobe Mediated Real-Time PCR Monitoring and Melting Curve Analysis", PLOSONE, vol. 8, No. 8, E70942, pp. 1-12 (2013).

Okamoto et al., "A nucleic acid probe labeled with desmethyl thiazole orange: a new type ofhybridization-sensitive fluorescent oligonucleotide for live-cell RNA imaging", Organic &Biomolecular Chemistry, vol. 11, No. 2, pp. 362-371 (2013).

Extended European Search Report in the corresponding European Patent Application No. 13820349.2, dated Mar. 29, 2016, 14 pages.

Office Action issued in corresponding European Patent Application No. 13820349.2, dated Feb. 20, 2017, 5 pages.

SEQUENCE LISTING

<160> NUMBER OF SEQ ID NOS: 47

<210> SEQ ID NO 1
<211> LENGTH: 20
<212> TYPE: DNA
<213> ORGANISM: Artificial Sequence -continued

```
<220> FEATURE:
<223> OTHER INFORMATION: primer

<400> SEQUENCE: 1
cctcacagca gggtcttctc                                              20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
cctggtgtca ggaaaatgct                                              20

<210> SEQ ID NO 3
<211> LENGTH: 300
<212> TYPE: DNA
<213> ORGANISM: Artificial Sequence
<220> FEATURE:
<223> OTHER INFORMATION: plasmid DNA

<400> SEQUENCE: 3
tgaacatgac cctgaattcg gatgcagagc ttcttcccat gatgatctgt ccctcacagc   60
agggtcttct ctgtttcagg gcatgaacta cttggaggac gtcgcttgg tgcaccgcga   120 cctggcagcc aggaacgtac tggtgaaaac accgcagcat gtcaagatca cagattttgg   180
gctggccaaa ctgctgggtg cggaagagaa agaataccat gcagaaggag gcaaagtaag   240
gaggtggctt taggtcagcc agcatttttcc tgacaccagg gaccaggctg ccttcccact   300

<210> SEQ ID NO 4
<211> LENGTH: 350
<212> TYPE: DNA
<213> ORGANISM: Artificial Sequence
<220> FEATURE:
<223> OTHER INFORMATION: L858R mutant

<400> SEQUENCE: 4
agcctggcat gaacatgacc ctgaattcgg atgcagagct tcttcccatg atgatctgtc   60
cctcacagca gggtcttctc tgtttcaggg catgaactac ttggaggacc gtcgcttggt   120
gcaccgcgac ctggcagcca ggaacgtact ggtgaaaaca ccgcagcatg tcaagatcac   180
agattttggg cgggccaaac tgctgggtgc ggaagagaaa gaataccatg cagaaggagg   240
caaagtaagg aggtggcttt aggtcagcca gcattttcct gacaccaggg accaggctgc   300
cttcccacta gctgtattgt ttaacacatg caggggagga tgctctccag              350

<210> SEQ ID NO 5
<211> LENGTH: 22
<212> TYPE: DNA
<213> ORGANISM: Artificial Sequence
<220> FEATURE:
<223> OTHER INFORMATION: E probe
<220> FEATURE:
<221> NAME/KEY: misc_feature
<222> LOCATION: (12)..(12)
<223> OTHER INFORMATION: n represents thymine introduced dye label
      having exciton effect

<400> SEQUENCE: 5
agattttggg cnggccaaac tg                                           22
```

```
<210> SEQ ID NO 6
<211> LENGTH: 20
<212> TYPE: DNA
<213> ORGANISM: Artificial Sequence
<220> FEATURE:
<223> OTHER INFORMATION: E probe
<220> FEATURE:
<221> NAME/KEY: misc_feature
<222> LOCATION: (1)..(1)
<223> OTHER INFORMATION: n represents thymine introduced dye label
      having exciton effect

<400> SEQUENCE: 6
ngtgtatctt tctctttctc                                                   20

<210> SEQ ID NO 7
<211> LENGTH: 20
<212> TYPE: DNA
<213> ORGANISM: Artificial Sequence
<220> FEATURE:
<223> OTHER INFORMATION: E probe
<220> FEATURE:
<221> NAME/KEY: misc_feature
<222> LOCATION: (3)..(3)
<223> OTHER INFORMATION: n represents thymine introduced dye label
      having exciton effect

<400> SEQUENCE: 7
tgngtatctt tctctttctc                                                   20

<210> SEQ ID NO 8
<211> LENGTH: 20
<212> TYPE: DNA
<213> ORGANISM: Artificial Sequence
<220> FEATURE:
<223> OTHER INFORMATION: E probe
<220> FEATURE:
<221> NAME/KEY: misc_feature
<222> LOCATION: (5)..(5)
<223> OTHER INFORMATION: n represents thymine introduced dye label
      having exciton effect

<400> SEQUENCE: 8
tgtgnatctt tctctttctc                                                   20

<210> SEQ ID NO 9
<211> LENGTH: 20
<212> TYPE: DNA
<213> ORGANISM: Artificial Sequence
<220> FEATURE:
<223> OTHER INFORMATION: E probe
<220> FEATURE:
<221> NAME/KEY: misc_feature
<222> LOCATION: (7)..(7)
<223> OTHER INFORMATION: n represents thymine introduced dye label
      having exciton effect

<400> SEQUENCE: 9
tgtgtanctt tctctttctc                                                   20

<210> SEQ ID NO 10
<211> LENGTH: 20
<212> TYPE: DNA
<213> ORGANISM: Artificial Sequence
<220> FEATURE:
<223> OTHER INFORMATION: E probe
<220> FEATURE:
<221> NAME/KEY: misc_feature
<222> LOCATION: (9)..(9)
<223> OTHER INFORMATION: n represents thymine introduced dye label
      having exciton effect
```

<400> SEQUENCE: 10
tgtgtatcnt tctctttctc                                           20

<210> SEQ ID NO 11
<211> LENGTH: 20
<212> TYPE: DNA
<213> ORGANISM: Artificial Sequence
<220> FEATURE:
<223> OTHER INFORMATION: E probe
<220> FEATURE:
<221> NAME/KEY: misc_feature
<222> LOCATION: (11)..(11)
<223> OTHER INFORMATION: n represents thymine introduced dye label
      having exciton effect

<400> SEQUENCE: 11
tgtgtatctt nctctttctc                                           20

<210> SEQ ID NO 12
<211> LENGTH: 20
<212> TYPE: DNA
<213> ORGANISM: Artificial Sequence
<220> FEATURE:
<223> OTHER INFORMATION: E probe
<220> FEATURE:
<221> NAME/KEY: misc_feature
<222> LOCATION: (13)..(13)
<223> OTHER INFORMATION: n represents thymine introduced dye label
      having exciton effect

<400> SEQUENCE: 12
tgtgtatctt tcnctttctc                                           20

<210> SEQ ID NO 13
<211> LENGTH: 20
<212> TYPE: DNA
<213> ORGANISM: Artificial Sequence
<220> FEATURE:
<223> OTHER INFORMATION: E probe
<220> FEATURE:
<221> NAME/KEY: misc_feature
<222> LOCATION: (15)..(15)
<223> OTHER INFORMATION: n represents thymine introduced dye label
      having exciton effect

<400> SEQUENCE: 13
tgtgtatctt tctcnttctc                                           20

<210> SEQ ID NO 14
<211> LENGTH: 20
<212> TYPE: DNA
<213> ORGANISM: Artificial Sequence
<220> FEATURE:
<223> OTHER INFORMATION: E probe
<220> FEATURE:
<221> NAME/KEY: misc_feature
<222> LOCATION: (17)..(17)
<223> OTHER INFORMATION: n represents thymine introduced dye label
      having exciton effect

<400> SEQUENCE: 14
tgtgtatctt tctcttnctc                                           20

<210> SEQ ID NO 15
<211> LENGTH: 20
<212> TYPE: DNA
<213> ORGANISM: Artificial Sequence
<220> FEATURE:
<223> OTHER INFORMATION: E probe

```
<220> FEATURE:
<221> NAME/KEY: misc_feature
<222> LOCATION: (19)..(19)
<223> OTHER INFORMATION: n represents thymine introduced dye label
      having exciton effect

<400> SEQUENCE: 15
tgtgtatctt tctctttcnc                                                   20

<210> SEQ ID NO 16
<211> LENGTH: 20
<212> TYPE: DNA
<213> ORGANISM: Artificial Sequence
<220> FEATURE:
<223> OTHER INFORMATION: complementary sequence

<400> SEQUENCE: 16
gagaaagaga aagatacaca                                                   20

<210> SEQ ID NO 17
<211> LENGTH: 20
<212> TYPE: DNA
<213> ORGANISM: Artificial Sequence
<220> FEATURE:
<223> OTHER INFORMATION: complementary sequence

<400> SEQUENCE: 17
gagcaagaga aagatacaca                                                   20

<210> SEQ ID NO 18
<211> LENGTH: 20
<212> TYPE: DNA
<213> ORGANISM: Artificial Sequence
<220> FEATURE:
<223> OTHER INFORMATION: complementary sequence

<400> SEQUENCE: 18
gaggaagaga aagatacaca                                                   20

<210> SEQ ID NO 19
<211> LENGTH: 20
<212> TYPE: DNA
<213> ORGANISM: Artificial Sequence
<220> FEATURE:
<223> OTHER INFORMATION: complementary sequence

<400> SEQUENCE: 19
gagtaagaga aagatacaca                                                   20

<210> SEQ ID NO 20
<211> LENGTH: 20
<212> TYPE: DNA
<213> ORGANISM: Artificial Sequence
<220> FEATURE:
<223> OTHER INFORMATION: complementary sequence

<400> SEQUENCE: 20
gagaaagaaa aagatacaca                                                   20

<210> SEQ ID NO 21
<211> LENGTH: 20
<212> TYPE: DNA
<213> ORGANISM: Artificial Sequence
<220> FEATURE:
<223> OTHER INFORMATION: complementary sequence
```

```
<400> SEQUENCE: 21
gagaaagaca aagatacaca                                          20

<210> SEQ ID NO 22
<211> LENGTH: 20
<212> TYPE: DNA
<213> ORGANISM: Artificial Sequence
<220> FEATURE:
<223> OTHER INFORMATION: complementary sequence

<400> SEQUENCE: 22
gagaaagata aagatacaca                                          20

<210> SEQ ID NO 23
<211> LENGTH: 20
<212> TYPE: DNA
<213> ORGANISM: Artificial Sequence
<220> FEATURE:
<223> OTHER INFORMATION: complementary sequence

<400> SEQUENCE: 23
gagaaagagc aagatacaca                                          20

<210> SEQ ID NO 24
<211> LENGTH: 20
<212> TYPE: DNA
<213> ORGANISM: Artificial Sequence
<220> FEATURE:
<223> OTHER INFORMATION: complementary sequence

<400> SEQUENCE: 24
gagaaagagg aagatacaca                                          20

<210> SEQ ID NO 25
<211> LENGTH: 20
<212> TYPE: DNA
<213> ORGANISM: Artificial Sequence
<220> FEATURE:
<223> OTHER INFORMATION: complementary sequence

<400> SEQUENCE: 25
gagaaagagt aagatacaca                                          20

<210> SEQ ID NO 26
<211> LENGTH: 20
<212> TYPE: DNA
<213> ORGANISM: Artificial Sequence
<220> FEATURE:
<223> OTHER INFORMATION: complementary sequence

<400> SEQUENCE: 26
gagaaagaga cagatacaca                                          20

<210> SEQ ID NO 27
<211> LENGTH: 20
<212> TYPE: DNA
<213> ORGANISM: Artificial Sequence
<220> FEATURE:
<223> OTHER INFORMATION: complementary sequence

<400> SEQUENCE: 27
gagaaagaga gagatacaca                                          20
```

```
<210> SEQ ID NO 28
<211> LENGTH: 20
<212> TYPE: DNA
<213> ORGANISM: Artificial Sequence
<220> FEATURE:
<223> OTHER INFORMATION: complementary sequence

<400> SEQUENCE: 28
gagaaagaga tagatacaca                                          20

<210> SEQ ID NO 29
<211> LENGTH: 20
<212> TYPE: DNA
<213> ORGANISM: Artificial Sequence
<220> FEATURE:
<223> OTHER INFORMATION: complementary sequence

<400> SEQUENCE: 29
gagaaagaga aagatccaca                                          20

<210> SEQ ID NO 30
<211> LENGTH: 20
<212> TYPE: DNA
<213> ORGANISM: Artificial Sequence
<220> FEATURE:
<223> OTHER INFORMATION: complementary sequence

<400> SEQUENCE: 30
gagaaagaga aagatgcaca                                          20

<210> SEQ ID NO 31
<211> LENGTH: 20
<212> TYPE: DNA
<213> ORGANISM: Artificial Sequence
<220> FEATURE:
<223> OTHER INFORMATION: complementary sequence

<400> SEQUENCE: 31
gagaaagaga aagattcaca                                          20

<210> SEQ ID NO 32
<211> LENGTH: 27
<212> TYPE: DNA
<213> ORGANISM: Artificial Sequence
<220> FEATURE:
<223> OTHER INFORMATION: primer

<400> SEQUENCE: 32
ttataaggcc tgctgaaaat gactgaa                                  27

<210> SEQ ID NO 33
<211> LENGTH: 26
<212> TYPE: DNA
<213> ORGANISM: Artificial Sequence
<220> FEATURE:
<223> OTHER INFORMATION: primer

<400> SEQUENCE: 33
tgaattagct gtatcgtcaa ggcact                                   26

<210> SEQ ID NO 34
<211> LENGTH: 839
<212> TYPE: DNA
<213> ORGANISM: Artificial Sequence
<220> FEATURE:
<223> OTHER INFORMATION: Plasmid DNA
```

<400> SEQUENCE: 34

```
caaacttaca ggggctcgac gagctaggtt cccggacacg acaaaggcgg ccgcgggaat    60
tgcgttggag gagtttgtaa ataaagtaca gttcattacg atacacgtct gcagtcaact   120
ggaattttca tgattgaatt ttgtaaggta ttttgaaata attttcata taaaggtgag    180
tttgtattaa aaggtactgg tggagtattt gatagtgtat taaccttatg tgtgacatgt   240
tctaatatag tcacattttc attatttta ttataaggcc tgctgaaaat gactgaatat    300
aaacttgtgg tagttggagc tggtggcgta ggcaagagtg ccttgacgat acagctaatt   360
cagaatcatt ttgtggacga atatgatcca acaatagagg taaatcttgt tttaatatgc   420
atattactgg tgcaggacca ttctttgata cagataaagg tttctctgac cattttcatg   480
agtacttatt acaagataat tatgctgaaa gttaagttat ctgaaatgta ccttgggttt   540
caagttatat gtaaccatta atatgggaac tttactttcc ttgggagtat gaatcactag   600
tgaattcgcg gccgcctgca ggtcgaccat atgggagagc tccaacgcgt tggatgcata   660
gcttgagtat tctatagtgt cacctaaata gcttggcgta atcatggtca tagctgtttc   720
ctgtgtgaaa ttgttatccg ctcacatttc cacacacata cgagccggaa gcataaagtg   780
taaagcctgg ggtgctcaat gagtgagcta actcacatta ttgcgttgcg ctcactgcc    839
```

<210> SEQ ID NO 35
<211> LENGTH: 716
<212> TYPE: DNA
<213> ORGANISM: Artificial Sequence
<220> FEATURE:
<223> OTHER INFORMATION: G12D mutant

<400> SEQUENCE: 35

```
tacctctagg gacgccgaat cacgcggtat cccggccgcc atagagacgg ccgcgggaat    60
tcgattggag gagtttgtaa ataaagtaca gttcattacg atacacgtct gcagtcaact   120
ggaattttca tgattgaatt ttgtaaggta ttttgaaata attttcata taaaggtgag    180
tttgtattaa aaggtactgg tggagtattt gatagtgtat taaccttatg tgtgacatgt   240
tctaatatag tcacattttc attatttta ttataaggcc tgctgaaaat gactgaatat    300
aaacttgtgg tagttggagc tgatggcgta ggcaagagtg ccttgacgat acagctaatt   360
cagaatcatt ttgtggacga atatgatcca acaatagagg taaatcttgt tttaatatgc   420
atattactgg tgcaggacca ttctttgata cagataaagg tttctctgac cattttcatg   480
agtacttatt acaagataat tatgctgaaa gttaagttat ctgaaatgta ccttgggttt   540
caagttatat gtaaccatta atatgggaac tttactttcc ttgggagtat gaatcactag   600
tgaattcgcg gccgcctgca ggtcgaccat atgggagagc tcccaacgcg ttggatgcat   660
agcttgagta ttctatagtg tcacctaaat agcttgggcg taatcatggt catagc       716
```

<210> SEQ ID NO 36
<211> LENGTH: 14
<212> TYPE: DNA
<213> ORGANISM: Artificial Sequence
<220> FEATURE:
<223> OTHER INFORMATION: E probe
<220> FEATURE:
<221> NAME/KEY: misc_feature
<222> LOCATION: (12)..(12)
<223> OTHER INFORMATION: n represents thymine introduced dye label
      having exciton effect

```
<400> SEQUENCE: 36
agctggtggc gnag                                                         14

<210> SEQ ID NO 37
<211> LENGTH: 14
<212> TYPE: DNA
<213> ORGANISM: Artificial Sequence
<220> FEATURE:
<223> OTHER INFORMATION: E probe
<220> FEATURE:
<221> NAME/KEY: misc_feature
<222> LOCATION: (7)..(7)
<223> OTHER INFORMATION: n represents thymine introduced dye label
      having exciton effect

<400> SEQUENCE: 37
agctggnggc gtag                                                         14

<210> SEQ ID NO 38
<211> LENGTH: 14
<212> TYPE: DNA
<213> ORGANISM: Artificial Sequence
<220> FEATURE:
<223> OTHER INFORMATION: E probe
<220> FEATURE:
<221> NAME/KEY: misc_feature
<222> LOCATION: (12)..(12)
<223> OTHER INFORMATION: n represents thymine introduced dye label
      having exciton effect

<400> SEQUENCE: 38
agctggtggc gnag                                                         14

<210> SEQ ID NO 39
<211> LENGTH: 14
<212> TYPE: DNA
<213> ORGANISM: Artificial Sequence
<220> FEATURE:
<223> OTHER INFORMATION: E probe
<220> FEATURE:
<221> NAME/KEY: misc_feature
<222> LOCATION: (7)..(7)
<223> OTHER INFORMATION: n represents thymine introduced dye label
      having exciton effect

<400> SEQUENCE: 39
agctggnggc gtag                                                         14

<210> SEQ ID NO 40
<211> LENGTH: 14
<212> TYPE: DNA
<213> ORGANISM: Artificial Sequence
<220> FEATURE:
<223> OTHER INFORMATION: E probe
<220> FEATURE:
<221> NAME/KEY: misc_feature
<222> LOCATION: (3)..(3)
<223> OTHER INFORMATION: n represents thymine introduced dye label
      having exciton effect

<400> SEQUENCE: 40
gtnggagctg gtgg                                                         14

<210> SEQ ID NO 41
<211> LENGTH: 22
<212> TYPE: DNA
<213> ORGANISM: Artificial Sequence
<220> FEATURE:
<223> OTHER INFORMATION: E probe
```

```
<220> FEATURE:
<221> NAME/KEY: misc_feature
<222> LOCATION: (16)..(16)
<223> OTHER INFORMATION: n represents thymine introduced dye label
      having exciton effect

<400> SEQUENCE: 41
ttggagctgg tggcgnaggc aa                                              22

<210> SEQ ID NO 42
<211> LENGTH: 19
<212> TYPE: DNA
<213> ORGANISM: Artificial Sequence
<220> FEATURE:
<223> OTHER INFORMATION: E probe
<220> FEATURE:
<221> NAME/KEY: misc_feature
<222> LOCATION: (4)..(4)
<223> OTHER INFORMATION: n represents thymine introduced dye label
      having exciton effect

<400> SEQUENCE: 42
ctcntgccta cgccaccag                                                  19

<210> SEQ ID NO 43
<211> LENGTH: 13
<212> TYPE: DNA
<213> ORGANISM: Artificial Sequence
<220> FEATURE:
<223> OTHER INFORMATION: E probe
<220> FEATURE:
<221> NAME/KEY: misc_feature
<222> LOCATION: (8)..(8)
<223> OTHER INFORMATION: n represents thymine introduced dye label
      having exciton effect

<400> SEQUENCE: 43
tcttgganca acc                                                        13

<210> SEQ ID NO 44
<211> LENGTH: 48
<212> TYPE: DNA
<213> ORGANISM: Artificial Sequence
<220> FEATURE:
<223> OTHER INFORMATION: Sense DNA

<400> SEQUENCE: 44
acgaccgggt cctttcttgg atcaacccgc tcaatgcctg gagatttg                   48

<210> SEQ ID NO 45
<211> LENGTH: 48
<212> TYPE: DNA
<213> ORGANISM: Artificial Sequence
<220> FEATURE:
<223> OTHER INFORMATION: Anti-Sense DNA

<400> SEQUENCE: 45
caaatctcca ggcattgagc gggttgatcc aagaaaggac ccggtcgt                   48

<210> SEQ ID NO 46
<211> LENGTH: 25
<212> TYPE: DNA
<213> ORGANISM: Artificial Sequence
<220> FEATURE:
<223> OTHER INFORMATION: E probe
```

```
<220> FEATURE:
<221> NAME/KEY: misc_feature
<222> LOCATION: (3)..(3)
<223> OTHER INFORMATION: n represents thymine introduced dye label
      having exciton effect

<400> SEQUENCE: 46
ttncctaccc acttttctcc cattt                                           25

<210> SEQ ID NO 47
<211> LENGTH: 15
<212> TYPE: DNA
<213> ORGANISM: Artificial Sequence
<220> FEATURE:
<223> OTHER INFORMATION: template nucleic acid

<400> SEQUENCE: 47
aaatgggaga aaagt                                                      15
```

NUCLEIC ACID PROBE, METHOD FOR DESIGNING NUCLEIC ACID PROBE, AND METHOD FOR DETECTING TARGET SEQUENCE

TECHNICAL FIELD

The present invention relates to a nucleic acid probe, a method for designing a nucleic acid probe, and a method for detecting a target sequence.

BACKGROUND ART

In biological phenomenon analysis at a cellular level and diagnosis of a disease at a molecular level, it is necessary to detect a specific protein or a specific nucleic acid sequence, and fluorescence is used widely for the detection. Specifically, a method is known that uses a fluorescent substance whose fluorescence intensity increases in response to binding to a target protein and an increase of a target nucleic acid sequence. Representative examples of the fluorescent substance include a method utilizing Foerster resonance energy transfer (FRET) and a substance that intercalates into a double helix structure and emits fluorescence by irradiation with excitation light.

However, there is a possibility that a conventional fluorescent substance emits fluorescence even when it is not bound to a target substance, for example. For the purpose of quenching fluorescence of only an antibody or a nucleic acid sequence labeled with a fluorescent substance, the method utilizing FRET is effective (e.g., Non-Patent Documents 1 to 4). However, making use of FRET requires, for example, the introduction of two types of fluorescent dyes and a unique sequence and the precise design of the position to which each fluorescent dye is bound, which poses the problems of, for example, sequence restriction and manufacturing cost.

Hence, for solving the aforementioned problems, fluorescence detection systems using only one type of dye have been proposed, and the one of them is a complex labeling substance having, as a characteristic chemical structure, a chemical structure in which at least two dye molecules are contained in one molecule, with the at least two dye molecules not exhibiting fluorescence emission due to the excitonic effect obtained when they aggregate in parallel to each other, but exhibiting fluorescence emission with the aggregation state being resolved when the molecules undergo intercalation into or groove binding to nucleic acid (Patent Document 1). Use of the labeling substance of this type as a primer or a probe (e.g. exciton oligomer) obtained by introducing the labeling substance into oligonucleotide for, for example, the amplification and detection of a target nucleic acid is disclosed (Patent Document 2). Note here that, hereinafter, the probe may be referred to as the "exciton probe" or the Eprobe". This exciton oligomer or the like allows fluorescent switching before and after hybridization with one type of dye; and in the case where the excitonic oligomer or the like is used for real-time monitoring of an amplification reaction, since it gives a sequence specific fluorescent signal, the conventional problem that non-specific amplification is also detected when SYBR green I is used can be overcome. Furthermore, since a fluorophore can be introduced into dT or dC, the restriction of sequence almost can be avoided.

CITATION LIST

Patent Document(s)

Patent Document 1: Japanese Patent No. 4761086
Patent Document 2: Japanese Patent No. 4370385

Non-Patent Document(s)

Non-Patent Document 1: Tyagi, S., Kramer, F. R. (1996) Nat. Biotechnol. 14, 303-308.
Non-Patent Document 2: Nazarenko, I. A., Bhatnagar, S. K., Hohman, R. J. (1997) Nucleic Acids Res. 25, 2516-2521.
Non-Patent Document 3: Gelmini, S., Orlando, C., Sestini, R., Vona, G., Pinzani, P., Ruocco, L., Pazzagli, M. (1997) Clin. Chem. 43, 752-758.
Non-Patent Document 4: Whitcombe, D., Theaker, J., Guy, S. P., Brown, T., Little, S. (1999) Nat. Biotechnol. 17, 804-807.

BRIEF SUMMARY OF THE INVENTION

Problem to be Solved by the Invention

However, for example, for confirming an amplification product of PCR using an exciton probe (Eprobe), there is a need for preliminarily adding the probe (Eprobe) that does not cause an extension reaction from the 3' end to an amplification reagent and performing detection of a single nucleotide polymorphism (SNP) or a mutation(s) by monitoring PCR reaction in real time or drawing a melting curve after amplification. Thus, optimization of, for example, the PCR reaction condition and design method such as the positional relationship between an exciton-labeled site of such a probe and a target SNP site is needed.

As in the case of a cancer sample, when mutation occurs gradually in chronological order as the disease condition progresses, a certain amount of normal-type template DNA and a small amount of mutant-type DNA coexist. In the detection of such mutation, the improvement of detection sensitivity has been achieved by suppressing the amplification of normal-type DNA sequences that are present in large numbers while amplifying mutant-type DNA sequences intensively. On this occasion, a clumping probe has been used separately from a detection probe for suppressing the amplification of the normal-type DNA sequences. For example, in the case where a TaqMan (registered trademark) probe is used as a detection probe, PNA that strongly forms a complementary strand with DNA is used as the clumping probe. Accordingly, in such a case, two types of probes are required. Therefore, an amplification region needs a region to which these two types of probes hybridize, and this naturally results in the restriction on the amplification length and design region.

It is known that the Eprobe strongly interacts with DNA like PNA because a dye introduced into the Eprobe is cationic. Accordingly, if use of the Eprobe that achieves full match hybridization to a normal type promotes the amplification of a mutant while suppressing the amplification of the normal type in an amplification reaction and, at the same time, allows the confirmation of the presence of the mutant in a mismatch region in melting curve analysis, this greatly contributes to the improvement in detection techniques.

With the foregoing in mind, it is an object of the present invention to provide a nucleic acid probe that can achieve high detection sensitivity and high specificity in mutation detection, mismatch detection, etc. by the PCR method, a method for designing such a nucleic acid probe, and a method for detecting a target sequence.

Means for Solving Problem

In order to achieve the above object, the present invention provides a nucleic acid probe including: a nucleic acid molecule, wherein the nucleic acid molecule includes a plurality of fluorescent dye moieties that exhibit an excitonic effect, at least two of the fluorescent dye moieties that exhibit an excitonic effect are bound to the same base or two adjacent bases in the nucleic acid molecule with each fluorescent dye moiety being bound via a linker (a linking atom or a linking atomic group), and an extension-side end of the nucleic acid molecule is chemically modified, thereby preventing an extension reaction of the nucleic acid molecule.

The present invention also provides a method for designing a nucleic acid probe for use in detection of a sequence that has a mutation (mismatch). In the method, the nucleic acid probe is the nucleic acid probe according to the present invention, and the nucleic acid probe is designed so that it satisfies the following condition (1):
(1) a labeled base to which the fluorescent dye moieties that exhibit an excitonic effect are bound is a base other than the first base at each end of the nucleic acid probe.

The present invention also provides a method for detecting a target sequence in a nucleic acid using a nucleic acid probe that hybridizes to the target sequence, wherein the nucleic acid probe is the nucleic acid probe according to the present invention.

Effects of the Invention

According to the present invention, it is possible to provide a nucleic acid probe that can achieve high detection sensitivity and high specificity in mutation detection, mismatch detection, etc. by the PCR method, a method for designing such a nucleic acid probe, and a method for detecting a target sequence.

MODE FOR CARRYING OUT THE INVENTION

Figure 1:
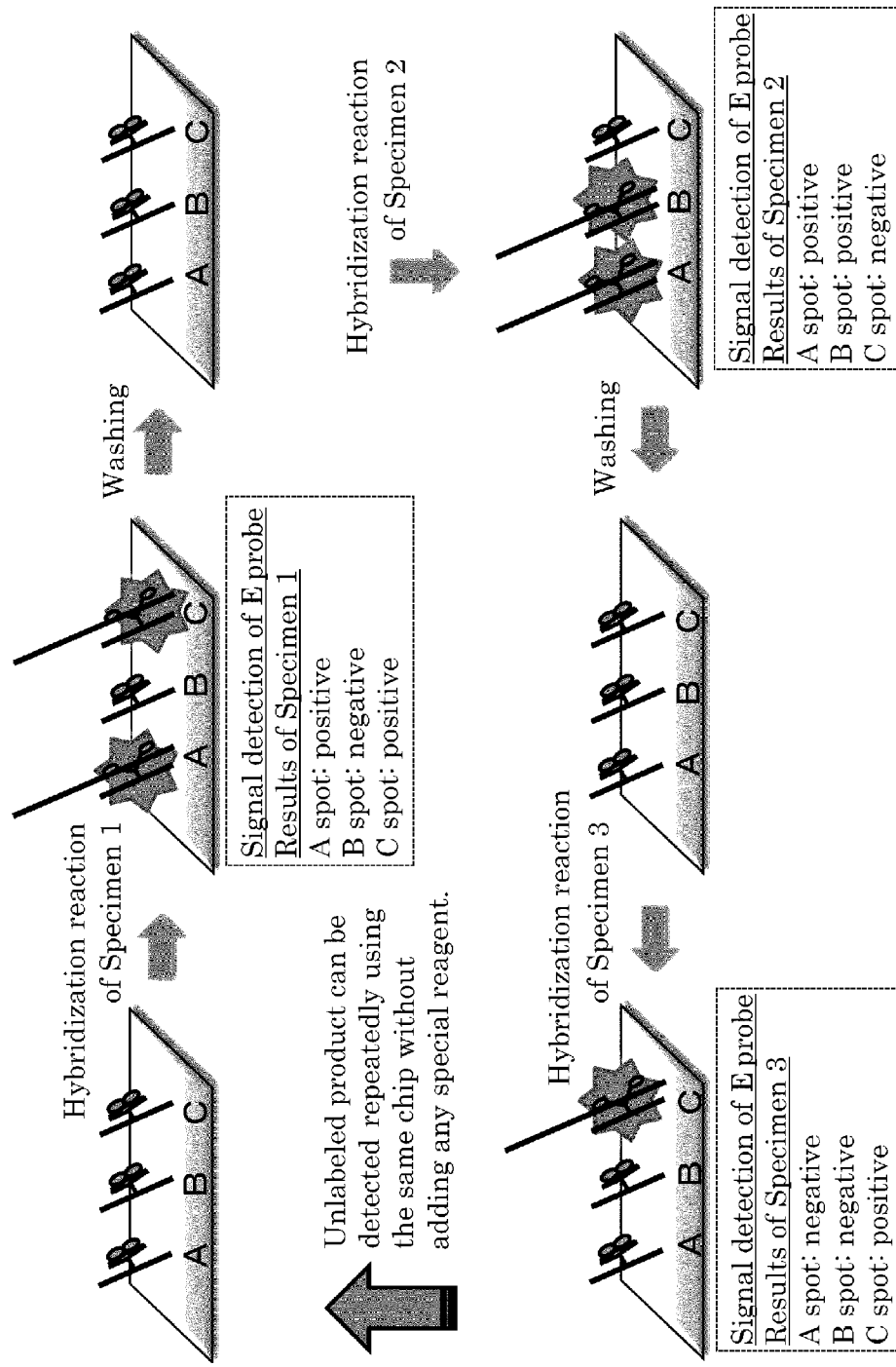
FIG. 1 is a diagram schematically showing one example of a usage pattern of the nucleic acid probe (Eprobe) of the present invention.

Hereinafter, the present invention will be described in more detail with reference to illustrative examples. However, the present invention is not limited by the following description.

[Nucleic Acid Probe]

The Eprobe is a DNA probe into which two fluorescent dye moieties (e.g. thiazole orange and its similar substance) are introduced. The Eprobe has a property of hardly emitting fluorescence due to the excitonic effect obtained when two fluorescent dye moieties form exciplex in the case of single strand but strongly emitting fluorescence with the dissociation of excitonic effect when two dye moieties move away from each other upon its hybridization to a target DNA. In the detection of a target nucleic acid by a PCR reaction, for improving the detection sensitivity by the melting curve analysis using such an Eprobe, it is necessary to overcome the problems described below.

(1) There is a possibility of an unnecessary extension reaction occuring from the 3' end of the Eprobe that has hybridized to a target nucleic acid.

(2) The stability of hybridization and the detection efficiency are greatly influenced by the exciton-labeled position in the Eprobe, the position of the corresponding mutation site (mismatch site), or the relative relationship between the aforementioned positions.

(3) There is a restriction on the probe design such that, in the case where a non-target sequence coexists in a sample, the addition of a clumping reagent that hybridizes to the non-target sequence is required for suppressing the amplification of the non-target sequence.

(4) There might be a case where the excitonic effect cannot be obtained sufficiently depending on a base sequence that forms the Eprobe.

As a result of a great deal of consideration with the aim of improving the mismatch detection sensitivity using the Eprobe, the inventors of the present invention found several elements with which various problems can be overcome, and by the application of these elements, the inventors of the present invention achieved the improvements of the detection sensitivity and specificity. Note here that while the "Eprobe" and "Eprobe" are the trade names of products of Kabushiki Kaisha DNAFORM ("Eprobe" is a registered trademark), the "Eprobe" in the present invention may be identical to or different from a product given the trade name of the "Eprobe" or the "Eprobe".

In order to solve the aforementioned problems, the inventors of the present invention developed (1) a method of hindering an unnecessary extension reaction from the 3' end of the Eprobe that has hybridized to a target nucleic acid.

They also found (2) a method of improving the stability of hybridization and the detection efficiency by designing the exciton-labeled position in the Eprobe, the position of the corresponding mutation site (mismatch site), or the relative relationship between the aforementioned positions. Furthermore, they found that (3) when a full match probe is added to a sample, the probe takes two functions of clumping and detection. Still further, they found that (4) the excitonic effect is ruined if, in the vicinity of the exciton-labeled base in the Eprobe, a sequence that can form a double strand in the molecule of the Eprobe is present.

That is, the Eprobe according to the present invention is characterized in that the 3' end thereof is chemically modified with a linker OH group. Another aspect of the present invention is a method of hindering, when an Eprobe has hybridized to a target sequence, an extension reaction from the 3' end of the Eprobe with the target sequence as a template. The method is characterized in that the 3' end of the Eprobe is chemically modified with a linker OH group.

The Eprobe according to the present invention may be designed so as to satisfy, for example, the following condition (1). Viewed from another aspect, the present invention provides, for example, a method for designing an Eprobe that satisfies the condition (1).

(1) A labeled base to which the fluorescent dye moieties that exhibit an excitonic effect are bound is a base other than the first base at each end of the nucleic acid probe (Eprobe) (the base is at least two bases inward from each end of the Eprobe), more preferably a base other than the first and second bases from each end of the Eprobe (the base is at least three bases inward from each end of the Eprobe), and still more preferably a base other than the first to third bases from each end of the Eprobe (the base is at least four bases inward from each end of the Eprobe).

The Eprobe according to the present invention may be designed so as to satisfy further, for example, the following condition (2). Viewed from another aspect, the present invention provides, for example, a method for designing an Eprobe that satisfies both the conditions (1) and (2).

(2) A target sequence to which the nucleic acid probe hybridizes is a sequence that has a mutation (mismatch), and the mismatch is a base other than the first and second bases from each end of the target sequence (a region to which the Eprobe hybridizes) (the mismatch is at least three bases inward from each end of the target sequence), more preferably a base other than the first to third bases from each end of the target sequence (the mismatch is at least four bases inward from each end of the target sequence).

The Eprobe according to the present invention may be designed so as to satisfy further, for example, the following condition (3) or the following condition (4) in addition to the condition (1) (and optionally, also the condition (2)). Specifically, when it is required to make a difference in detection peak intensity between a sequence that does not have the mutation in the target sequence (full match) and a sequence that has the mutation in the target sequence (mismatch) by the labeled position in the Eprobe, the Eprobe may be designed so as to satisfy the condition (3), and when it is required not to make the difference, the Eprobe may be designed so as to satisfy the condition (4). Viewed from another aspect, the present invention provides, for example, a method for designing an Eprobe that further satisfies the condition (3) or the condition (4) in addition to the condition (1) (and optionally, also the condition (2)).

(3) The labeled base is at a position at least four bases away, more preferably five bases away from a base to be paired with the mismatch, so that there is no difference in detection peak intensity between a sequence that does not have the mutation in the target sequence (full match) and a sequence that has the mutation in the target sequence (mismatch).

(4) The labeled base is at a position three or fewer bases away from the base to be paired with the mismatch, more preferably at a position two or fewer bases away from the base to be paired with the mismatch, and still more preferably at a position identical to the base to be paired with the mismatch (the labeled base is the base to be paired with the mismatch), so that there is a difference in detection peak intensity between a sequence that does not have the mutation in the target sequence (full match) and a sequence that has the mutation in the target sequence (mismatch).

In the nucleic acid probe (Eprobe) of the present invention, for example, a labeled base to which fluorescent dye moieties that exhibit an excitonic effect are bound does not necessarily hybridize to the target sequence. This is because there is a case that the labeled base exhibits fluorescence even when it does not hybridize to the target sequence. More specifically, the Eprobe of the present invention is a nucleic acid probe for use in detection of a target sequence in a nucleic acid and may be configured so that it includes a sequence that hybridizes to the target sequence and a sequence that does not hybridize to the target sequence, and a labeled base to which the fluorescent dye moieties that exhibit an excitonic effect are bound is included in the sequence that does not hybridize to the target sequence. Viewed from another aspect, the present invention provides a method for designing an Eprobe that satisfies the aforementioned conditions. With this configuration, even with respect to a target sequence for which it is usually difficult to design a corresponding probe, the detection of fluorescence becomes possible with a simple probe design by placing the labeled base at a position corresponding to the outside of the target sequence (a position not included in the sequence that hybridizes to the target sequence). The number of bases present between the labeled base to which the fluorescent dye moieties that exhibit an excitonic effect are bound and the sequence that hybridizes to the target sequence may be 0 or a positive integer. The number of bases is preferably 100 or less, more preferably 60 or less, yet more preferably 30 or less, still more preferably 25 or less, further preferably 20 or less, yet further preferably 15 or less, still further preferably 10 or less, and particularly preferably 5 or less.

While the reason (mechanism) why the labeled base may exhibit fluorescence even when it does not hybridize to the target sequence is unknown, it is speculated to be as follows, for example. That is, first, a state is created where the labeled base to which fluorescent dye moieties that exhibit an excitonic effect are bound is present in the vicinity of a double strand formed of the target sequence and a sequence that hybridizes thereto. In this state, when the base sequence that forms the Eprobe folds back (U-turns), the labeled base and the fluorescent dye moieties (dyes) approach the double strand, and the fluorescent dye moieties enter the double strand to emit fluorescence.

Furthermore, in the method for detecting an amplification product containing a mismatch region in a target sequence according to the present invention, for example, the Eprobe of the present invention that fully matches with the target sequence is added in a nucleic acid amplification reaction by the PCR method. Thereby, the full-match Eprobe hybridizes to the target region of the template sequence, and the clumping effect of suppressing the amplification of the sequence containing this region can be obtained. At this time, for example, with respect to a template (template nucleic acid) having a mismatch to the Eprobe, the clumping effect is not obtained due to weak hybridization. Accordingly, for example, this makes the detection of the mutant-type sequences that are present in small numbers easier by enriching them by the amplification reaction using a wild-type probe (the full-match Eprobe). It is preferable to design the full-match Eprobe such that the sequence to which a primer used in the PCR method hybridizes comes into competition with the target sequence to which the full-match Eprobe hybridizes. Since this causes the extension reaction from the primer hardly to occur or not to occur at all, the effect of the enrichment by the clumping can be improved further. For causing the competition between the sequence to which a primer used in the PCR method hybridizes and the target sequence, the Eprobe is designed, for example, such that the sequence to which the primer used in the PCR method hybridizes and the target sequence come close to each other. More specifically, the full-match Eprobe is designed such that the number of bases present between the sequence to which the primer used in the PCR method hybridizes and the target sequence is, for example, 7 or less, preferably 6 or less, more preferably 5 or less, and yet more preferably 4 or less in a nucleic acid containing the target sequence. The number of bases present between the sequence to which the primer used in the PCR method hybridizes and the target sequence may be, for example, 0 (that is, the target sequence may be designed right next to the sequence to which the primer used in the PCR method hybridizes). Also, for causing the competition between the sequence to which the primer used in the PCR method hybridizes and the target sequence, for example, there may be at least one base overlap between the sequence to which the primer used in the PCR method hybridizes and the target sequence (that is, one or more bases of the target sequence may overlap with the sequence to which the primer used in the PCR method hybridizes). The sequence to which the primer used in the PCR method hybridizes and the target sequence are designed such that as many bases as possible are duplicated (overlapped), and the number of duplicated (overlapped) bases is preferably 2 or more, more preferably 3 or more, and yet more preferably 4 or more. The sequence to which the primer used in the PCR method hybridizes and the target sequence are preferably overlapped partially at the 5' end, more preferably overlapped partially at the 3' end, and particularly preferably completely overlapped.

In the method for detecting an amplification product containing a mismatch region in a target sequence according to the present invention, for example, the target sequence may contain a plurality of mismatches. The Eprobe of the present invention shows a Tm value (melting temperature) that slightly varies depending on a sequence with which the probe mismatches, and the use of this property makes it possible to identify a mismatch target sequence. In conventional art, for the identification (type classification) of a plurality of mismatch sequences, detection probes corresponding to the respective mismatch sequences are required. However, the Eprobe of the present invention can conduct the identification (type classification) of a plurality of mutant-type base sequences with the Eprobe having only one type of (for example, wild-type) sequence by making use of the difference in the Tm value.

In the method for detecting a target sequence of the present invention, a nucleic acid containing the target sequence may be a double-stranded nucleic acid. For example, it has been known conventionally that a triple-stranded nucleic acid is formed by adding, to a double-stranded nucleic acid (for example, DNA or RNA), a nucleic acid having a sequence the same as either of the strands of the double-stranded nucleic acid. It is also possible to form a triple-stranded nucleic acid with the Eprobe of the present invention by designing the Eprobe such that it is complementary to a part of or the whole of either of the strands of a double-stranded nucleic acid (for example, double-stranded DNA or double-stranded RNA) and hybridizing the Eprobe to the double-stranded nucleic acid. Thereby, the target sequence of the double-stranded nucleic acid can be detected. For example, since the Eprobe of the present invention shows a high Tm value as compared to a normal single-stranded oligonucleic acid, it can hybridize to the target sequence more strongly. More specifically, for example, the Eprobe of the present invention may hybridize to the target sequence such that the Eprobe enters between the strands of the double-stranded nucleic acid. Also, for example, the Eprobe may be designed such that recombination of the double strand is caused by the hybridization of the Eprobe of the present invention to the target sequence. In the method for detecting a target sequence of the present invention, for improving the hybridization efficiency by the recombination, for example, a recombinant protein such as RecA protein may be added or a method for improving the recombination efficiency of a homologous sequence may be combined. Furthermore, for controlling the hybridization efficiency of the Eprobe of the present invention to the target sequence of the double-stranded nucleic acid, any adjuster may be added. For adjusting, for example, stringency, a denaturant such as betaine, DMSO, or the like may be added as the adjuster to adjust the reaction condition.

It is preferable that the nucleic acid probe (Eprobe) of the present invention is designed such that any base that forms a sequence capable of forming a double strand (hereinafter, referred to as the "double strand forming sequence") within the Eprobe molecules is not contained in a region consisting of 5 bases in total, namely, an exciton-labeled base, 2 bases immediately upstream from the exciton-labeled base, and 2 bases immediately downstream from the exciton-labeled base (hereinafter, referred to as the "exciton label neighborhood region"). This makes it possible to prevent the decrease in target sequence detection sensitivity and specificity due to fluorescence exhibited by self-hybridization of the exciton label (a part labeled with fluorescent dye moieties that exhibit an excitonic effect) to the molecule itself of the nucleic acid probe (Eprobe). Note here that the "exciton label neighborhood region" is more preferably a region consisting of 7 bases in total, namely, the exciton-labeled base, 3 bases immediately upstream from the exciton-labeled base, and 3 bases immediately downstream from, and is yet more preferably a region consisting of 9 bases in total, namely, the exciton-labeled base, 4 bases immediately upstream from the exciton-labeled base, and 4 bases immediately downstream from. The "double strand forming sequence" is, for example, a sequence in which the number of bases of one of the strands is 7 or more, preferably a sequence in which the number of bases of one of the strands is 5 or more, and more preferably a sequence in which the number of bases of one of the strands is 3 or more. The "double strand forming sequence" may be a palindromic sequence, or any base sequence may be contained between the double strand forming sequences. For preventing emission of non-specific fluorescence due to the dimer formation of the Eprobe, as is described above, it is desirable that the homology between the exciton label neighborhood region and the complementary sequence of any region except for the exciton label neighborhood region is 90% or lower, preferably 70% or lower, more preferably 50% or lower, and yet more preferably 30% or lower. Furthermore, it is more preferable to use the Eprobe in the embodiments described below.

When an Eprobe hybridizes to a target sequence, an extension reaction from the 3' end of the Eprobe with the target sequence as a template is hindered.

It is used in reactions including a nucleic acid amplification reaction (more preferably, PCR reaction) in the presence of polymerase and a hybridization reaction of the Eprobe to the target sequence.

In the aforementioned embodiments, the nucleic acid amplification reaction (more preferably, PCR reaction) in the presence of polymerase and the hybridization reaction of the Eprobe to the target sequence are performed as a series of reactions or are performed simultaneously.

According to the present invention, for example, the following effects can be obtained. However, these effects are given merely for illustrative purpose and do not limit the present invention.

First, according to the present invention, it is possible to improve mismatch detection sensitivity using the Eprobe in the PCR method.

For example, by suitably designing the exciton-labeled position in the Eprobe, the position of the corresponding mutation site (mismatch site), or the relative relationship between the aforementioned positions, the stability of hybridization, the detection efficiency, and the like can be improved.

More specifically, for example, the precise control of this design condition makes it possible to cause a mismatch peak to appear or to disappear even with the same sequence by changing the exciton-labeled position. Since "it is possible to cause a mismatch peak to appear", for example, it is possible to design the probe sequence that can distinguish a full match type from a mismatch type with a single probe. Also, since "it is possible to cause a mismatch peak to disappear", for example, even when a plurality of probes corresponding to the respective target sequences coexist, by narrowing down the peak of target sequence recognition to one for each and causing a peak of the mismatch type of each of them to disappear, the overlap (with other targets) due to the peak of the mismatch type can be avoided and the specificity of the detection of a peak of the full match type can be improved. This function cannot be obtained by a probe labeled with a fluorescent dye at the 3' end and the 5' end. Furthermore, by adding a full match probe to an amplification reaction, this probe functions as a wholly novel probe that takes two functions of clumping and detection, and this makes the design of a probe easier.

In addition, when the Eprobe of the present invention is used as a detection probe in the detection of a target nucleic acid using the PCR method, for example, as compared to the case in which the TaqMan (registered trademark) probe is used, the following advantages can be achieved.

In the case where the detection is performed with an extension reaction at about 70° C., while a probe requires the length for allowing the hybridization at such a temperature, the Eprobe functions with the length of, for example, about 10-mer because the binding affinity to a target sequence is strong.

The melting curve data according to a probe sequence can be obtained.

By designing a plurality of probes each having a different melting temperature (for example, each having a different length) in one amplification region, the simultaneous determination of a plurality of targets using the melting curve can be performed.

Even when the length of an amplification product is long, the determination using the melting curve can be performed.

Even when exonuclease activity does not work normally, it functions as long as the PCR reaction is in process.

By using a short Eprobe, the detection probe that does not hybridize at all during PCR reaction (for example, 65° C. or more) can be designed.

The Eprobe of the present invention can be used for the following uses (A) to (D), for example, by making use of its effects. However, these uses and effects are given merely for illustrative purpose and do not limit the present invention by any means.

(A) Recovery, Detection, and the Like of Nucleic Acid

The Eprobe of the present invention can be used in the recovery, detection, and the like of a nucleic acid as follows, for example, by making use of the effect obtained because of its high Tm value (hybridization to a target sequence is strong). That is, in conventional arts, extraction of a target nucleic acid from a sample, purification, concentration, and the like require complicated operations and there are various problems in, for example, removal of unwanted substances by washing. Here, a target nucleic acid is recovered by specifically hybridizing the Eprobe of the present invention to a target nucleic acid released from a sample without being processed or to the sample including the target nucleic acid after denaturation by heat, acid or alkali, or mixing with a detergent or the like. This makes it possible to recover or detect the target nucleic acid efficiently, by taking advantage of the property of the Eprobe of the present invention that its hybridization to the target sequence of the target nucleic acid is strong as compared to general oligonucleotide. Specifically, for example, a method for recovering or detecting poly(A) tail of expressed mRNA by hybridization with poly T oligo has been known conventionally. In this method, when the Eprobe of the present invention is used instead of general poly T oligo, the speed of recovery or detection is accelerated and the efficiency in yield and the like is improved. The Eprobe of the present invention shows a high Tm value, for example, even when the number of bases (strand length) is small. Therefore, even a nucleic acid or the like containing poly(A) tail that is too short to be, for example, recovered and detected by a conventional manner or a nucleic acid with a shorter target region can be recovered efficiently.

(B) Direct Detection Using Eprobe

Conventionally, culture (for example, selective culture using a pharmaceutical composition) and the like have been employed for detection of fungi from samples collected from foods, environments, clinical specimens, and the like and for identification of properties such as drug resistance and the like of the samples. However, according to a conventional method, a time-consuming culture that takes several hours to several days or more than several weeks resulted in a time-consuming test, and there have been, for example, problems in delay in diagnostic treatment and problems in distribution and freshness preservation of food and the like. Here, detection of a target nucleic acid by causing the Eprobe of the present invention to react with the sample so as to hybridize to a specific region and measuring its fluorescent signal allows rapid detection (test). Furthermore, for example, combination with a high sensitive fluorescence detection apparatus and adjustment of a reaction temperature, a reaction solution condition, a fluorescence reading condition, and the like achieve more precise detection. Moreover, for achieving further improvement in detection sensitivity, the detection using the Eprobe of the present invention may be performed, for example, after the amplification of a target region (target sequence) by the PCR method or the culture of fungi, viruses, cells, and the like by a usual culture method to some extent. Especially, in the case where the type classification (identification) of fungi, viruses, cells, and the like is difficult (for example, in the case of determination of drug-resistant fungi or in the case where properties of fungi, viruses, cells, and the like differ depending on the few bases difference in a base sequence), it is possible to carry out a measurement and a test promptly in a simple manner by efficiently identifying a target nucleic acid region using the Eprobe of the present invention.

(C) Amplification Detection Method Using Eprobe not Inhibiting Nucleic Acid Amplification Conventionally, methods of detecting a target nucleic acid in which the probe is degraded during its amplification and thereby emits a signal, like a TaqMan probe, for example, have been known. However, in these methods, since a nucleic acid different from a primer is bound to a template to be extended, there is a possibility of inhibiting the amplification from the primer extension reaction (obstructing the extension reaction) and this may result in the decrease in amplification efficiency. The decrease in amplification efficiency may lead to, for example, decrease in minimum detection sensitivity, decrease in reproducibility of detection with low copy number, and decrease in quantitativity. In contrast, the Eprobe of the present invention detects a target sequence only by hybridizing to the target sequence, and there is no need to be degraded as in the case of the TaqMan probe. Therefore, in the nucleic acid amplification by PCR or the like, by adjusting the length, reaction conditions, and the like of the Eprobe of the present invention, it is possible to adjust so as not to cause decrease in the amplification efficiency.

(D) Identification of Sequence or the Like Dense with Polymorphism (e.g., SNP)

Since the Eprobe of the present invention shows a high Tm value as compared to a normal HybProbe oligo (oligonucleotide serving as a probe for detecting a target sequence by hybridization), the probe can be designed shorter than the normal HybProbe oligo. As in the case of HLA, for example, when many polymorphisms occur successively in adjacent regions, there is a case that, in the vicinity of SNP recognized by one type of probe, another SNP is present. In such a case, accurate identification of only a target SNP cannot be performed with a conventional long probe. On the other hand, the Eprobe of the present invention showing a high Tm value allows, under a high stringency condition, hybridization even if it is short and accurate determination of only a target SNP.

Viewed from another aspect, according to the nucleic acid probe of the present invention, for example, the following effects (1) to (13) can be obtained. It is to be noted, however, that the following effects (1) to (13) are also given merely for illustrative purpose and do not limit the present invention by any means.

(1) The specificity to a base sequence is high.
(2) Since background noise is low, it is highly sensitive.
(3) Since the 3' end is modified with 3'-SpacerC3 and extension reaction does not occur, it allows a highly-specific reaction as a PCR probe.
(4) Since the Eprobe stabilizes DNA dimer formation, it is possible to design a short probe.
(5) The Eprobe method does not require exonuclease activity and it can be used with an enzyme not having exonuclease activity.
(6) Even when fragmentation of a nucleic acid occurred in a sample, it does not result in false positive.
(7) Quantitativity and accuracy for a sample concentration is high.
(8) Real-time PCR detection and melting curve analysis can be performed in one tube.
(9) Owing to high binding affinity, clear differences among melting curve analysis results (e.g., difference between wild-type and mutant-type) can be created.
(10) By the use of different Tm values and fluorescent dyes, a plurality of items can be detected simultaneously by designing a plurality of Eprobes.
(11) High sensitive and high specific SNP analysis can be performed.
(12) Since it is possible to design a short probe, it is not likely to be influenced by a neighborhood region other than a target.
(13) It also functions as a clumping probe in PCR and allows high sensitive mutation detection.

The nucleic acid probe of the present invention can be used, for example, as follows. However, this description is also given merely for illustrative purpose and does not limit the present invention. That is, if an exciton probe (Eprobe), which is the nucleic acid probe of the present invention, is immobilized on a chip, for example, there is no need to label a sample to be measured such as RNA, DNA, or the like (a nucleic acid having a target sequence), and detection can be performed by just dropping the sample as it is on the chip. In contrast to a liquid phase measurement system, such a measurement system allows a measurement of a plurality of samples with one chip, a measurement of different regions in one gene, or simultaneous measurement of different genes by changing the wavelengths of dyes in a plurality of samples. According to this, inner control can be set in every reaction, and essential conditions for a clinical test kit are satisfied. Particularly, a microarray using the exciton probe (Eprobe) allows the detection of hybridization without requiring fluorescent labeling of a detection target such as a PCR amplification product. Furthermore, a next specimen can be added to the microarray washed after use. This brings the advantage of repeat reuse of the microarray without requiring special labeling or color-developing reaction. Also in view of today's ecology, a reusable microarray using the exciton probe (Eprobe) is greatly in demand.

FIG. 1 schematically shows one example of a usage pattern of the nucleic acid probe (Eprobe) of the present invention. As shown in FIG. 1, for example, the presence or absence of a target product and the presence or absence of a mutation can be measured by hybridizing the Eprobe to a specimen sample on a solid-phased microarray and detecting a fluorescent signal. Furthermore, by washing the microarray, the detection of this kind can be performed using the same microarray, and the microarray can be the one that can be used repeatedly without modifying a specimen sample or requiring special colorimetric enzymatic reaction after hybridization.

Note here that the "excitonic effect" (exciton coupling) is an effect in which, for example, a plurality of dyes aggregate in parallel to form an H-aggregate and thereby hardly exhibit fluorescence emission. Conceivably, this effect is obtained as follows. That is, the excitation state of the dye is split into two energy levels by Davydov splitting, excitation to the higher energy level and then internal conversion into the lower energy level occur, and thereby the emission is thermodynamically forbidden. However, these descriptions do not limit the present invention by any means. The possible occurrence of the excitonic effect can be confirmed by the appearance of the absorption band of the dyes that have formed the H-aggregate, in a shorter wavelength as compared to the absorption band of a single dye. Examples of the dyes that exhibit such an effect include thiazole orange and derivatives thereof, oxazole yellow and derivatives thereof, cyanine and derivatives thereof, hemicyanine and derivatives thereof, and methyl red and derivatives thereof, as well as dye groups generally referred to as cyanine dyes and azo dyes. According to the excitonic effect, for example, in the case where the fluorescent dye of the present invention binds to a nucleic acid, the fluorescence intensity in a single-stranded state is suppressed and thereby allows a double helix structure to be detected further effectively.

In the nucleic acid probe (Eprobe) of the present invention, fluorescent dye moieties that exhibit an excitonic effect are each:
(i) the one that emits fluorescence, with two planar chemical structures contained in one molecule, which exist not in the same plane but with a certain angle formed therebetween, being located so as to be arranged in the same plane when the molecule undergoes intercalation into or groove binding to a nucleic acid,
(ii) the one formed of at least two dye molecule groups that do not exhibit fluorescence emission due to the excitonic effect obtained when at least two dye molecules aggregate in parallel to each other but exhibit fluorescence emission with the aggregation state being resolved when the molecules undergo intercalation into or groove binding to a target molecule, e.g. a nucleic acid, or
(iii) the one characterized in having a chemical structure of at least two dye molecules contained in one molecule, with the at least two dye molecules not exhibiting fluorescence emission due to the excitonic effect obtained when they aggregate in parallel to each other but exhibiting fluorescence emission with the aggregation state being resolved when the molecules undergo intercalation into or groove binding to a target molecule, e.g. a nucleic acid. In the case of (ii) or (iii), it is preferable that the dye molecule be the molecule described in (i).

As described above, in the nucleic acid probe (Eprobe) of the present invention, an extension-side end of the nucleic acid molecule is chemically modified, thereby preventing an extension reaction of the nucleic acid molecule. For example, the nucleic acid probe of the present invention may be configured so that the extension-side end of the nucleic acid molecule is composed of an atomic group having a deoxyribose skeleton, a ribose skeleton, or a structure derived from either one of them, and the extension-side end is chemically modified by substituting a hydrogen atom of a 3' end hydroxyl group (OH) in the atomic group with a substituent.

The substituent with which the hydrogen atom of the 3' end hydroxyl group (OH) is substituted is not particularly limited, and preferably is any one of the following (A) to (C):
(A) a substituent represented by the following chemical formula (1001):

(1001)

where in the chemical formula (1001),
X is a hydroxyl group (OH), an amino group ($NH_2$), or a group obtained by substitution of at least one hydrogen atom thereof with a substituent,
$L^{1000}$ is a linker atomic group, and
the mark "*" indicates a position at which the substituent is bound to the oxygen atom of the 3' end hydroxyl group (OH);

(B) a dideoxynucleotide group that does not have a 3' end OH (hydroxyl group) and thus prevents an extension reaction caused by polymerase; and
(C) a thiophosphoric acid diester group.

In the chemical formula (1001), $L^{1000}$ preferably is an aliphatic hydrocarbon group or an aromatic hydrocarbon group. The aliphatic hydrocarbon group may be linear, branched, or cyclic, and for example, a part thereof may be linear or branched while another part thereof may be cyclic. The aliphatic hydrocarbon may be saturated or unsaturated. The aliphatic hydrocarbon group may be an aliphatic hydrocarbon group further substituted with an aromatic hydrocarbon group (for example, phenyl methyl group=benzyl group). The aromatic hydrocarbon group may be, for example, a group further substituted with an aliphatic hydrocarbon group (for example, methyl phenyl group=tolyl group). The carbon number of the whole of the aliphatic hydrocarbon group and aromatic hydrocarbon group is not particularly limited, and is, for example, 1 to 100. Furthermore, a substituent X is not particularly limited, and examples thereof include carriers such as a GPG carrier and a styrene polymer carrier.

In the chemical formula (1001), $L^{1000}$ preferably is a linear or branched alkylene group. The length of the linear or branched alkylene group represented by the number of carbon atoms therein is not particularly limited, and is, for example, 1 to 100.

In the nucleic acid probe of the present invention, the skeleton of the nucleic acid molecule is not limited to an atomic group having a deoxyribose skeleton, a ribose skeleton, or a structure derived from either one of them, and any skeleton can be employed. For example, as will be described below, PNA or the like can be employed. For example, in the case of employing PNA, since an extension reaction due to polymerase hardly occurs, it can be used as the nucleic acid probe of the present invention without any applying particular chemical modification to the end.

[Structure of Nucleic Acid Molecule]

In the nucleic acid probe of the present invention, the nucleic acid molecule may have a structure as described in Japanese Patent No. 4370385, for example, or may have a structure as explained below, for example.

In the nucleic acid probe of the present invention, the structure of the nucleic acid molecule may be, for example, a labeled nucleic acid containing at least one of the structures represented by the following formulae (16), (16b), (17), (17b), (18), and (18b). In the present invention, the labeled nucleic acid also encompasses tautomers and stereoisomers of these structures, as well as salts of these structures, tautomers, and stereoisomers. Hereinafter, the structures represented by the following respective formulae and having dye moieties $Z^{11}$ and $Z^{12}$ that exhibit fluorescence each may be referred to as a "labeled structure". The labeled nucleic acid containing the labeled structure may be referred to as a "labeled probe".

In the present invention, the term "target nucleic acid sequence" not only refers to a nucleic acid sequence to be amplified, but also encompasses a sequence complementary thereto.

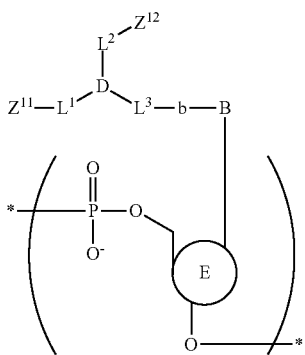

(16)

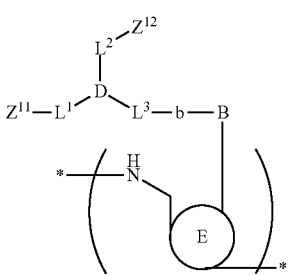

(16b)

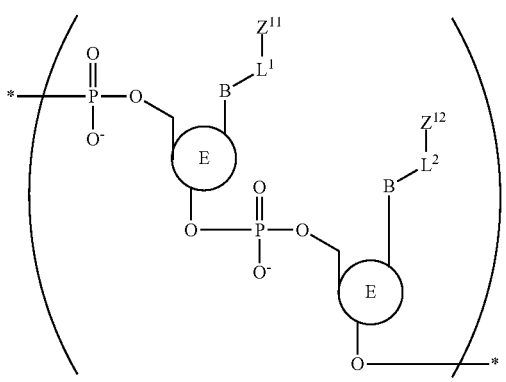

(17)

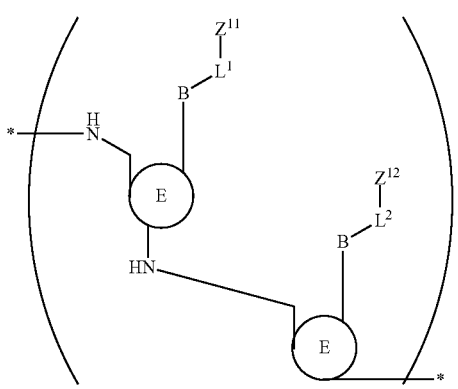

(17b)

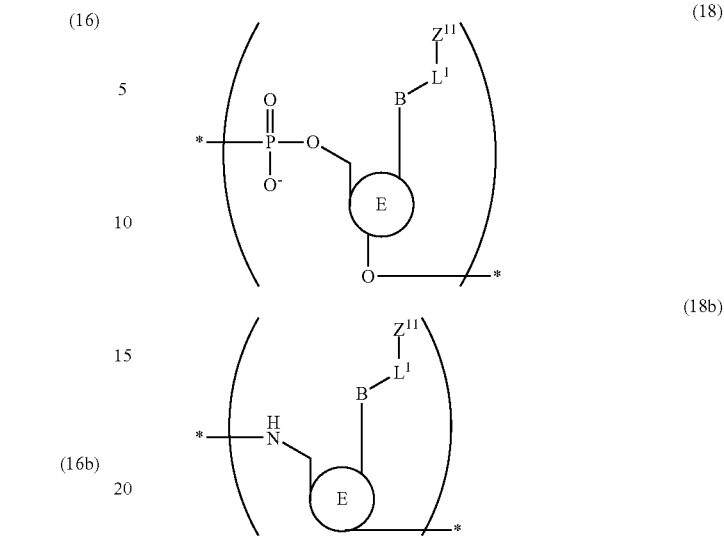

In the formulae (16), (16b), (17), (17b), (18), and (18b),

B is an atomic group having a natural nucleobase (adenine, guanine, cytosine, thymine, or uracil) skeleton or an artificial nucleobase skeleton, E is:

(i) an atomic group having a deoxyribose skeleton, a ribose skeleton, or a structure derived from either one of them, or (ii) an atomic group having a peptide structure or a peptoid structure, $Z^{11}$ and $Z^{12}$ are each an atomic group exhibiting fluorescence, and may be identical to or different from each other, $L^1$, $L^2$, and $L^3$ are each a linker (a linking atom or a linking atomic group), the main chain length (the number of main chain atoms) thereof is arbitrary, $L^1$, $L^2$, and $L^3$ each may or may not contain each of C, N, O, S, P, and Si in the main chain, $L^1$, $L^2$, and $L^3$ each may or may not contain each of a single bond, a double bond, a triple bond, an amide bond, an ester bond, a disulfide bond, an imino group, an ether bond, a thioether bond, and a thioester bond in the main chain, and $L^1$, $L^2$, and $L^3$ may be identical to or different from each other, D is CR, N, P, P=O, B, or SiR where R is a hydrogen atom, an alkyl group, or an arbitrary substituent, and b is a single bond, a double bond, or a triple bond, or alternatively, in the formulae (16) and (16b), $L^1$ and $L^2$ are each a linker, $L^3$, D, and b may not be present, and $L^1$ and $L^2$ may be bonded directly to B, provided that:

in the formulae (16), (17), and (18), E is an atomic group described in the item (i), and at least one O atom in a phosphoric acid linkage may be substituted with an S atom;

in the formulae (16b), (17b), and (18b), E is an atomic group described in the item (ii); and in the formulae (17) and (17b), the respective Bs may be identical to or different from each other, and the respective Es may be identical to or different from each other.

In the formulae (16), (17), (16b), (17b), (18), and (18b), the main chain length (the number of main chain atoms) of each of $L^1$, $L^2$, and $L^3$ preferably is an integer of 2 or more. The upper limit thereof is not particularly limited, and is, for example, 100 or less, more preferably 30 or less, and particularly preferably 10 or less.

$Z^{11}$ and $Z^{12}$ are dye moieties that exhibit an excitonic effect. With this configuration, a greater increase in fluorescence is obtained when a double helix structure is formed, for example. This allows the double helix structure to be detected still more effectively.

$Z^{11}$ and $Z^{12}$ are not particularly limited as long as they are fluorescent dye moieties that exhibit an excitonic effect. More preferably, $Z^{11}$ and $Z^{12}$ are, for example, each independently a group derived from any one of thiazole orange, oxazole yellow, cyanine, hemicyanine, other cyanine dyes, methyl red, azo dyes, and derivatives thereof. Furthermore, a group derived from any other known dye also can be used as appropriate. Many fluorescent dyes that change the fluorescence intensity by binding to nucleic acids such as DNA have been reported. In a typical example, it has been known that ethidium bromide exhibits strong fluorescence by intercalating into a double helix structure of DNA, and it is used frequently for DNA detection. Furthermore, fluorescent dyes whose fluorescence intensity can be controlled according to the microscopic polarity, such as pyrenecarboxyamide and prodan, also are known. The thiazole orange is a fluorescent dye with a benzothiazole ring and quinoline ring linked to each other with a methine group. It usually exhibits weak fluorescence but gives strong fluorescence emission by intercalating into DNA having a double helix structure. Other examples include dyes such as fluorescein and Cy3.

More preferably, $Z^{11}$ and $Z^{12}$ are each independently an atomic group represented by any one of the following formulae (7) to (9).

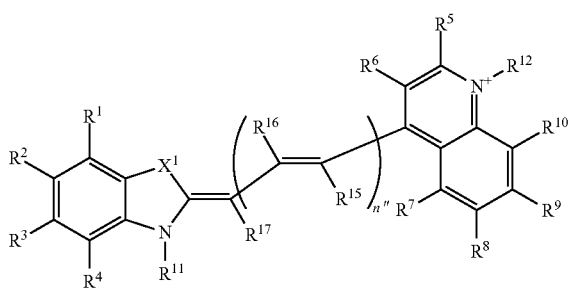

(7)

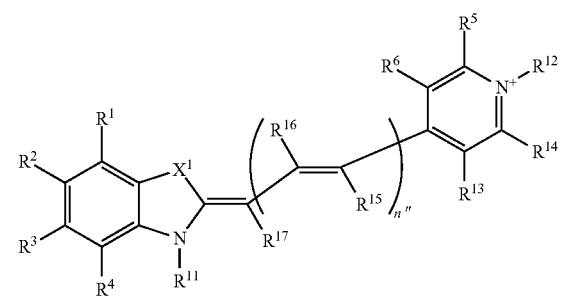

(8)

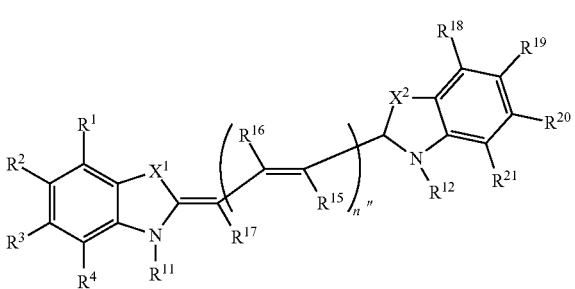

(9)

In the formulae (7) to (9), $X^1$ and $X^2$ are S, Se, or O, n" is 0 or a positive integer, $R^1$ to $R^{10}$ and $R^{13}$ to $R^{21}$ are each independently a hydrogen atom, a halogen atom, a lower alkyl group, a lower alkoxyl group, a nitro group, or an amino group, one of $R^{11}$ and $R^{12}$ is a linking group that is bound to $L^1$ or $L^2$ in the formulae (16), (17), (16b), (17b), (18), and (18b), and the other is a hydrogen atom or a lower alkyl group, when a plurality of $R^{15}$s are present in the formula (7), (8), or (9), they may be identical to or different from each other, when a plurality of $R^{16}$s are present in the formula (7), (8), or (9), they may be identical to or different from each other, and $X^1$, $X^2$, and $R^1$ to $R^{21}$ in $Z^{11}$ and $X^1$, $X^2$, and $R^1$ to $R^{21}$ in $Z^{12}$ may be identical to or different from each other, respectively.

In the formulae (7) to (9), it is more preferable that, in $R^1$ to $R^{21}$, the lower alkyl group is a linear or branched alkyl group with a carbon number of 1 to 6, and the lower alkoxyl group is a linear or branched alkoxyl group with a carbon number of 1 to 6.

In the formulae (7) to (9), it is more preferable that in $R^1$ and $R^{12}$, the linking group is a polymethylene carbonyl group with a carbon number of at least 2 and is bound to $L^1$ or $L^2$ in the formula in the formula (16), (17), (16b), (17b), (18) or (18b) in the carbonyl group moiety. The upper limit of the carbon number of the polymethylene carbonyl group is not particularly limited, and is, for example, 100 or less, preferably 50 or less more preferably 30 or less, and particularly preferably 10 or less.

When $Z^{11}$ and $Z^{12}$ are each represented by any one of the formulae (7) to (9), it is more preferable that they are, for example, each independently a group represented by formula (19) or (20).

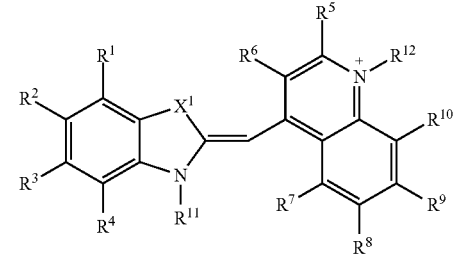

(19)

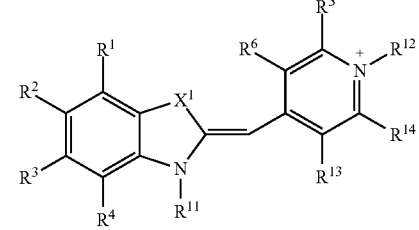

(20)

In the formulae (19) and (20), $X^1$ denotes —S— or —O—. $R^1$ to $R^{10}$ and $R^{13}$ and $R^{14}$ each independently indicates a hydrogen atom, a halogen atom, a lower alkyl group, a lower alkoxyl group, a nitro group, or an amino group. One of $R^{11}$ and $R^{12}$ is a linking group that is bound to $L^1$ or $L^2$ in the formulae (16), (17), (16b), (17b), (18), and (18b), and the other is a hydrogen atom or a lower alkyl group.

Particularly preferably, $Z^{11}$ and $Z^{12}$ are each independently an atomic group represented by any one of the following chemical formulae.

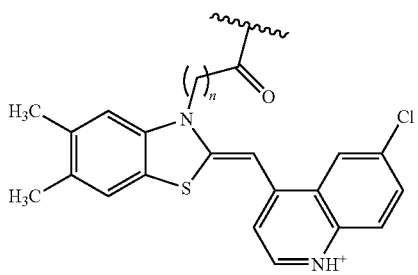

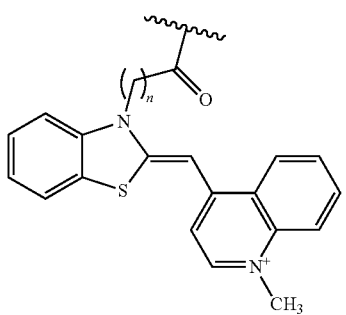

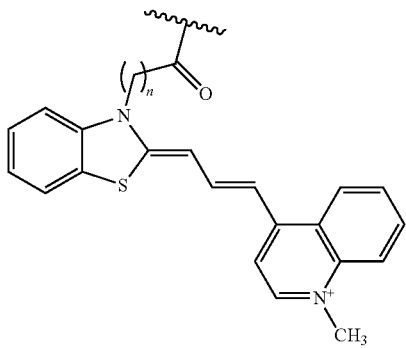

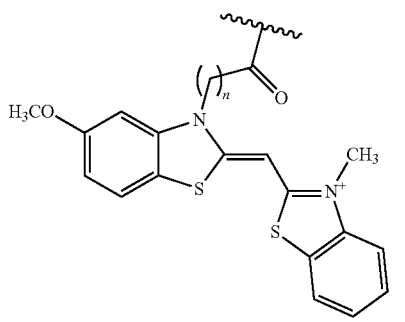

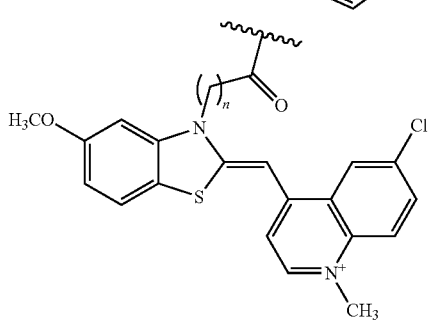

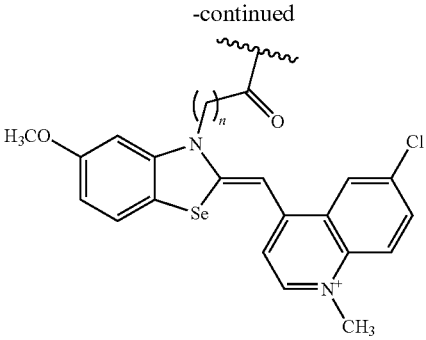

In each of the above chemical formulae, it is particularly preferable that n is a positive integer and in the range from 2 to 6.

In the formulae (16), (17), (16b), (17b), (18), and (18b), B may have a natural nucleobase skeleton, and also, as described above, may have an artificial nucleobase skeleton. For example, B preferably is a structure represented by Py (pyrimidine ring), Py der., Pu (purine ring), or Pu der. The Py is an atomic group having a covalent bond to E in the 1-position and a covalent bond to a linker moiety in the 5-position in a six-membered ring represented by the following formula (11). The Py der. is an atomic group in which at least one of all the atoms of the six-membered ring of the Py has been substituted with an N, C, S, or O atom, and the N, C, S, or O atom optionally may have an electric charge, a hydrogen atom, or a substituent. The Pu is an atomic group having a covalent bond to E in the 9-position and a covalent bond to a linker moiety in the 8-position in a condensed ring represented by the following formula (12). The Pu der. is an atomic group in which at least one of all the atoms of a five-membered ring of the Pu has been substituted with an N, C, S, or O atom, and the N, C, S, or O atom optionally may have an electric charge, a hydrogen atom, or a substituent.

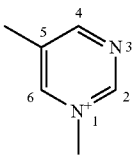 (11)

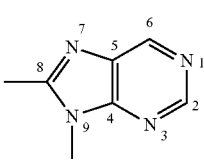 (12)

The nucleic acid molecule in the nucleic acid probe of the present invention may include, for example, at least one of nucleotide structures represented by the following chemical formulae 106, 110, 113, 117, 120, 122, 123, 124, and 114-2, geometric isomers and stereoisomers thereof, and salts thereof.

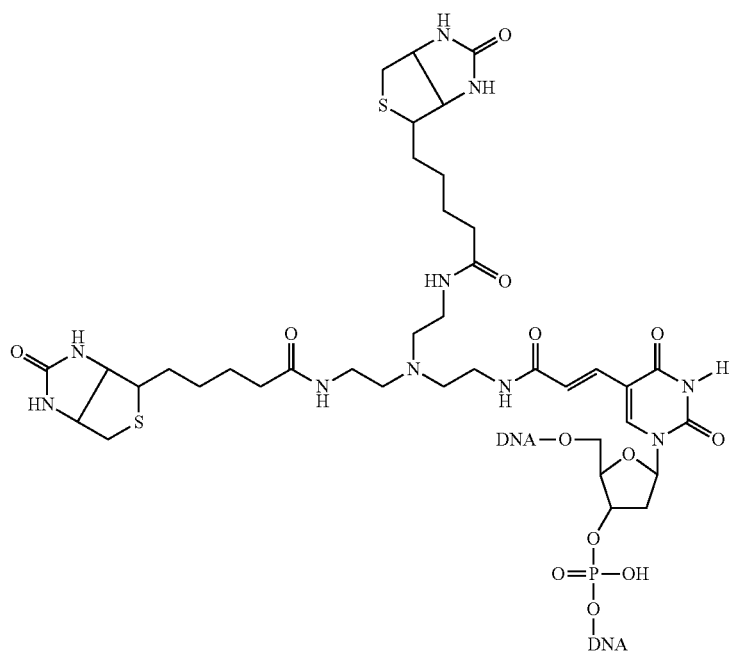
106
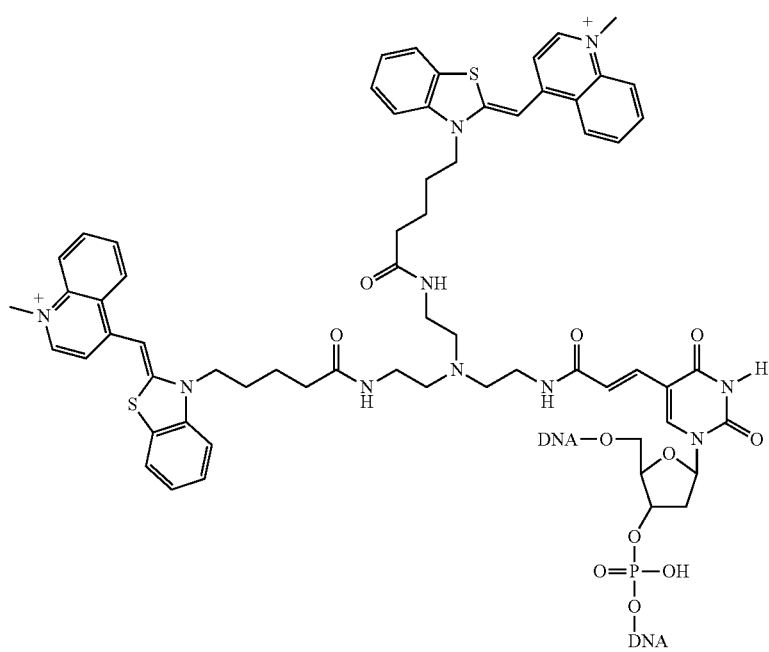
110

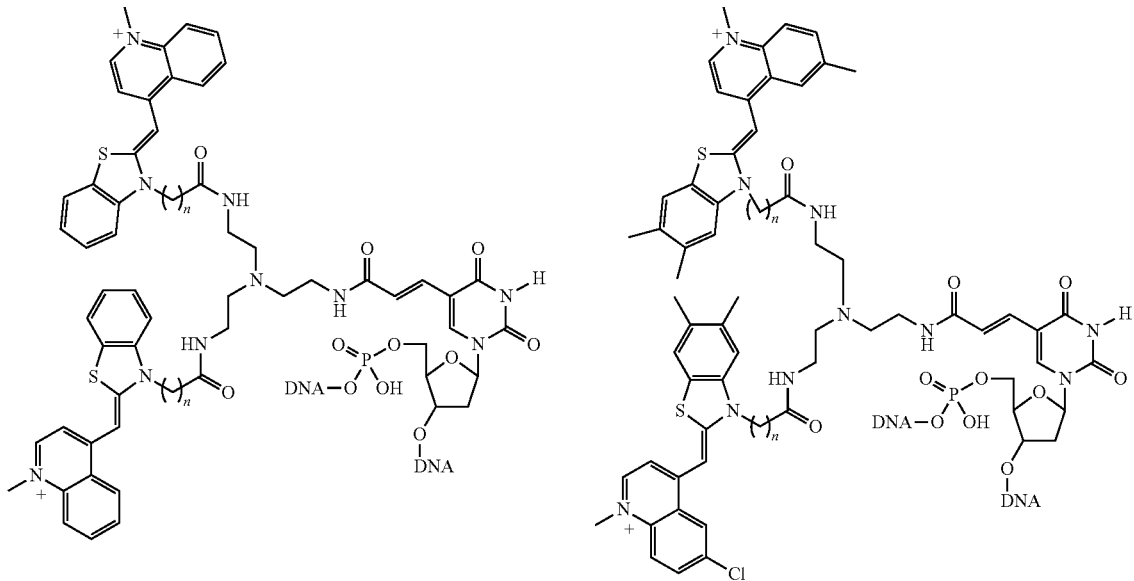
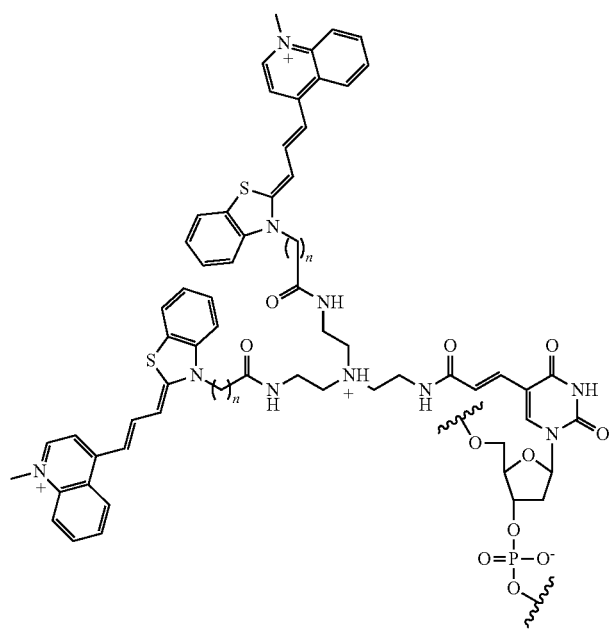

(122)
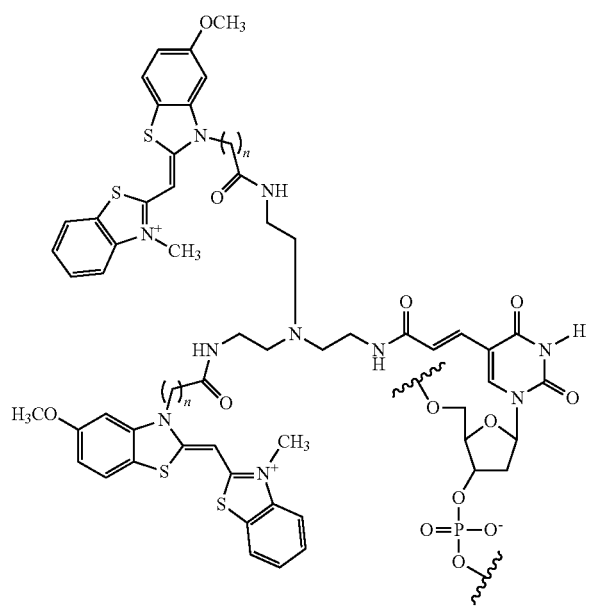
(123)
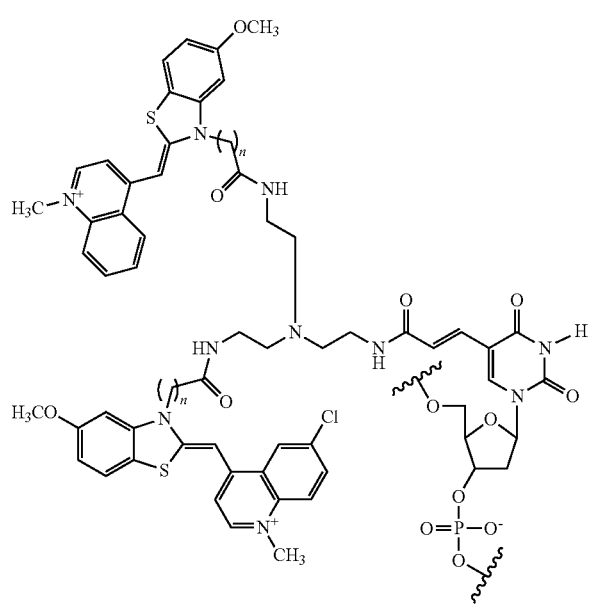

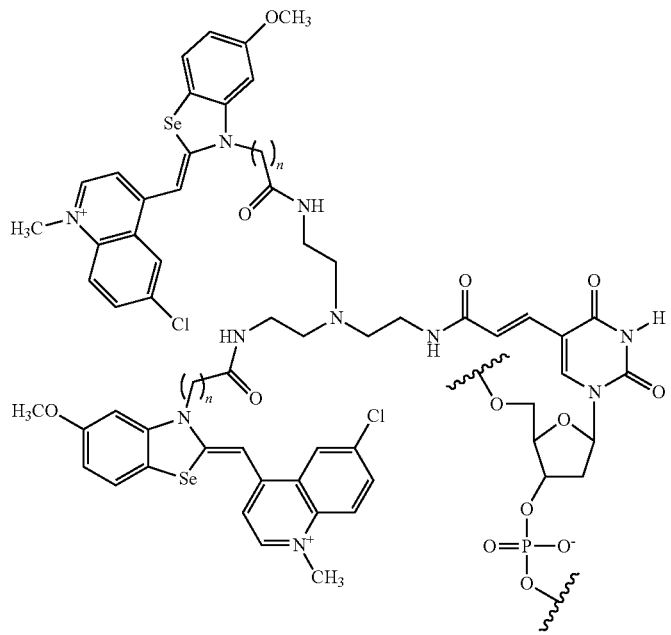

(124)

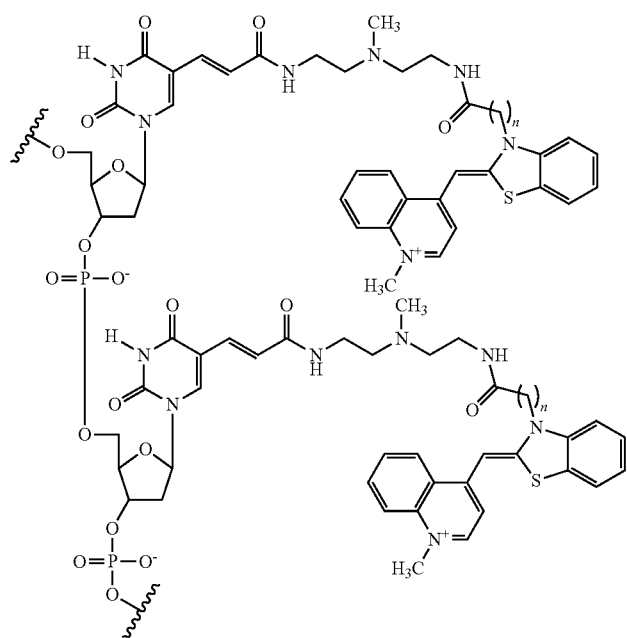

(114-2)

In the chemical formulae 106, 110, 113, 117, 120, 122, 123, 124, and 114-2, the linker length n preferably is a positive integer and in the range from 2 to 6.

The number of the labeled structures included in the nucleic acid probe of the present invention is not particularly limited, and is, for example, about 1 to about 100, preferably about 1 to about 20. In the labeled probe, the site at which the labeled structure is included also is not particularly limited.

In the nucleic acid probe (labeled nucleic acid) of the present invention, the basic skeleton of each nucleic acid is not particularly limited. Examples thereof include oligonucleotides, modified oligonucleotides, oligonucleosides, modified oligonucleosides, polynucleotides, modified polynucleotides, polynucleosides, modified polynucleosides, DNAs, modified DNAs, RNAs, modified RNAs, LNAs, PNAs (peptide nucleic acids), chimeric molecules thereof, and other structures. Furthermore, the basic skeleton of each nucleic acid may be a natural one or an artificially synthesized one. In the case of the nucleic acid probe of the present invention, the nucleic acid is not particularly limited as long as it can provide base pairing, for example. In the case of a nucleic acid sample or a target nucleic acid sequence, the nucleic acid is not particularly limited as long as, for example, it serves as a template for synthesizing a complementary strand. Therefore the nucleic acid may be a nucleotide derivative, a part or the whole of which is formed of a completely artificial structure, for example. Examples of artificial bases that compose the nucleic acid include, but are not limited to, 2-amino-6-(N,N-dimethylamino)purine pyridin-2-one, 5-methylpyridin-2-one, 2-amino-6-(2-thienyl)purine, pyrrole-2-carbaldehyde, 9-Methylimidazo[(4,5)-b]pyridine, 5-iodo-2-oxo(1H)pyridine 2-oxo-(1H)pyridine, 2-amino-6-(2-thiazolyl)purine, and 7-(2-thienyl)-imidazo[4,5-b]pyridine. In the nucleic acid probe of the present invention, the basic skeleton preferably is an oligonucleotide, a polynucleotide, a DNA, or a modified product thereof. In the present invention, the "nucleotide" may be either deoxynucleotide or ribonucleotide, for example, and the "oligonucleotide" and "polynucleotide" each may be composed of either one of deoxynucleotide and ribonucleotide or may contain both of them. In the present invention, the number of bases that compose the nucleic acid is not particularly limited. Generally, the term "nucleic acid" is synonymous with the term "polynucleotide". Generally, the term "oligonucleotide" is used as a term indicating a polynucleotide composed of a particularly small number of bases, among polynucleotides. In general, a polynucleotide of, for example, 2- to 100-mer, more generally about 2- to 50-mer is referred to as "oligonucleotide", but it is not limited by these numerical values. In the present invention, the term "polynucleotide" also should be interpreted to encompass, for example, polynucleotide and oligonucleotide, as well as artificially synthesized nucleic acids such as peptide nucleic acid, morpholine nucleic acid, methylphosphonate nucleic acid, and S-oligonucleic acid.

Generally, the peptide nucleic acid (PNA) has a structure in which a deoxyribose main chain of oligonucleotide has been substituted with a peptide main chain. Examples of the peptide main chain include a repeating unit of N-(2-aminoethyl)glycine bound by an amide bond. Examples of the base to be bounded to the peptide main chain of PNA include, but not limited to: naturally-occurring bases such as thymine, cytosine, adenine, guanine, inosine, uracil, 5-methylcytosine, thiouracil, and 2,6-diaminopurine; and artificial bases such as bromothymine, azaadenine, and azaguanine.

Generally, LNA is a nucleic acid having two cyclic structures in which, in a sugar-phosphoric acid skeleton, an oxygen atom in the 2'-position and a carbon atom in the 4'-position of ribose are bound to each other by methylene crosslinking. When oligonucleotide containing LNA anneals to DNA, the double-stranded conformation is changed, whereby the thermal stability is improved. LNA has a stronger binding affinity to a nucleic acid than common oligonucleotide. Thus, for example, depending on the conditions for designing the oligonucleotide, more reliable and stronger hybridization can be achieved.

The nucleic acid probe of the present invention includes at least one labeled structure having the above-described fluorescent dye moieties. With this configuration, the nucleic acid probe of the present invention has higher specificity to a target and hybridizes to the target more strongly, as compared with an unlabeled nucleic acid that does not include the fluorescent dye moieties, for example. That is, the nucleic acid probe of the present invention has a higher melting temperature (Tm value) than an unlabeled nucleic acid that has a basic skeleton having the same base sequence and the same nucleic acid fragment length. Thus, the nucleic acid probe of the present invention can hybridize to a target more strongly as compared with the unlabeled nucleic acid. Accordingly, the nucleic acid probe of the present invention allows detection to be carried out efficiently with high specificity, for example.

Because the nucleic acid probe of the present invention also has the above-described characteristics, it can be applied as technology to improve the specificity of amplification by increasing the Tm value, similarly to, for example, conventional PNA or LNA. Furthermore, when PNA or LNA is employed for the basic skeleton of the nucleic acid probe of the present invention, the Tm value can be increased further as compared with unlabeled PNA or LAN, so that the hybridization efficiency can be improved still further. In particular, when mutations of one to several bases are to be discriminated or when insertion or deletion is to be detected as will be described below, the use of the labeled nucleic acid (including, for example, labeled PNA and labeled LNA) of the present invention allows detection to be carried out efficiently with high specificity. When the nucleic acid probe of the present invention is used, a large difference in Tm value and a difference in hybridization efficiency are obtained between the cases where it fully matches or mismatches with a target sequence. Accordingly, mutation detection such as single base discrimination can be carried out more easily. Moreover, since the labeled probe of the present invention has a higher Tm value than the unlabeled nucleic acid, it also is applicable to, for example, a PCR clamp method, a PNA PCR clamp method, an LNA PCR clamp method, and a PNA-LNA PCR clamp method, in which it binds to a specific region strongly, masks the region, and does not serve as a template for amplification.

The number of bases contained in the nucleic acid probe of the present invention is not particularly limited, and may be, for example, about 3 to about 100, preferably 6 to 50, and more preferably 6 to 25.

The sequence of the nucleic acid probe according to the present invention is not particularly limited, and can be set as appropriate according to, for example, the sequence of a target nucleic acid sequence to be amplified, information about the sequences around the target nucleic acid sequence in, for example, DNA or RNA, and the type of the nucleic acid amplification reaction (the nucleic acid amplification method) in which the nucleic acid probe of the present invention is used. The sequence of the nucleic acid probe can be set by a conventionally known method. Usually, the sequence of the nucleic acid probe is designed in such a manner that a target nucleic acid sequence in a nucleic acid such as DNA or RNA hybridizes to the nucleic acid under a stringent condition so that the target nucleic acid sequence is contained in the amplification product. The "stringent condition" can be determined depending on, for example, the melting temperature Tm (° C.) of the double strand formed of the nucleic acid probe of the present invention and a complementary strand thereto, and the salt concentration of the hybridization solution. Specific examples can be found in a reference such as J. Sambrook, E. F. Frisch, T. Maniatis; Molecular Cloning 2nd edition, Cold Spring Harbor Laboratory (1989). For example, when hybridization is carried out at a temperature slightly lower than the melting temperature of the nucleic acid probe, the nucleic acid probe can hybridize specifically to a nucleic acid having a target nucleic acid sequence. The nucleic acid probe as described above can be designed using commercially available primer construction software such as Primer 3 (manufactured by Whitehead Institute for Biomedical Research), for example.

[Raw Material of Nucleic Acid Probe]

The raw material of the nucleic acid probe of the present invention is not particularly limited, and may be a compound, a nucleic acid, or a labeling substance to be described below, for example.

The compound is a compound having a structure derived from a mononucleoside or a mononucleotide, and the structure is a compound represented by the following formula (1), (1b), or (1c), a tautomer or stereoisomer thereof, or a salt thereof.

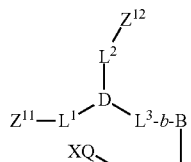
(1)

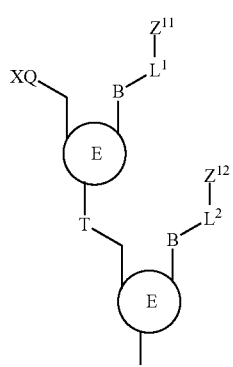
(1b)

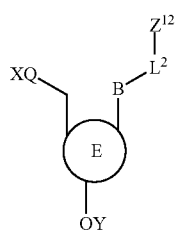
(1c)

In the formulae (1), (1b) and (1c),

B is an atomic group having a natural nucleobase (adenine, guanine, cytosine, thymine, or uracil) skeleton or an artificial nucleobase skeleton, E is:
(i) an atomic group having a deoxyribose skeleton, a ribose skeleton, or a structure derived from either one of them, or
(ii) an atomic group having a peptide structure or a peptoid structure, $Z^{11}$ and $Z^{12}$ are each a hydrogen atom, a protecting group, or an atomic group that exhibits fluorescence, and may be identical to or different from each other, Q is:
O, when E is an atomic group described in the item (i), or
NH, when E is an atomic group described in the item (ii), X is:
a hydrogen atom, a protecting group of a hydroxyl group that can be deprotected with acid, a phosphate group (a monophosphate group), a diphosphate group, or a triphosphate group, when E is an atomic group described in the item (i) or
a hydrogen atom or a protecting group of an amino group, when E is an atomic group described in the item (ii), Y is:
a hydrogen atom, a protecting group of a hydroxyl group, or a phosphoramidite group, when E is an atomic group described in the item (i), or
a hydrogen atom or a protecting group, when E is an atomic group described in the item (ii), $L^1$, $L^2$, and $L^3$ are each a linker (a linking atom or a linking atomic group), the main chain length (the number of main chain atoms) thereof is arbitrary, $L^1$, $L^2$, and $L^3$ each may or may not contain each of C, N, O, S, P, and Si in the main chain, $L^1$, $L^2$, and $L^3$ each may or may not contain each of a single bond, a double bond, a triple bond, an amide bond, an ester bond, a disulfide bond, an imino group, an ether bond, a thioether bond, and a thioester bond in the main chain, and $L^1$, $L^2$, and $L^3$ may be identical to or different from each other, D is CR, N, P, P=O, B, or SiR, and R is a hydrogen atom, an alkyl group, or an arbitrary substituent, b is a single bond, a double bond, or a triple bond, or alternatively, in the formula (1), $L^1$ and $L^2$ are each a linker, $L^3$, D, and b may not be present, and $L^1$ and $L^2$ may be bonded directly to B, and in the formula (1b), T is:
a phosphoric acid linkage ($PO_4^-$) in which at least one oxygen atom (O) may be substituted with a sulfur atom (S), when E is an atomic group described in the item (i), or
NH, when E is an atomic group described in the item (ii).

In the formulae (1), (1b) and (1c), E preferably is an atomic group having a main chain structure of, for example, DNA, modified DNA, RNA, modified RNA, LNA, or PNA (peptide nucleic acid).

In the formulae (1) and (1c), preferably, the atomic group represented by:

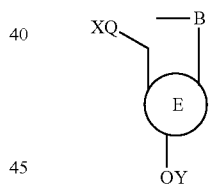

is an atomic group represented by any one of the following formulae (2) to (4),

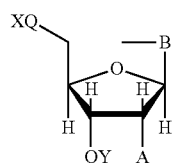
(2)

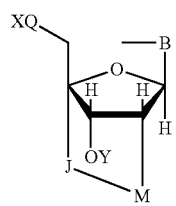
(3)

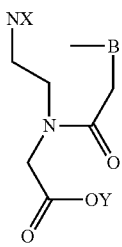
(4)

and in the formula (1b), preferably, an atomic group represented by:

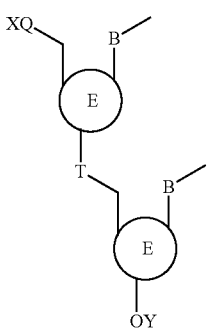

is an atomic group represented by any one of the following formulae (2b) to (4b).

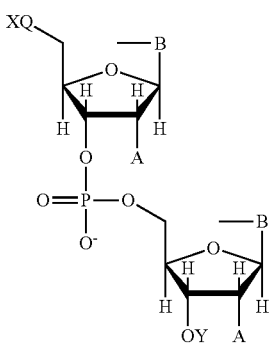
(2b)

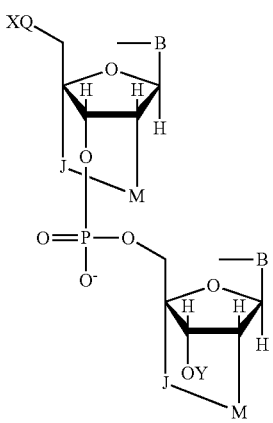
(3b)

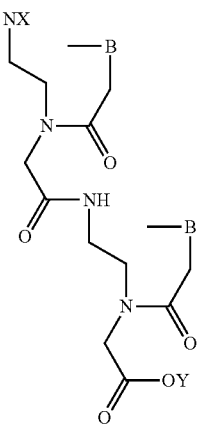
(4b)

In the formulae (2) to (4) and (2b) to (4b),

A is a hydrogen atom, a hydroxyl group, an alkyl group, an alkoxyl group, or an electron-withdrawing group, M and J are each $CH_2$, NH, O, or S and may be identical to or different from each other, B, X, and Y are identical to those, respectively, in the formula (1), (1b), or (1c), and in the formulae (2), (3), (2b), and (3b), at least one O atom contained in a phosphoric acid linkage may be substituted with an S atom.

E preferably is an atomic group having a main chain structure of, for example, DNA, modified DNA, RNA, or modified RNA from the viewpoint of easy synthesis, for example. However, E may be an atomic group having a main chain structure of LNA or PNA (peptide nucleic acid).

In the formulae (2) and (2b), it is preferable that, in A, the alkyl group is a methyl group, the alkoxyl group is a methoxyl group, and the electron-withdrawing group is halogen, for example.

In the formula (1), (1b), or (1c), it is preferable that the main chain length (the number of main chain atoms) of each of $L^1$, $L^2$, and $L^3$ is an integer of 2 or more. The upper limit of the main chain length (the number of main chain atoms) of each of $L^1$, $L^2$, and $L^3$ is not particularly limited as described above, and is, for example, 100 or less.

Preferably, the compound is a compound represented by the following formula (5), (6), (6b), or (6c), a tautomer or stereoisomer thereof, or a salt thereof.

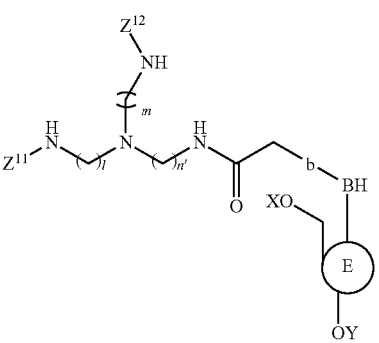
(5)

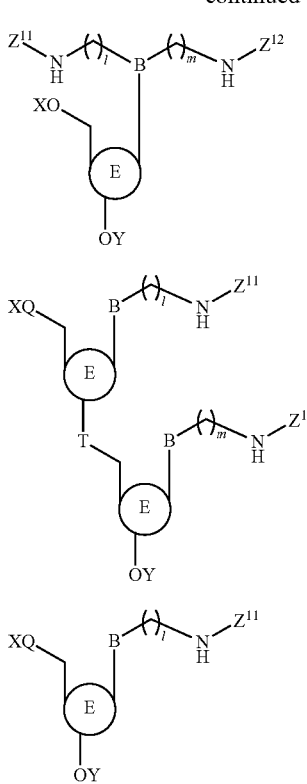

In the formulae (5), (6), (6b) and (6c), l, m and n' are arbitrary, l, m and n' may be identical to or different from each other, l, m and n' each may or may not contain each of C, N, O, S, P, and Si in a main chain thereof, and l, m and n' each may or may not contain each of a single bond, a double bond, a triple bond, an amide bond, an ester bond, a disulfide bond, an imino group, an ether bond, a thioether bond, and a thioester bond in the main chain. B, E, $Z^{11}$, $Z^{12}$, b, X, Y, and T are identical to those in the formulae (1) and (1b), respectively. In the formulae (5), (6), (6b), and (6c), l, m, and n' are each preferably an integer of 2 or more. The upper limits of l, m, and n' are not particularly limited, and are, for example 100 or less, more preferably 30 or less, and particularly preferably 10 or less.

In the compound, it is preferable that $Z^{11}$ and $Z^{12}$ are dye moieties that exhibit an excitonic effect. This allows fluorescence to be increased greatly when, for example, a double helix structure is formed, so that the double helix structure can be detected further effectively. However, in the compound, it is possible to detect the double helix structure effectively even when $Z^{11}$ and $Z^{12}$ are not dye moieties that exhibit an excitonic effect or even when only one dye moiety (dye) that exhibits fluorescence is introduced into one molecule.

Preferably, $Z^{11}$ and $Z^{12}$ are, for example, dye moieties having fluorescence as described above. The dye moieties having fluorescence are not particularly limited. More preferably, $Z^{11}$ and $Z^{12}$ are, for example, each independently a group derived from any one of thiazole orange, oxazole yellow, cyanine, hemicyanine, other cyanine dyes, methyl red, azo dyes, and derivatives thereof. Furthermore, a group derived from any other known dye also can be used as appropriate. Many fluorescent dyes that change the fluorescence intensity by binding to nucleic acids such as DNA have been reported. In a typical example, it has been known that ethidium bromide exhibits strong fluorescence by intercalating into a double helix structure of DNA, and it is used frequently for DNA detection. Furthermore, fluorescent dyes whose fluorescence intensity can be controlled according to the microscopic polarity, such as pyrenecarboxyamide and prodan, also are known. The thiazole orange is a fluorescent dye with a benzothiazole ring and quinoline ring being linked to each other with a methine group. It usually exhibits weak fluorescence but gives strong fluorescence emission by intercalating into DNA having a double helix structure. Other examples include dyes such as fluorescein and Cy3.

More preferably, $Z^{11}$ and $Z^{12}$ are, for example, each independently an atomic group represented by any one of the following formulae (7) to (9).

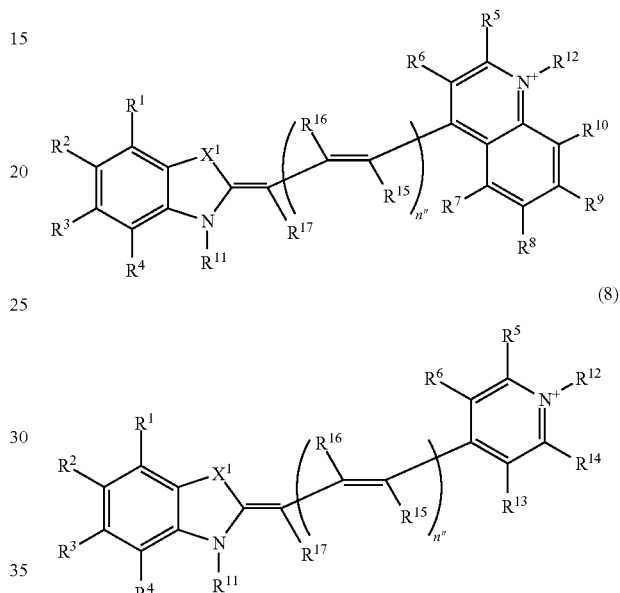

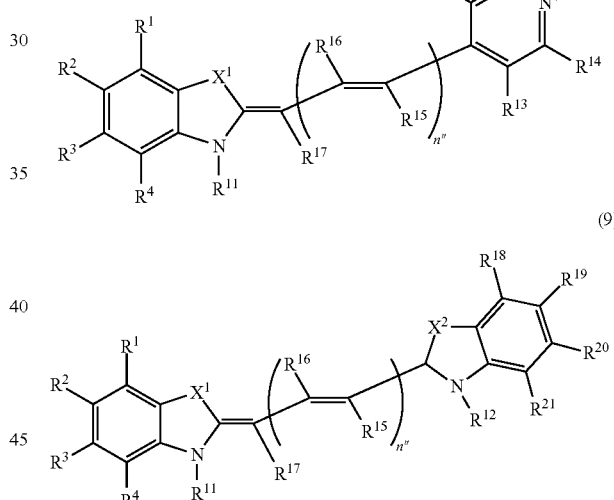

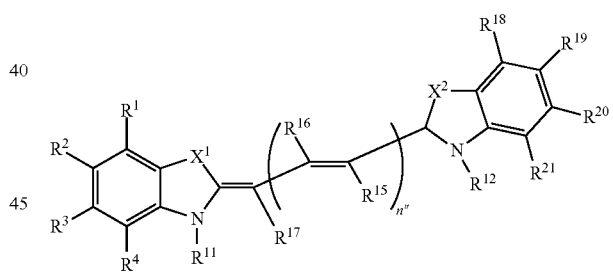

In the formulae (7) to (9), $X^1$ is S, O, or Se, n" is 0 or a positive integer, $R^1$ to $R^{10}$ and $R^{13}$ to $R^{21}$ are each independently a hydrogen atom, a halogen atom, a lower alkyl group, a lower alkoxyl group, a nitro group, or an amino group, one of $R^{11}$ and $R^{12}$ is a linking group that is bound to $L^1$ or $L^2$ in the formula (1), (1b), or (1c) or NH in the formula (5), (6), (6b), or (6c), and the other is a hydrogen atom or a lower alkyl group, when a plurality of R15s are present in the formula (7), (8), or (9), they may be identical to or different from each other, when a plurality of R16s are present in the formula (7), (8), or (9), they may be identical to or different from each other, and $X^1$ and $R^1$ to $R^{21}$ in $Z^{11}$ and $X^1$ and $R^1$ to $R^{21}$ in $Z^{12}$ may be identical to or different from each other, respectively.

In the formulae (7) to (9), it is more preferable that, in $R^1$ to $R^{21}$, the lower alkyl group is a linear or branched alkyl group with a carbon number of 1 to 6, and the lower alkoxyl group is a linear or branched alkoxyl group with a carbon number of 1 to 6.

In the formulae (7) to (9), it is more preferable that, in $R^{11}$ and $R^{12}$, the linking group is a polymethylene carbonyl group with a carbon number of at least 2 and binds to $L^1$ or $L^2$ in the formula (1), (1b), or (1c) or NH in the formula (5), (6), (6b), or (6c) in the carbonyl group moiety. The upper limit of the carbon number of the polymethylene carbonyl group is not particularly limited, and is, for example, 100 or less.

When $Z^{11}$ and $Z^{12}$ each are represented by any one of the formulae (7) to (9), it is more preferable that they are, for example, each independently a group represented by formula (19) or (20).

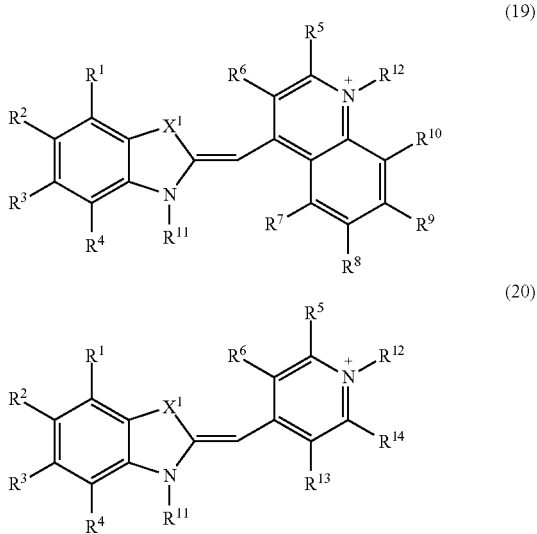

In the formulae (19) and (20), $X^1$ denotes —S— or —O—. $R^1$ to $R^{10}$ and $R^{13}$ and $R^{14}$ each independently indicates a hydrogen atom, a halogen atom, a lower alkyl group, a lower alkoxyl group, a nitro group, or an amino group. One of $R^{11}$ and $R^{12}$ is a linking group that is bound to $L^1$ or $L^2$ in the formula (1), (1b), or (1c) or NH in the formula (5), (6), (6b), or (6c), and the other is a hydrogen atom or a lower alkyl group.

The compound may be, for example, a compound having a structure represented by the following formula (10), a tautomer or stereoisomer thereof, or a salt thereof.

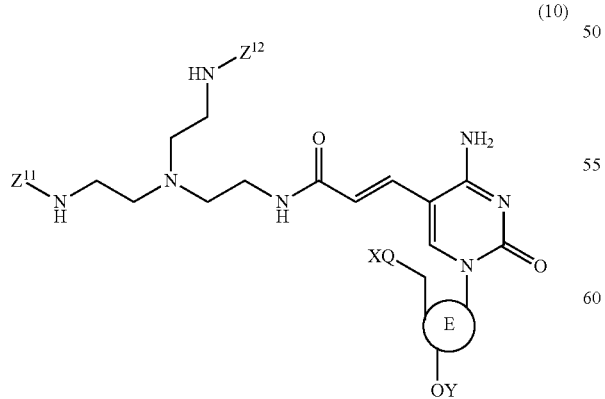

In the formula (10),

E, $Z^{11}$, $Z^{12}$, Q, X, and Y are identical to those in the formula (1), respectively.

In the formulae (1), (1b), and (1c), B may have a natural nucleobase skeleton, and also, as described above, may have an artificial nucleobase skeleton. For example, B preferably is a structure represented by Py, Py der., Pu, or Pu der. The Py is an atomic group having a covalent bond to E in the 1-position and a covalent bond to a linker moiety in the 5-position in a six-membered ring represented by the following formula (11). The Py der. is an atomic group in which at least one of all the atoms of the six-membered ring of the Py has been substituted with an N, C, S, or O atom, and the N, C, S, or O atom optionally may have an electric charge, a hydrogen atom, or a substituent. The Pu is an atomic group having a covalent bond to E in the 9-position and a covalent bond to a linker moiety in the 8-position in a condensed ring represented by the following formula (12). The Pu der. is an atomic group in which at least one of all the atoms of a five-membered ring of the Pu has been substituted with an N, C, S, or O atom, and the N, C, S, or O atom optionally may have an electric charge, a hydrogen atom, or a substituent.

The compound may be, for example, a compound represented by the following formula (13) or (14), a tautomer or stereoisomer thereof, or a salt thereof.

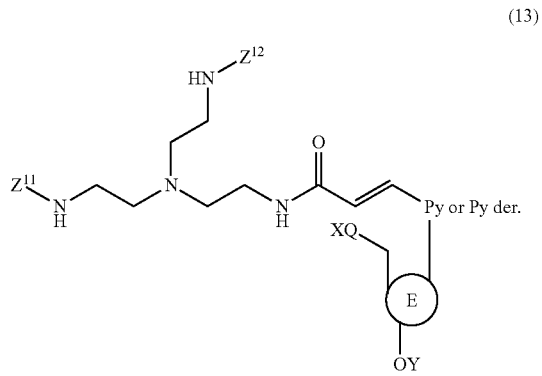

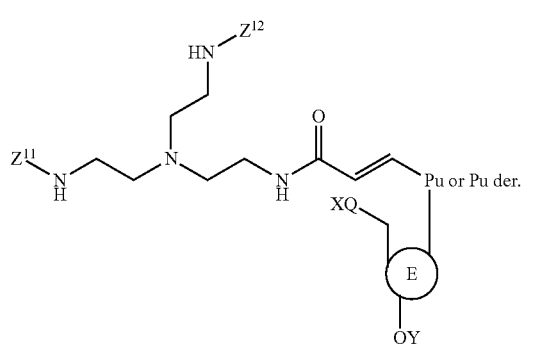

In the formulae (13) and (14), E, $Z^{11}$, $Z^{12}$, Q, X, and Y are identical to those in the formula (1), respectively, and Py, Py der., Pu, and Pu der. are as defined above.

When the compound has a phosphoramidite group, it is preferable that the phosphoramidite group is represented by, for example, the following formula (15):

$$-P(OR^{22})N(R^{23})(R^{24}) \qquad (15)$$

In the formula (15), $R^{22}$ is a protecting group of a phosphate group, and $R^{23}$ and $R^{24}$ are each an alkyl group or an aryl group.

In the formula (15), it is more preferable that $R^{22}$ is a cyanoethyl group and that, in $R^{23}$ and $R^{24}$, the alkyl group is an isopropyl group and the aryl group is a phenyl group.

In the compound, for example, the compound represented by the above formula (1) may be a compound represented by the following formula (21).

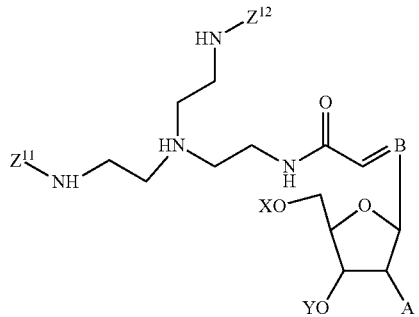

(21)

In the formula (21), A is a hydrogen atom or a hydroxyl group. Preferably, A is a hydrogen atom. B is a residue of adenine, guanine, cytosine, thymine, or uracil. For example, adenine and guanine have been bonded to a double bond in the 8-position, and cytosine, thymine, or uracil has been bonded to a double bond in the 5-position. $Z^{11}$ and $Z^{12}$ are each independently an atomic group that exhibits fluorescence, a hydrogen atom, or a protecting group of an amino group. Particularly preferably, they are each independently a residue of a thiazole orange derivative or an oxazole yellow derivative. X is a hydrogen atom, a protecting group of a hydroxyl group that can be deprotected with acid, a monophosphate group, a diphosphate group, or a triphosphate group. Y is a hydrogen atom, a protecting group of a hydroxyl group, or a phosphoramidite group.

It is more preferable that the compound represented by the formula (21) is represented by the following formula (22).

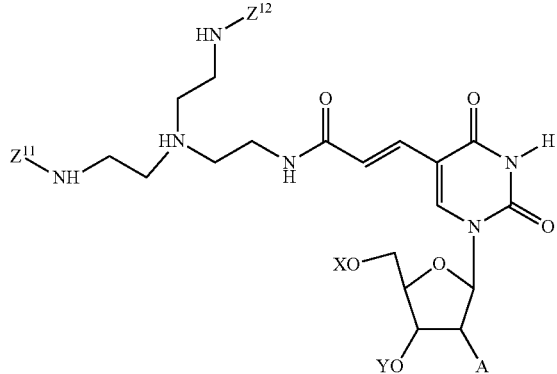

(22)

In the formula (22), A is a hydrogen atom or a hydroxyl group. $Z^{11}$ and $Z^{12}$ are each independently a dye moiety that exhibits fluorescence, a hydrogen atom, or a protecting group of an amino group, and particularly preferably a residue of a thiazole orange derivative or an oxazole yellow derivative. X is a hydrogen atom, a protecting group of a hydroxyl group that can be deprotected with acid, a monophosphate group, a diphosphate group, or a triphosphate group. Y is a hydrogen atom, a protecting group of a hydroxyl group, or a phosphoramidite group.

In the compound of the formula (21) or (22), when $Z^{11}$ and $Z^{12}$ are each a hydrogen atom or a protecting group of an amino group, two amino groups (or protected amino groups) are contained in one molecule. Thus, by utilizing these amino groups, two labeled molecules can be introduced into one molecule. For example, when labeled nucleic acid is produced, with, for example, a fluorescent substance or a chemiluminescent substance being bound thereto, the nucleic acid detection sensitivity can be improved. Furthermore, as in the case where $Z^{11}$ and $Z^{12}$ are each a dye moiety that exhibits fluorescence, labeling a nucleic acid with a specific fluorescent substance makes it possible to detect it easily.

Furthermore, the compound of the formula (21) or (22) in which $Z^{11}$ and $Z^{12}$ are each a dye moiety that exhibits fluorescence is nucleoside or nucleotide modified with two fluorescence molecules, each of which is, for example, a thiazole orange derivative or an oxazole yellow derivative. When a probe composed of a single-stranded nucleic acid containing such a compound is used by itself, it emits very weak fluorescence owing to quenching caused by exciton coupling. However, it emits strong fluorescence when it hybridizes with DNA or RNA. That is, for example, the fluorescence of the thiazole orange derivative or the oxazole yellow derivative is suppressed strongly by the distorted structure thereof, but when the thiazole orange derivative or oxazole yellow derivative binds to DNA, the structural distortion is cancelled and fixed, thus allowing strong fluorescence to be emitted. The fluorescence can be detected by, for example, excitation performed using an Ar laser with a wavelength of 488 nm or 514 nm, but the detection method is not limited thereto.

The compound represented by the formula (1), (1b), or (1c) can be used for synthesizing the labeled probe (labeled nucleic acid) of the present invention, for example. That is, the compound can be used as a labeling substance for nucleic acid (nucleic acid labeling reagent). For example, by using the compound represented by the formula (1), (1b), or (1c) as a nucleotide substrate and carrying out a nucleic acid synthesis reaction using a single-stranded nucleic acid as a template, or by chemically synthesizing a single-stranded nucleic acid (for example, a chemical synthesis method such as a phosphoramidite method that is carried out using an automated nucleic acid synthesizer) using a compound represented by the formula (1), (1b), or (1c), a nucleic acid containing at least one molecule of the compound in one molecule can be produced. In this case, the dye moieties $Z^{11}$ and $Z^{12}$ may be each a dye moiety that exhibits fluorescence but also may be a hydrogen atom or a protecting group. When the dye moieties $Z^{11}$ and $Z^{12}$ are, for example, each a dye moiety that exhibits fluorescence, the labeled probe of the present invention can be produced. When each of the dye moieties $Z^{11}$ and $Z^{12}$ is a hydrogen atom or a protecting group, the labeled probe of the present invention can be produced by further substituting the atom or group with a dye moiety that exhibits fluorescence.

The number of compounds represented by the formula (1), (1b), or (1c) that are included in the labeled probe of the present invention is not particularly limited. It is, for example, about 1 to about 100, preferably about 1 to about 20.

The compound or nucleic acid (the labeled probe of the present invention) may have a structure represented by any one of the following formulae (23) to (25), for example. With this configuration, it can be used suitably as a fluorescence probe with dyes introduced therein. However, the compound suitable as a fluorescence probe is not limited thereto.

(23)

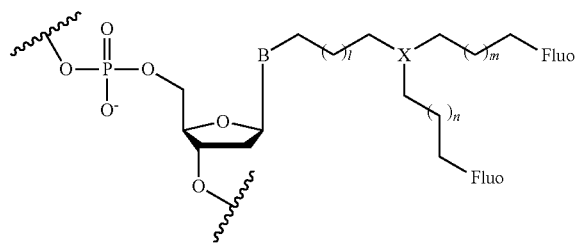

In the formula (23), two dyes (Fluo) are linked to a base B. The site at which the base B binds to a linker is not particularly limited. For example, the base B is linked to the linker at one position selected from the 4-position, the 5-position, and the 6-position of pyrimidine and the 2-position, the 3-position, the 6-position, the 7-position, and the 8-position of purine. The linker has one base linkage site. The linker branches into at least two along the path, and is linked to the dyes at the ends thereof. The method to be employed for linking it to the base or dye may be not only a bond formed by a metal-catalyzed reaction, a ring formation condensation reaction, a Michael addition reaction, or the like to a double bond or a triple bond, but also an amide bond, an ester bond, a disulfide bond, or a bond formed by an imine formation reaction or the like. With respect to the linker, the lengths (l, m, and n) are arbitrary, and it may contain a single bond, a double bond, a triple bond, an amide bond, an ester bond, a disulfide bond, amine, imine, an ether bond, a thioether bond, a thioester bond, or the like. Furthermore, it is preferable that the linker does not interfere with the excitonic effect caused by dimerization. The branched portion (X) is each atom of carbon, silicon, nitrogen, phosphorus, and boron, and protonation (for example, $NH^+$) or oxidation (for instance, $P=O$) may occur. It is preferable that the dye is a dye that exhibits an excitonic effect by dimerization, and the site at which the dye is linked to the linker may be any portion thereof. The formula (23) shows deoxyribonucleotide, which is a partial structure of DNA. However, instead of the deoxyribonucleotide, the nucleic acid skeleton may be ribonucleotide (RNA), or also may be a sugar-modified nucleic acid such as 2'-O-methyl RNA or 2'-fluoro DNA, a phosphoric acid modified nucleic acid such as phosphorothioate nucleic acid, or a functional nucleic acid such as PNA or LNA (BNA).

(24)

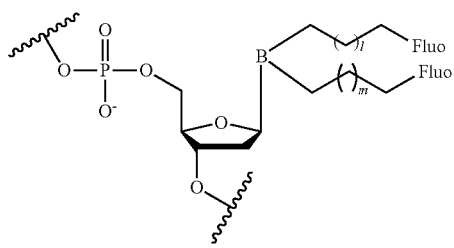

In the formula (24), two dyes (Fluo) are linked to a base B. The sites at which the base B binds to linkers are not particularly limited. For example, the base B is linked to the linkers at two positions selected from the 4-position, the 5-position, and the 6-position of pyrimidine and the 2-position, the 3-position, the 6-position, the 7-position, and the 8-position of purine. Each of the two linkers has one base linkage site, and is linked to the dye at the other end thereof. The method to be employed for linking it to the base or dye may be not only a bond formed by a metal-catalyzed reaction, a ring formation condensation reaction, a Michael addition reaction, or the like to a double bond or a triple bond, but also an amide bond, an ester bond, a disulfide bond, or a bond formed by an imine formation reaction or the like. With respect to the linkers, the lengths (l and m) are arbitrary, and they may contain a single bond, a double bond, a triple bond, an amide bond, an ester bond, a disulfide bond, amine, imine, an ether bond, a thioether bond, a thioester bond, or the like. Furthermore, it is preferable that the linkers do not interfere with the excitonic effect caused by dimerization. It is preferable that the dye is a dye that exhibits an excitonic effect by dimerization, and the site at which the dye is linked to the linker may be any portion thereof. The formula (24) shows deoxyribonucleotide, which is a partial structure of DNA. However, instead of the deoxyribonucleotide, the nucleic acid skeleton may be ribonucleotide (RNA), or also may be a sugar-modified nucleic acid such as 2'-O-methyl RNA or 2'-fluoro DNA, a phosphoric acid modified nucleic acid such as phosphorothioate nucleic acid, or a functional nucleic acid such as PNA or LNA (BNA).

(25)

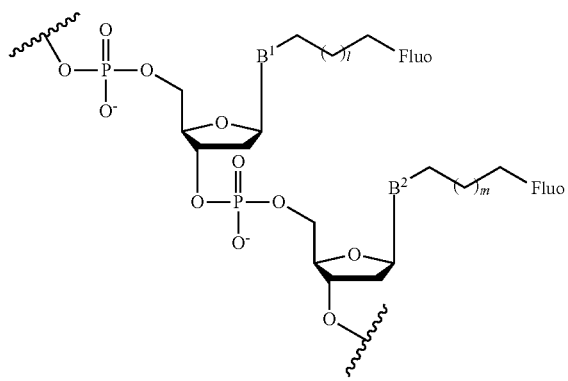

In the formula (25), one dye (Fluo) is linked to each base ($B^1$, $B^2$) of contiguous nucleotides. The site at which each base binds to a linker is not particularly limited. For example, each base is linked to the linker at one position selected from the 4-position, the 5-position, and the 6-position of pyrimidine and the 2-position, the 3-position, the 6-position, the 7-position, and the 8-position of purine. Each of the two linkers has one base linkage site, and is linked to the dye at the other end thereof. The method to be employed for linking them to bases or dyes is not only a bond formed by, for example, a metal-catalyzed reaction, a ring formation condensation reaction, or a Michael addition reaction to a double bond or a triple bond, but also, for example, an amide bond, an ester bond, a disulfide bond, or a bond formed by, for instance, an imine formation reaction. With respect to the linkers, the lengths (l and m) are arbitrary, and they may contain a single bond, a double bond, an amide bond, an ester bond, a disulfide bond, amine, imine, an ether bond, a thioether bond, a thioester bond, or the like. Furthermore, it is preferable that the linkers do not interfere with the excitonic effect caused by dimerization. It is preferable that the dye is a dye that exhibits an excitonic effect by dimerization, and the site at which the dye is linked to the linker may be any portion thereof. The formula (25) shows deoxyribonucleotide, which is a partial structure of DNA. However, instead of the deoxyribonucleotide, the nucleic acid skeleton may be ribonucleotide (RNA), or also may be a sugar-modified nucleic acid such as 2'-O-methyl RNA or 2'-fluoro DNA, a phosphoric acid modified nucleic acid such as phosphorothioate nucleic acid, or a functional nucleic acid such as PNA or LNA (BNA).

When the compound or nucleic acid (for example, the labeled nucleic acid of the present invention) has an isomer such as a tautomer or a stereoisomer (e.g., a geometric isomer, a conformer, or an optical isomer), any of the isomers can be used for the present invention. The salt of the compound or nucleic acid may be an acid addition salt, and also may be a base addition salt. Furthermore, the acid that forms the acid addition salt may be an inorganic acid or an organic acid, and the base that forms the base addition salt may be an inorganic base or an organic base. The inorganic acid is not particularly limited, and examples thereof include sulfuric acid, phosphoric acid, hydrofluoric acid, hydrochloric acid, hydrobromic acid, hydroiodic acid, hypofluorous acid, hypochlorous acid, hypobromous acid, hypoiodous acid, fluorous acid, chlorous acid, bromous acid, iodous acid, fluorine acid, chloric acid, bromic acid, iodic acid, perfluoric acid, perchloric acid, perbromic acid, and periodic acid. The organic acid also is not particularly limited, and examples thereof include p-toluenesulfonic acid, methanesulfonic acid, oxalic acid, p-bromobenzenesulfonic acid, carbonic acid, succinic acid, citric acid, benzoic acid, and acetic acid. The inorganic base is not particularly limited, and examples thereof include ammonium hydroxide, alkali metal hydroxide, alkaline earth metal hydroxide, carbonate, and hydrogen carbonate. More specific examples thereof include sodium hydroxide, potassium hydroxide, potassium carbonate, sodium carbonate, sodium bicarbonate, potassium hydrogencarbonate, calcium hydroxide, and calcium carbonate. The organic base also is not limited, and examples thereof include ethanolamine, triethylamine, and tris(hydroxymethyl)aminomethane. The method of producing salts thereof also is not particularly limited. They can be produced by a method in which, for example, the acids or bases as described above are added as appropriate to the electron donor/receptor binding molecule by a known method. Furthermore, when the substituent or the like has an isomer, any of the isomers can be used. For instance, in the case of a "naphthyl group", it may be a 1-naphthyl group or a 2-naphthyl group.

Furthermore, in the present invention, the alkyl group is not particularly limited. Examples thereof include a methyl group, an ethyl group, an n-propyl group, an isopropyl group, an n-butyl group, an isobutyl group, a sec-butyl group, and a tert-butyl group. The same applies to groups containing alkyl groups in their structures (for example, an alkylamino group and an alkoxyl group). Moreover, the perfluoroalkyl group is not particularly limited. Examples thereof include perfluoroalkyl groups derived from a methyl group, an ethyl group, an n-propyl group, an isopropyl group, an n-butyl group, an isobutyl group, a sec-butyl group, and a tert-butyl group. The same applies to groups containing perfluoroalkyl groups in their structures (for example, a perfluoroalkylsulfonyl group and a perfluoroacyl group). In the present invention, the acyl group is not particularly limited. Examples thereof include a formyl group, an acetyl group, a propionyl group, an isobutyryl group, a valeryl group, an isovaleryl group, a pivaloyl group, a hexanoyl group, a cyclohexanoyl group, a benzoyl group, and an ethoxycarbonyl group. The same applies to groups containing acyl groups in their structures (for example, an acyloxy group and an alkanoyloxy group). In the present invention, the number of carbon atoms in the acyl group includes a carbon atom of a carbonyl group. For example, an alkanoyl group (an acyl group) with a carbon number of 1 indicates a formyl group. Furthermore, in the present invention, "halogen" refers to an arbitrary halogen element, and examples thereof include fluorine, chlorine, bromine, and iodine. In the present invention, the protecting group of an amino group is not particularly limited. Examples thereof include a trifluoroacetyl group, a formyl group, a C1-6 alkyl-carbonyl group (for example, acetyl and ethylcarbonyl), a C1-6 alkyl sulfonyl group, a tert-butyloxycarbonyl group (hereinafter also referred to as "Boc"), a benzyloxycarbonyl group, an allyloxycarbonyl group, a fluorenylmethyloxy carbonyl group, an arylcarbonyl group (for example, phenylcarbonyl and naphthylcarbonyl), an arylsulfonyl group (for example, phenylsulfonyl and naphthylsulfonyl), a C1-6 alkyloxycarbonyl group (for example, methoxycarbonyl and ethoxycarbonyl), a C7-10 aralkylcarbonyl group (for example, benzylcarbonyl), a methyl group, and an aralkyl group (for example, benzyl, diphenylmethyl, and trityl group). These groups may be substituted with, for example, one to three halogen atoms (for example, fluorine, chlorine, or bromine) or nitro groups. Specific examples thereof include a p-nitrobenzyloxycarbonyl group, a p-chlorobenzyloxycarbonyl group, an m-chlorobenzyloxycarbonyl group, and a p-methoxybenzyloxycarbonyl group. In the present invention, the protecting group of a hydroxyl group (including one capable of being deprotected with acid) is not particularly limited. Examples thereof include a dimethoxytrityl group, a monomethoxytrityl group, and a pixyl group.

[Method for Producing Nucleic Acid Probe]

The method for producing the nucleic acid probe of the present invention is not particularly limited. For example, the nucleic acid probe of the present invention may be produced with reference to a known synthesis method (production method) as appropriate. Specifically, the method disclosed in Japanese Patent No. 4370385 may be referenced, for example.

As one illustrative example, the compound represented by the above formula (21) may be produced by a production method including the steps of reacting tris(2-aminoethyl) amine with a compound represented by the following formula (26) after a carboxyl group of the compound is activated; protecting an amino group: and carrying out a reaction for protecting a hydroxyl group present in the compound obtained above with a protecting group and a reaction for adding phosphoric acid or a phosphoramidite group to the hydroxyl group present in the compound obtained above.

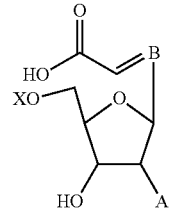

(26)

In the formula (26), A is a hydrogen atom or a hydroxyl group. B is a residue of adenine, guanine, cytosine, thymine, or uracil.

For example, the following production method (synthesis method) can be used for the production of the nucleic acid probe according to the present invention. That is, as an easy DNA labeling method, a method in which an active amino group contained in DNA and an activated carboxyl group in a labeling agent are reacted with each other in a buffer solution has been used widely. This method can be used for the production of both the compound and the nucleic acid of the present invention, and can be used particularly for introduction of a linker or a dye. Examples of the method for introducing an amino group include a method using an amino modifier phosphoramidite commercially available from GLEN RESEARCH.

Each of the dye moieties $Z^{11}$ and $Z^{12}$ can be converted, for example, from a protecting group to a hydrogen atom (i.e., a protecting group is removed), and further the hydrogen atom can be substituted with a dye moiety (dye) having fluorescence. The method for removing the protecting group is not particularly limited, and a known method can be used as appropriate. The method for substituting with a dye moiety (dye) having fluorescence also is not particularly limited. For example, the compound or nucleic acid of the present invention in which $Z^{11}$ and $Z^{12}$ are each a hydrogen atom may be reacted with a fluorescence molecule (dye) as appropriate. For instance, it is preferable that at least one of $Z^{11}$ and $Z^{12}$ is an active amino group, because it allows the compound or nucleic acid of the present invention to react with a fluorescence molecule (dye) more easily. It is more preferable that both of $Z^{11}$ and $Z^{12}$ are active amino groups. The fluorescence molecule (dye) also is not particularly limited, and may be, for example, a compound represented by any one of the formulae (7) to (9) (where $R^{11}$ and $R^{12}$ are both hydrogen atoms or lower alkyl groups, or carboxypolymethylene groups). Furthermore, in the case of the nucleic acid (polynucleotide, polynucleoside, oligonucleotide, or oligonucleoside), the step of removing the protecting group and the step of substituting with the dye moiety (dye) having fluorescence may be carried out either before or after polymerization (nucleic acid synthesis). For example, from the viewpoint of preventing a dye portion from being damaged in the synthesis process, it is preferable that the dye moiety (dye) having fluorescence is introduced after polymerization (nucleic acid synthesis).

As described above, the dye is not particularly limited and any dyes can be used. For example, it is preferably a cyanine dye and particularly preferably thiazole orange. The cyanine dye has a chemical structure in which, for example, two heterocycles having hetero atoms are linked to each other with a methine linker. It is possible to synthesize fluorescent dyes with various excitation/emission wavelengths by, for example, changing the type of the heterocycles or the length of the methine linker, or introducing a substituent into the heterocycles. Furthermore, the introduction of a linker for introducing DNA also is relatively easy. Although thiazole orange hardly emits fluorescence in water, it emits strong fluorescence through an interaction with DNA or RNA. It is considered that, owing to the interaction with the nucleic acid, the interaction between dye molecules is prevented and the rotation around the methine linker located between the two heterocycles of dye molecules is prevented, which leads to an increase in fluorescence intensity. The method of using a thiazole orange dye is well known. It can be used with reference to, for example, H. S. Rye, M. A. Quesada, K. Peck, R. A. Mathies and A. N. Glazer, High-sensitivity two-color detection of double-stranded DNA with a confocal fluorescence gel scanner using ethidium homodimer and thiazole orange, Nucleic Acids Res., 1991, 19, 327-33; and L. G. Lee, C. H. Chen and L. A. Chiu, Thiazole orange: a new dye for reticulocyte analysis, Cytometry, 1986, 7, 508-17.

In the present invention, the basic skeleton of the nucleic acid probe is not particularly limited, as described above. It may be, for example, any of oligonucleotides, modified oligonucleotides, oligonucleosides, modified oligonucleosides, polynucleotides, modified polynucleotides, polynucleosides, modified polynucleosides, DNAs, modified DNAs, RNAs, modified RNAs, LNAs, PNAs (peptide nucleic acids), and other structures. The basic skeleton preferably is DNA, a modified DNA, RNA, or a modified DNA, because the nucleic acid probe can be synthesized easily and also, for example, substitution with a dye (introduction of a dye molecule) can be carried out easily. The method for introducing a dye molecule into LNA or PNA is not particularly limited and a known method can be used as appropriate. Specifically, for example, Analytical Biochemistry 2000, 281, 26-35. Svanvik, N., Westman, G., Wang, D., Kubista, M (2000) Anal Biochem. 281, 26-35. Hrdlicka, P. J., Babu, B. R., Sorensen, M. D., Harrit, N., Wengel, J. (2005) J. Am. Chem. Soc. 127, 13293-13299 can be referred to.

A method for synthesizing a nucleic acid having, as a basic skeleton, an oligonucleotide, a modified oligonucleotide, an oligonucleoside, a modified oligonucleoside, a polynucleotide, a modified polynucleotide, a polynucleoside, a modified polynucleoside, DNA, a modified DNA, RNA, or a modified DNA is well known. For example, it can be synthesized by a so-called phosphoramidite method. A phosphoramidite reagent to serve as a raw material thereof also can be synthesized easily by a known method. When the nucleic acid of the present invention is DNA, particularly a short oligo-DNA, it can be synthesized easily with an automated DNA synthesizer or the like, for example. Furthermore, it is also possible to synthesize a long-chain nucleic acid (DNA) etc. by, for instance, PCR. As described above, the position where DNA and a dye molecule are bonded to each other is not particularly limited, and particularly preferably is the 5-position of thymidine, for example. Triphosphoric acid of a nucleotide derivative with various substituents being extended from the 5-position of thymidine is known to have a relatively high efficiency of introduction carried out with DNA polymerase. Accordingly, the nucleic acid of the present invention can be synthesized easily, for example, not only when it is a short oligo-DNA but also when it is a long-chain DNA.

Particularly, a fluorescence probe (labeled nucleic acid) of the present invention, which is a single-stranded DNA, with, for example, thiazole orange used therein has the following advantages, for example: (1) it can be synthesized easily because it can be prepared merely by introducing, in a buffer solution, a dye into DNA synthesized with an automated DNA synthesizer; and (2) it is also possible to produce a long-chain fluorescence probe by reacting a dye with a long-chain DNA prepared enzymatically. Furthermore, it can be excited with light having a relatively long wavelength around, for example, 500 nm.

In the present invention, for example, two or more kinds of nucleic acid probes of the present invention, which are different from each other in detection wavelength of fluorescent dye moieties, may be used. When the nucleic acid probes of the present invention having different fluorescent dye moieties are used in combination as nucleic acid probes for amplifying two or more kinds of target nucleic acid sequences, respectively, an amplification reaction can be carried out in the same reaction solution and whether or not the respective target nucleic acid sequences are amplified can be detected at detection wavelengths suitable for the respective fluorescent dye moieties.

The chemical modification of the extension-side end (e.g., the 3' end of an atomic group having a deoxyribose skeleton, a ribose skeleton, or a structure derived from either one of them) of the nucleic acid probe (Eprobe) of the present invention can be realized by the following methods, for example. The chemical modification can be carried out, for example, by an ordinary phosphoramidite method with the use of a common automated nucleic acid synthesizer (automated DNA synthesizer). The removal of a protecting group (e.g., a carrier such as a CPG carrier or a styrene polymer) to be performed thereafter also can be carried out, for example, in the same manner as an ordinary phosphoramidite method with the use of a common automated nucleic acid synthesizer.

(1) The 3' end of the Eprobe is chemically modified with an alkyl linker OH group to mask the 3' end OH, whereby an extension reaction caused by polymerase is inhibited. The chemical modification can be achieved by a well-known technique using, for example, a "3'-Spacer C3 CPG" (trade name, GLEN RESEARCH).

(2) The 3' end of the Eprobe is chemically modified with an alkyl linker $NH_2$ group to mask the 3' end OH, whereby an extension reaction caused by polymerase is inhibited. The chemical modification can be achieved by a well-known technique using, for example, a "3'-PT Amino-Modifier C3 CPG" (trade name, GLEN RESEARCH).

(3) To the 3' end of the Eprobe, dideoxynucleotide that does not have OH at its 3' end and thus does not cause an extension reaction by polymerase is introduced. The dideoxynucleotide can be introduced by a well-known technique using, for example, a "3'-2'3' ddC-CPG" (trade name, GLEN RESEARCH).

(4) A phosphodiester linkage is converted to a thiophosphoric acid diester linkage, whereby a digestion reaction that is caused by exonuclease and generates a terminal hydroxyl group is blocked. As a result, an extension reaction caused by polymerase is inhibited.

EXAMPLES

The examples are described below. It is to be noted, however, that the present invention is by no means limited or restricted by the following examples.

A nucleic acid molecule was synthesized as follows. The synthesis of the nucleic acid molecule was carried out in the same manner as the synthesis method described in the examples of Japanese Patent No. 4370385, except that the 3' end thereof was chemically modified.

Intermediate Synthesis Examples 1 to 3

According to the following Scheme 1, compounds 102 and 103 including two active amino groups each protected with a trifluoroacetyl group were synthesized (produced), and further phosphoramidite 104 was synthesized.

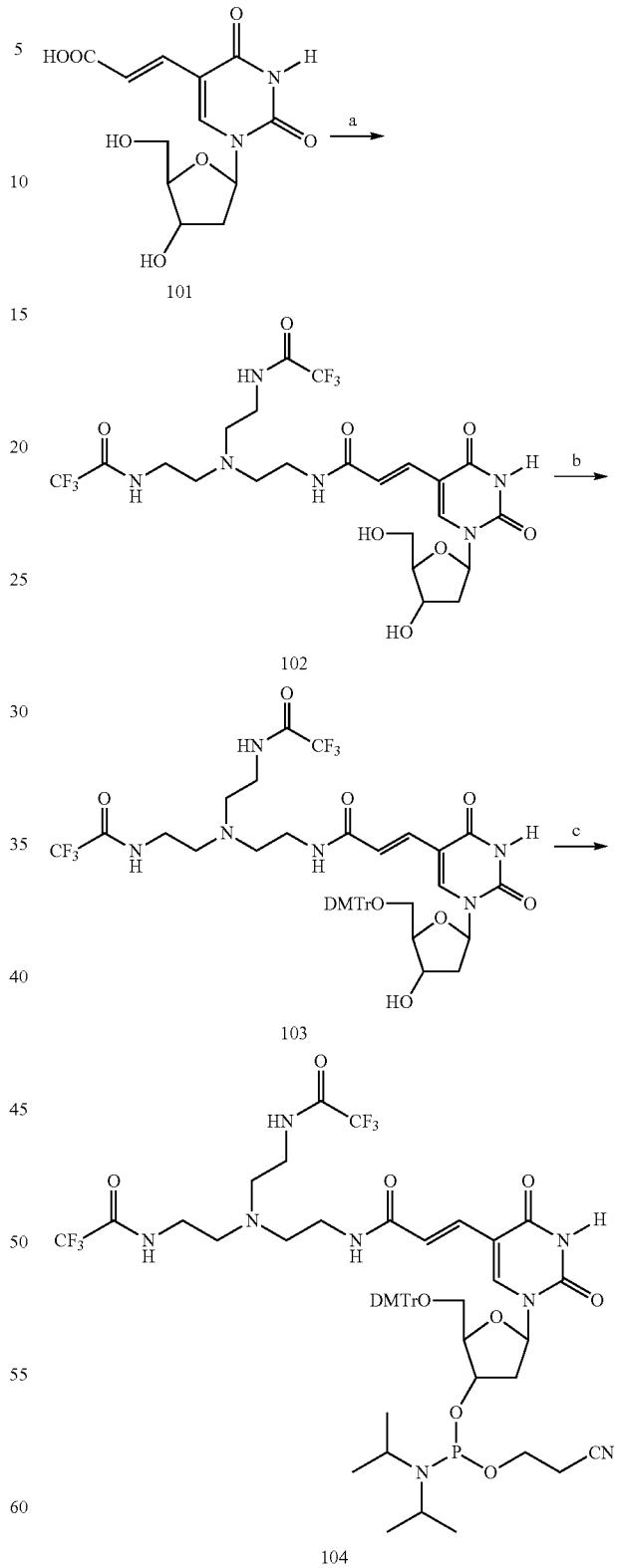

Scheme 1

Reaction reagent and reaction conditions:
(a) (i) N-hydroxysuccinimide, EDC/DMF, (ii) tris(2-aminoethyl)-amine/$CH_3CN$, (iii) $CF_3COOEt$, $Et_3N$;
(b) DMTrCl/pyridine;

(c) 2-cyanoethyl-N,N,N',N'-tetraisopropyl phosphoramidite, 1H-tetrazole/CH₃CN.

Scheme 1 is described below in further detail.

Intermediate Synthesis Example 1: Synthesis of 2-[2-[N,N-bis(2-trifluoroacetamidoethyl)]-aminoethyl]carbamoyl-(E)-vinyl)-2'-deoxyuridine (Compound 102)

The starting material, (E)-5-(2-carboxyvinyl)-2'-deoxyuridine (Compound 101), was synthesized according to Tetrahedron 1987, 43, 20, 4601-4607. That is, first, 71 ml of 1,4-dioxane was added to 430 mg of palladium acetate (II) (FW 224.51) and 1.05 g of triphenylphosphine (FW 262.29), and further 7.1 ml of triethylamine (FW 101.19, d=0.726) was added thereto. This was heated and stirred at 70° C. After the reaction solution changed from reddish brown to blackish brown, 14.2 g of 2'-deoxy-5-iodouridine (FW 354.10) and 7.0 ml of methyl acrylate (FW 86.09, d=0.956) that were suspended in 1,4-dioxane were added thereto. This was heat-refluxed at 125° C. for 1 hour. Thereafter, it was filtered while still hot, the residue was washed with methanol, and then the filtrate was recovered. After the solvent was evaporated from the filtrate under reduced pressure, the product thus obtained was purified with a silica gel column (5-10% methanol/dichloromethane). The solvent of the collected fraction was evaporated under reduced pressure, and the residual white solid was dried under reduced pressure. About 100 ml of ultrapure water was added to the dried solid, and 3.21 g of sodium hydroxide (FW 40.00) was added thereto. This was stirred at 25° C. throughout the night. Thereafter, concentrated hydrochloric acid was added thereto to acidize the solution. The precipitate thus produced was filtered, washed with ultrapure water, and then dried under reduced pressure. Thus, 8.10 g (yield: 68%) of the desired compound (Compound 101) was obtained as white powder. The white powder was confirmed to be the desired compound 101 since the ¹HNMR measured value agreed with the reference value. The ¹³CNMR measured value is described below.

(E)-5-(2-carboxy vinyl)-2'-deoxyuridine (Compound 101)

¹³CNMR (DMSO-d6): δ168.1, 161.8, 149.3, 143.5, 137.5, 117.8, 108.4, 87.6, 84.8, 69.7, 60.8, 40.1.

Next, 1.20 g of (E)-5-(2-carboxy vinyl)-2'-deoxyuridine 101 (with a molecular weight of 298.25), 925 mg of N-hydroxysuccinimide (with a molecular weight of 115.09), and 1.54 g of 1-ethyl-3-(3-dimethylaminopropyl)carbodiimide (with a molecular weight of 191.70) were placed in a recovery flask containing a stirring bar, and 20 ml of DMF was added thereto, which then was stirred at 25° C. for 16 hours. About 1 ml of acetic acid was added thereto and 300 ml of methylene chloride and 100 ml of ultrapure water were added thereto, which then was stirred vigorously. The aqueous layer was removed and further 100 ml of ultrapure water was added, which then was washed twice in the same manner. The precipitate thus produced was filtered, washed with methylene chloride, and then dried under reduced pressure. The solvent was evaporated from the filtrate, methylene chloride was added to the precipitate thus produced, and the precipitate then was recovered in the same manner as described above. The precipitates thus recovered were collected and then suspended in 80 ml of acetonitrile. This was stirred vigorously. Then, 3.0 ml of tris(2-aminoethyl)amine (with a molecular weight of 146.23, d=0.976) was added all at once, which further was stirred at 25° C. for 10 minutes. Thereafter, 4.8 ml of ethyl trifluoroacetate (with a molecular weight of 142.08, d=1.194) was added thereto, and further 5.6 ml of triethylamine (with a molecular weight of 101.19, d=0.726) was added thereto. This was stirred at 25° C. for 3 hours. The solvent was evaporated and the product thus obtained was purified with a silica gel column (5-10% MeOH/CH₂Cl₂). The solvent was evaporated, the product thus obtained was dissolved in a small amount of acetone, and ether then was added thereto. As a result, white precipitate was produced. This was filtered and then washed with ether. Thereafter, this was dried under reduced pressure. Thus, 884 mg (33.5%) of the desired substance (Compound 102) was obtained.

The same synthesis as described above was carried out except for slight changes in the amounts of, for example, raw materials and solvents to be used, the reaction time, and the steps to be taken. As a result, the yield was improved up to 37%. More specifically, 597 mg (2.0 mmol) of (E)-5-(2-carboxy vinyl)-2'-deoxyuridine 101 (with a molecular weight of 298.25), 460 mg (4.0 mmol) of N-hydroxysuccinimide (with a molecular weight of 115.09), and 767 mg (4.0 mmol) of 1-ethyl-3-(3-dimethylaminopropyl)carbodiimide hydrochloride (with a molecular weight of 191.70) were placed in a recovery flask containing a stirring bar. Thereafter, 5.0 ml of DMF was added thereto, which was stirred at 25° C. for 3 hours. About 0.5 ml of acetic acid was added thereto, and 100 ml of methylene chloride and 100 ml of ultrapure water further were added thereto. This was stirred vigorously. The precipitate thus produced was filtered, washed with water, and then dried under reduced pressure throughout the night. The resultant white residue was suspended in 50 ml of acetonitrile, which was stirred vigorously. Then, 3.0 ml (20 mmol) of tris(2-aminoethyl) amine (with a molecular weight of 146.23, d=0.976) was added thereto all at once, which further was stirred at 25° C. for 10 minutes. Thereafter, 4.8 ml of ethyl trifluoroacetate (with a molecular weight of 142.08, d=1.194) was added and further 5.6 ml (40 mmol) of triethylamine (with a molecular weight of 101.19, d=0.726) was added thereto, which was then stirred at 25° C. for 16 hours. The solvent was evaporated and the product thus obtained was purified with a silica gel column (5-10% MeOH/CH₂Cl₂). The solvent was evaporated, the product thus obtained was dissolved in a small amount of acetone, and ether was then added thereto. As a result, white precipitate was produced. This was filtered and then washed with ether. Thereafter, this was dried under reduced pressure. Thus, 453 mg (37%) of the desired substance (Compound 102) was obtained as white powder. The instrumental analytical values of Compound 102 are indicated below.

2-[2-[N,N-bis(2-trifluoroacetamidoethyl)]-aminoethyl]carbamoyl-(E)-vinyl)-2'-deoxyuridine (Compound 102)

¹HNMR (CD₃OD): δ8.35 (s, 1H), 7.22 (d, J=15.6 Hz, 1H), 7.04 (d, J=15.6 Hz, 1H), 6.26 (t, J=6.6 Hz, 1H), 4.44-4.41 (m, 1H), 3.96-3.94 (m, 1H), 3.84 (dd, J=12.2, 2.9 Hz, 1H), 3.76 (dd, J=12.2, 3.4 Hz, 1H), 3.37-3.30 (m, 6H), 2.72-2.66 (m, 6H), 2.38-2.23 (m, 2H). ¹³CNMR (CD₃OD): δ169.3, 163.7, 159.1 (q, J=36.4 Hz), 151.2, 143.8, 134.3, 122.0, 117.5 (q, J=286 Hz), 110.9, 89.1, 87.0, 71.9, 62.5, 54.4, 53.9, 41.7, 38.9, 38.7. HRMS (ESI) calcd for C₂₂H₂₉F₆N₆O₈ ([M+H]⁺) 619.1951, found 619.1943.

Intermediate Synthesis Example 2: Synthesis of 5'-O-dimethoxytrityl-(2-[2-[N,N-bis(2-trifluoroacetamidoethyl)]-aminoethyl]carbamoyl-(E)-vinyl)-2'-deoxyuridine (5'-O-DMTr-(2-[2-[N,N-bis(2-trifluoroacetamidoethyl)]-aminoethyl]carbamoyl-(E)-vinyl)-2'-deoxyuridine, Compound 103)

The 5'-hydroxyl group of Compound 102 was protected with a DMTr group. Thus, Compound 103 was obtained.

More specifically, first, 618 mg of Compound 102 (with a molecular weight of 618.48) and 373 mg of 4,4'-dimethoxytritylchloride (with a molecular weight of 338.83) were placed in a recovery flask containing a stirring bar. Then, 10 ml of pyridine was added thereto, which was stirred at 25° C. for 16 hours. A small amount of water was added thereto, the solvent was evaporated, and the product thus obtained was purified with a silica gel column (2-4% MeOH, 1% Et$_3$N/CH$_2$Cl$_2$). The solvent of the fraction containing the desired compound 103 was evaporated. Thus, 735.2 mg (79.8%) of the desired substance (Compound 103) was obtained. The instrumental analytical values of Compound 103 are indicated below.

5'-O-DMTr-(2-[2-[N,N-bis(2-trifluoroacetamido-ethyl)]-aminoethyl]carbamoyl-(E)-vinyl)-2'-deoxyuridine (Compound 103)

$^1$HNMR (CD$_3$OD): δ7.91 (s, 1H), 7.39-7.11 (m, 9H), 7.02 (d, J=15.6 Hz, 1H), 6.93 (d, J=15.6 Hz, 1H), 6.80-6.78 (m, 4H), 6.17 (t, J=6.6 Hz, 1H), 4.38-4.35 (m, 1H), 4.06-4.04 (m, 1H), 3.68 (s, 6H), 3.32-3.22 (m, 8H), 2.66-2.55 (m, 6H), 2.40 (ddd, J=13.7, 5.9, 2.9 Hz, 1H), 2.33-2.26 (m, 1H). $^{13}$CNMR (CD$_3$OD): δ168.9, 163.7, 160.1, 159.1 (q, J=36.9 Hz), 151.0, 146.1, 143.0, 137.0, 136.9, 134.1, 131.24, 131.16, 129.2, 128.9, 128.0, 122.5, 117.5 (q, J=286.7 Hz), 114.2, 110.9, 88.1, 87.9, 87.6, 72.6, 65.0, 55.7, 54.2, 53.9, 41.7, 38.9, 38.6. HRMS (ESI) calcd for C$_{43}$H$_{47}$F$_6$N$_{10}$ ([M+H]$^+$) 921.3258, found 921.3265.

Intermediate Synthesis Example 3: Synthesis of 5'-O-dimethoxytrityl-(2-[2-[N,N-bis(2-trifluoroacetamidoethyl)]-aminoethyl]carbamoyl-(E)-vinyl)-2'-deoxyuridine, 3'-[(2-cyanoethyl)-(N,N-diisopropyl)]-phosphoramidite (5'-O-DMTr-(2-[2-[N,N-bis(2-trifluoroacetamidoethyl)]-aminoethyl]carbamoyl-(E)-vinyl)-2'-deoxyuridine, 3'-[(2-cyanoethyl)-(N,N-diisopropyl)]-phosphoramidite, Compound 104)

First, 188 mg (0.20 mmol) of Compound 103 (with a molecular weight of 920.85) was allowed to form an azeotrope with CH$_3$CN, and 28.6 mg (0.40 mmol) of 1H-tetrazole (with a molecular weight of 70.05) was added thereto. This was vacuum-dried with a vacuum pump overnight. Then, 5.1 ml of CH$_3$CN was added thereto to dissolve the reagent therein, which then was stirred. Thereafter, 194 µl (0.60 mmol) of 2-cyanoethyl-N,N,N',N'-tetraisopropylphosphoramidite (with a molecular weight of 301.41, d=0.949) then was added thereto all at once, which was stirred at 25° C. for 2 hours. After that, a mixture of 50 ml of ethyl acetate and 50 ml of saturated sodium bicarbonate water was added thereto, and liquid separation was carried out. The organic layer thus obtained was washed with saturated saline, and then, it was dried with magnesium sulfate. The magnesium sulfate was removed by filtration, and the solvent was then evaporated. The crude product obtained by this liquid separation was allowed to form an azeotrope with CH$_3$CN. Thereafter, assuming that the product (Compound 104) was obtained with a yield of 100%, 0.1 M of CH$_3$CN solution was prepared and was used for DNA synthesis. The fact that Compound 104 had been obtained was confirmed from $^{31}$PNMR (CDCl$_3$) and HRMS (ESI) of the crude product. The values thereof are indicated below.

Compound 104

$^{31}$PNMR (CDCl$_3$) δ 149.686, 149.430; HRMS (ESI) calcd for C$_{52}$H$_{64}$F$_6$N$_8$O$_{11}$P ([M+H]$^+$) 1121.4336, found 1121.4342.

Intermediate Synthesis Example 4: DNA Oligomer Synthesis

Scheme 2

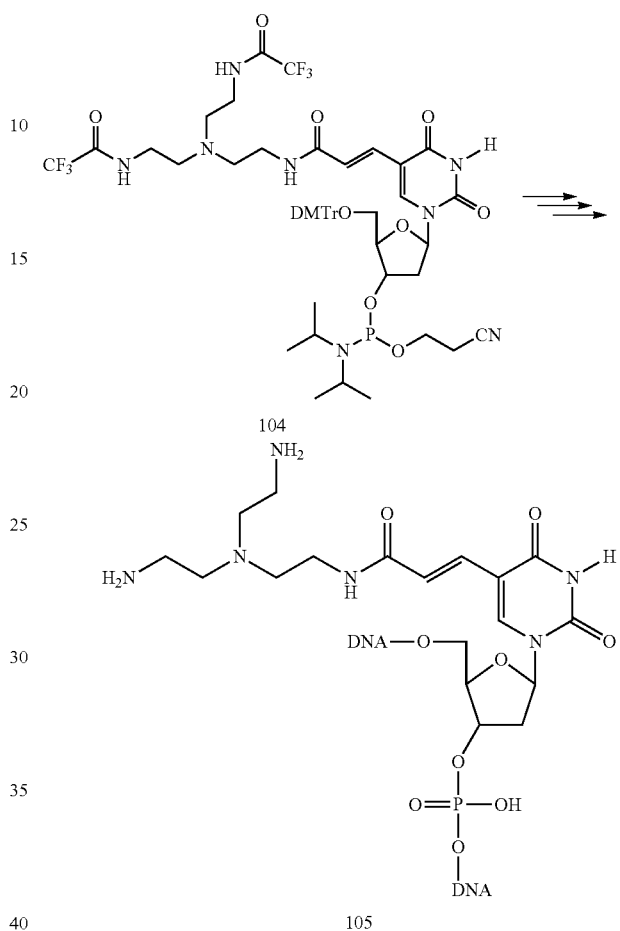

The synthesis of oligo-DNA with an automated DNA synthesizer using Compound 104 was carried out by an ordinary phosphoramidite method (DMTr OFF) on a 1 µmol scale. Thus, each of DNA oligomers with sequences shown in the examples described below was synthesized. Deprotection was carried out with concentrated ammonia water (28 mass %) at 55° C. for 16 hours. Ammonia was volatilized with a speed vac, and the product thus obtained was passed through a 0.45-µm filter. Thereafter, DNA oligomer cut out therefrom was analyzed by reversed-phase HPLC, and the peak that had appeared after about 10.5 minutes was purified (CHEMCOBOND 5-ODS-H (trade name); 10×150 mm, 3 ml/min, 5-30% CH$_3$CN/50 mM TEAA buffer pH 7 (20 minutes), detected at 260 nm). The molecular weight of the product thus purified was measured with a MALDI TOF mass spectrometer in its negative mode. As a result, it was confirmed that the product had a desired sequence.

In order to determine the concentration of each DNA thus synthesized, each purified DNA was digested completely at 25° C. for 16 hours using calf intestinal alkaline phosphatase (50 U/ml), snake venom phosphodiesterase (0.15 U/ml), and P1 nuclease (50 U/ml). The digested liquids thus obtained were analyzed by HPLC with a CHEMCOBOND 5-ODS-H (trade name) column (4.6×150 mm). In this analysis, 0.1 M TEAA (pH 7.0) was used as a developer, and the flow rate was set to 1.0 ml/min. The concentration of the synthesized DNA was determined based on comparison with the peak area of the standard solution containing dA, dC, dG, and dT, the concentration of each of which was 0.1 mM. Furthermore, the synthesized DNA was identified also with a MALDI TOF mass spectrum.
Nucleic Acid Molecule Synthesis Example:
Synthesis of Nucleic Acid Molecule Having, in One Molecule, Structures Derived from Thiazole Orange in Two Places
Scheme 4
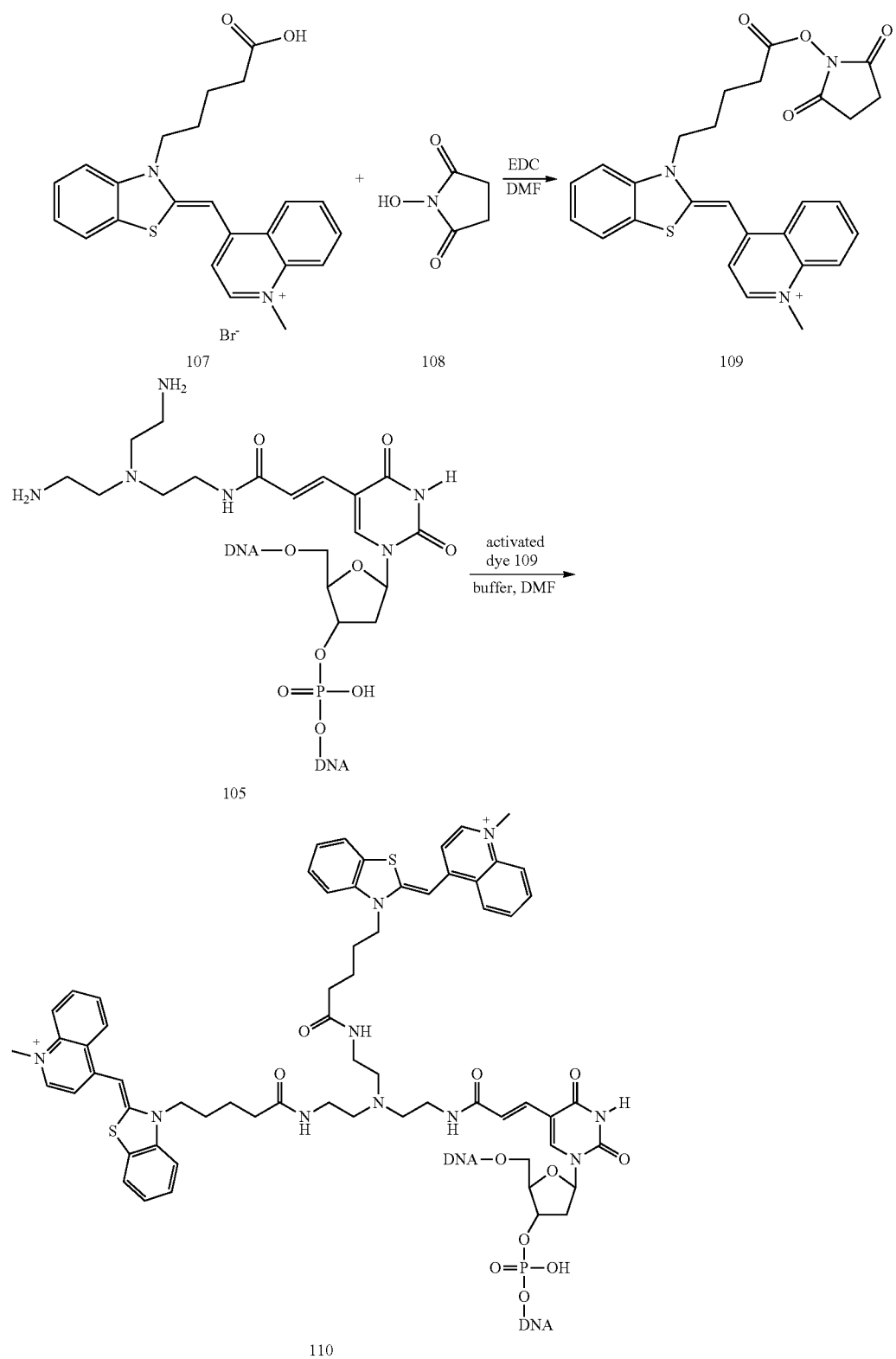

As shown in Scheme 4, DNA oligomer (oligonucleotide) 110 was synthesized that has, in one molecule, structures derived from thiazole orange in two places. A more specific description thereof is given below.

The thiazole orange derivative 107 was synthesized as indicated below in Scheme 5 with reference to Organic Letters 2000, 6, 517-519.

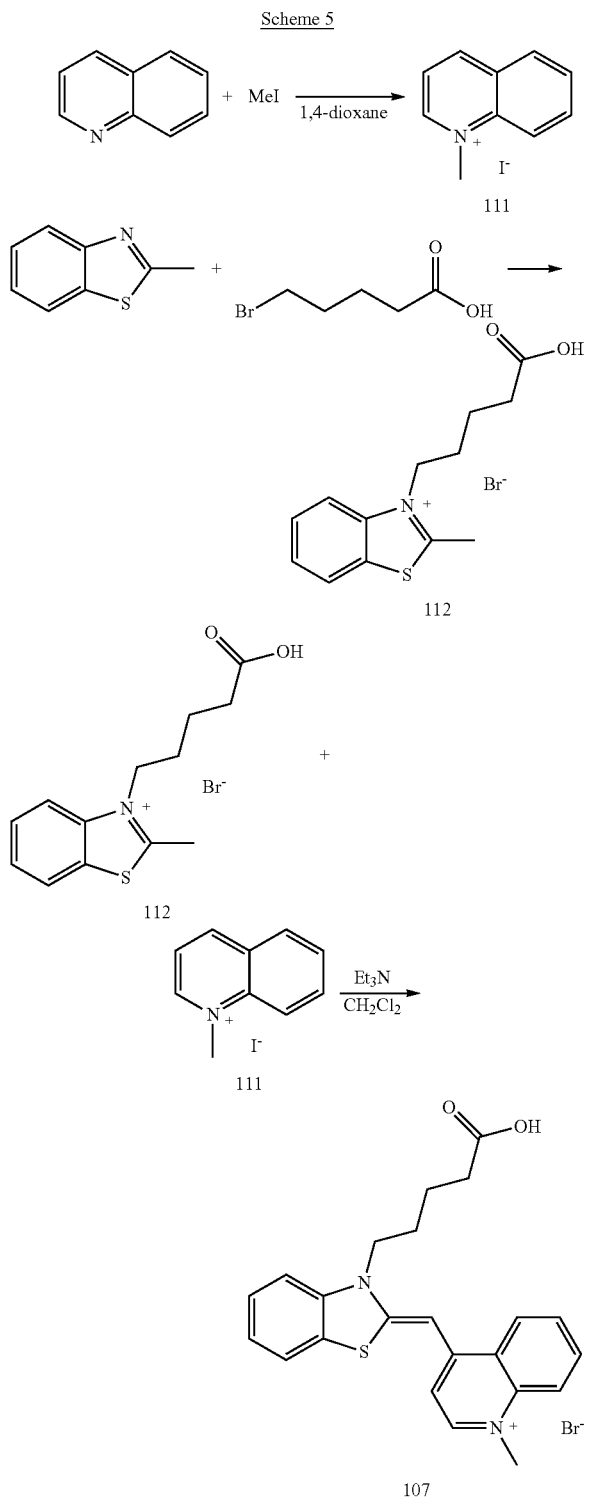

(1) Synthesis of N-Methylquinolinium Iodide (Compound 111)

First, N-methylquinolinium iodide (Compound 111) was synthesized according to the description in the aforementioned reference. Specifically, 2.4 ml of quinoline and 4 ml of methyl iodide were added to 42 ml of anhydrous dioxane, which was stirred at 150° C. for 1 hour. Thereafter, it was filtered and a precipitate was collected. Then, the precipitate was washed with ether and petroleum ether, and then dried. Thus, N-methylquinolinium iodide (Compound 111) was obtained.

(2) Synthesis of 3-(4-carboxybutyl)-2-methylbenzothiazolium bromide (Compound 112)

8 ml of 2-methylbenzothiazole (FW 149.21, d=1.173) and 9.4 g of 5-bromovaleric acid (5-bromopentanoic acid) (FW 181.03) were stirred at 110° C. for 16 hours. The crude product was cooled to room temperature and a solid thus produced was suspended in 20 ml of methanol, and 40 ml of ether further was added thereto. The precipitate thus produced was filtered and then washed with dioxane until the odor of 2-methylbenzothiazole was removed. This further was washed with ether and then dried under reduced pressure. Thus 9.8 g of white powder was obtained. Thereafter, $^1$HNMR of this white powder was measured. As a result, it was found to be a mixture of 3-(4-carboxybutyl)-2-methylbenzothiazolium bromide (Compound 112), which was the desired substance whose 2-position had been alkylated, and 3-(4-carboxybutyl)-benzothiazolium bromide whose 2-position had not been alkylated. The peak ratio of proton was non-alkylated:alkylated=10:3. This crude product was used for the next reaction without further being treated.

(3) Synthesis of 1-methyl-4-[{3-(4-carboxybutyl)-2 (3H)-benzothiazolylidene}methyl]quinolinium bromide (Compound 107)

2.18 g of the crude product containing 3-(4-carboxybutyl)-2-methylbenzothiazolium bromide (Compound 112) obtained in (2) above and 700 mg of N-methylquinolinium iodide (Compound 111) (FW 271.10) were stirred in 10 ml of methylene chloride at 25° C. for 2 hours in the presence of 3.6 ml of triethylamine (FW 101.19, d=0.726). Thereafter, 50 ml of ether was added thereto and a precipitate produced thereby was filtered, washed with ether, and then dried under reduced pressure. The precipitate was suspended in 50 ml of ultrapure water, which was filtered, washed with ultrapure water, and then dried under reduced pressure. Further, the precipitate was suspended in 50 ml of acetonitrile, which was filtered, washed with acetonitrile, and then dried under reduced pressure. Thus, 307.5 mg of red powder was obtained (yield: 25.3%). This red powder was confirmed to be the desired substance (Compound 107) through a comparison in $^1$HNMR spectrum with the reference value.

Moreover, it was also possible to synthesize 3-(4-carboxybutyl)-2-methylbenzothiazolium bromide (Compound 112) and 1-methyl-4-[{3-(4-carboxybutyl)-2(3H)-benzothiazolylidene}methyl]quinolinium bromide (Compound 107) in the following manner. More specifically, first, 11.7 ml (92 mmol) of 2-methylbenzothiazole (FW 149.21, d=1.173) and 13.7 g (76 mmol) of 5-bromovaleric acid (5-bromopentanoic acid) (FW 181.03) were stirred at 150° C. for 1 hour. The crude product was cooled to room temperature and the solid thus produced was suspended in 50 ml of methanol. Further, 200 ml of ether was added thereto. The precipitate thus produced was filtered, washed with ether, and then dried under reduced pressure. Thus, 19.2 g of light purple powder was obtained. This powder was a mixture of the desired compound 112 (3-(4-carboxybutyl)-2-methylbenzothiazolium bromide) and 2-methylbenzothiazolium bromide. This mixture was subjected to $^1$HNMR (in DMSO-d6) measurement, and the yield of the desired compound 112 was calculated to be 9.82 g (14 mmol, 32%) from the peak area ratio between the peak at 8.5 ppm (derived from the desired compound 112) and the peak at 8.0 ppm (derived from the 2-methylbenzothiazolium bromide). This mixture (crude product) was used for the next reaction without being purified. In the same manner as described above except that the 5-bromovaleric acid (5-bromopentanoic acid) was replaced with 4-bromobutyric acid (4-bromobutanoic acid), 3-(4-carboxypropyl)-2-methylbenzothiazolium bromide with a linker (a polymethylene chain linked to a carboxyl group) having a carbon number n of 3 was synthesized, which was obtained with a yield of 4%. Furthermore, in the same manner as described above except that 5-bromovaleric acid (5-bromopentanoic acid) was replaced with 6-bromohexanoic acid, 3-(4-carboxypentyl)-2-methylbenzothiazolium bromide with a linker (a polymethylene chain linked to a carboxyl group) having a carbon number n of 5 was synthesized, which was obtained with a yield of 35%. Still further, in the same manner as described above except that 5-bromovaleric acid (5-bromopentanoic acid) was replaced with 7-bromoheptanoic acid, 3-(4-carboxypropyl)-2-methylbenzothiazolium bromide with a linker (a polymethylene chain linked to a carboxyl group) having a carbon number n of 6 was synthesized, which was obtained with a yield of 22%.

Next, 1.36 g (5.0 mmol) of N-methylquinolinium iodide (Compound 111) (FW 271.10), 7.0 ml (50 mmol) of triethylamine (FW 101.19, d=0.726), and 100 ml of methylene chloride were added to 3.24 g of the mixture (crude product) containing Compound 112 (3-(4-carboxybutyl)-2-methylbenzothiazolium bromide) and 2-methylbenzothiazolium bromide. As a result, a transparent solution was obtained. This solution was stirred at 25° C. for 16 hours. Thereafter, the solvent was evaporated under reduced pressure. Acetone (200 ml) then was added to the residue and the precipitate obtained thereby was filtered, which then was washed with acetone. The residue thus obtained was dried under reduced pressure, and the red residue obtained after drying was washed with distilled water (50 ml). This further was filtered, which was washed with distilled water and then dried under reduced pressure. Thus, the desired substance (Compound 107) was obtained as red powder (654 mg, 1.39 mmol, 28%). This red powder was confirmed to be the desired substance (Compound 107) through a comparison in $^1$HNMR spectrum with the reference value. Peak values from $^1$HNMR and $^{13}$CNMR (DMSO-d6) and the measured values of HRMS (ESI) are indicated below.

Compound 107

$^1$HNMR (DMSO-d6): δ 8.74 (d, J=8.3 Hz, 1H), 8.51 (d, J=7.3 Hz, 1H), 7.94-7.89 (m, 3H), 7.74-7.70 (m, 1H), 7.65 (d, J=8.3 Hz, 1H), 7.55-7.51 (m, 1H), 7.36-7.32 (m, 1H), 7.21 (d, J=7.3 Hz, 1H), 6.83 (s, 1H), 4.47 (t, J=7.1 Hz, 2H), 4.07 (s, 3H), 2.22 (t, J=6.6 Hz, 1H), 1.77-1.63 (m, 4H); $^{13}$CNMR (DMSO-d6, 60° C.) δ 174.6, 158.8, 148.4, 144.5, 139.5, 137.6, 132.7, 127.9, 126.8, 125.5, 124.1, 123.7, 123.6, 122.4, 117.5, 112.6, 107.6, 87.4, 45.6, 42.0, 35.5, 26.2, 22.3; HRMS (ESI) calcd for $C_{23}H_{23}N_2O_2S$ ([M.Br]$^+$) 391.1480, found 391.1475.

4-((3-(3-carboxypropyl)benzo[d]thiazole-2 (3H)-ylidene)methyl)-1-methylquinoliniumbromide with a linker (a polymethylene chain linked to a carboxyl group) having a carbon number n of 3 was synthesized from the mixture of 3-(4-carboxypropyl)-2-methylbenzothiazolium bromide and 2-methylbenzothiazolium bromide by the same method as that used for Compound 107, which was obtained with a yield of 43%. The instrumental analytical values are indicated below.

4-((3-(3-carboxypropyl)benzo[d]thiazole-2 (3H)-ylidene)methyl)-1-methylquinoliniumbromide $^1$HNMR (DMSO-d6) δ 8.85 (d, J=8.3 Hz, 1H), 8.59 (d, J=7.3 Hz, 1H), 8.02.7.93 (m, 3H), 7.78.7.70 (m, 2H), 7.61.7.57 (m, 1H), 7.42.7.38 (m, 1H), 7.31 (d, J=6.8 Hz, 1H), 7.04 (s, 1H), 4.47 (t, J=8.1 Hz, 2H), 4.13 (s, 3H), 2.52.2.48 (m, 2H), 1.99.1.92 (m, 2H); $^{13}$CNMR (DMSO-d6, 60° C.) δ 174.3, 158.9, 148.6, 144.5, 139.5, 137.7, 132.7, 127.9, 126.7, 125.6, 124.1, 124.0, 123.7, 122.5, 117.5, 112.5, 107.6, 87.7, 45.6, 42.0, 31.6, 22.4; HRMS (ESI) calcd for $C_{22}H_{21}N_2O_2S$ ([M.Br]$^+$) 377.1324, found 377.1316.

Furthermore, 4-((3-(3-carboxypentyl)benzo[d]thiazole-2 (3H)-ylidene)methyl)-1-methylquinoliniumbromide with a linker (a polymethylene chain linked to a carboxyl group) having a carbon number n of 5 was synthesized from the mixture of 3-(4-carboxypentyl)-2-methylbenzothiazolium bromide and 2-methylbenzothiazolium bromide by the same method as that used for Compound 107, which was obtained with a yield of 26%. The instrumental analytical values are indicated below.

4-((3-(3-carboxypentyl)benzo[d]thiazole-2(3H)-ylidene)methyl)-1-methylquinoliniumbromide $^1$HNMR (DMSO-d6) δ 8.70 (d, J=8.3 Hz, 1H), 8.61 (d, J=6.8 Hz, 1H), 8.05.8.00 (m, 3H), 7.80.7.73 (m, 2H), 7.60.7.56 (m, 1H), 7.41.7.35 (m, 2H), 6.89 (s, 1H), 4.59 (t, J=7.3 Hz, 2H), 4.16 (s, 3H), 2.19 (t, J=7.3 Hz, 1H), 1.82.1.75 (m, 2H), 1.62.1.43 (m, 4H); $^{13}$CNMR (DMSO-d6, 60° C.) δ 174.5, 159.0, 148.6, 144.7, 139.7, 137.8, 132.9, 127.9, 126.9, 125.2, 124.2, 123.8, 123.6, 122.6, 117.8, 112.6, 107.7, 87.4, 45.6, 42.1, 36.0, 26.3, 25.9, 24.9; HRMS (ESI) calcd for $C_{24}H_{25}N_2O_2S$ ([M.Br]$^+$) 405.1637, found 405.1632.

Furthermore, 4-((3-(3-carboxyhexyl)benzo[d]thiazole-2 (3H)-ylidene)methyl)-1-methylquinoliniumbromide with a linker (a polymethylene chain linked to a carboxyl group) having a carbon number n of 6 was synthesized from the mixture of 3-(4-carboxyhexyl)-2-methylbenzothiazolium bromide and 2-methylbenzothiazolium bromide by the same method as that used for Compound 107, which was obtained with a yield of 22%. The instrumental analytical values are indicated below.

4-((3-(3-carboxyhexyl)benzo[d]thiazole-2(3H)-ylidene)methyl)-1-methylquinoliniumbromide $^1$HNMR (DMSO-d6) δ 8.72 (d, J=8.3 Hz, 1H), 8.62 (d, J=6.8 Hz, 1H), 8.07.8.01 (m, 3H), 7.81.7.75 (m, 2H), 7.62.7.58 (m, 1H), 7.42.7.38 (m, 2H), 6.92 (s, 1H), 4.61 (t, J=7.3 Hz, 2H), 4.17 (s, 3H), 2.18 (t, J=7.3 Hz, 1H), 1.82.1.75 (m, 2H), 1.51.1.32 (m, 6H); $^{13}$CNMR (DMSO-d6, 60° C.) δ 174.0, 159.1, 148.6, 144.7, 139.8, 137.8, 132.9, 127.9, 126.8, 125.0, 124.2, 123.8, 123.6, 122.6, 118.0, 112.7, 107.8, 87.4, 45.5, 42.1, 33.4, 27.9, 26.4, 25.5, 24.1; HRMS (ESI) calcd for $C_{25}H_{27}N_2O_2S$ ($[M.Br]^+$) 419.1793, found 419.1788.

(4) Synthesis of N-Hydroxysuccinimidyl Ester 109

9.4 mg (20 μmol) of 1-methyl-4-[{3-(4-carboxybutyl)-2 (3H)-benzothiazolylidene}methyl]quinolinium bromide (Compound 107) (FW 471.41), 4.6 mg (40 μmol) of N-hydroxysuccinimide (Compound 108) (FW 115.09), and 7.6 mg (40 μmol) of EDC (1-ethyl-3-(3-dimethylaminopropyl) carbodiimide hydrochloride) (FW 191.70) were stirred in 1 ml of DMF at 25° C. for 16 hours. Thus, N-hydroxysuccinimidyl ester (Compound 109) was obtained, in which the carboxy group of the dye (Compound 107) had been activated. This reaction product was not purified, and the reaction solution (20 mM of a dye) was used for the reaction with oligomeric DNA (oligonucleotide) 105 without further being treated.

Furthermore, 4-((3-(4-(succinimidyloxy)-4-oxobutyl) benzo[d]thiazole-2(3H)-ylidene)methyl)-1-methylquinolinium bromide with a linker (a polymethylene chain) having a carbon number n of 3 was synthesized by the same method as that used for Compound 109 except that a compound with a linker (a polymethylene chain) having a different carbon number was used as a raw material instead of Compound 107. Moreover, 4-((3-(4-(succinimidyloxy)-4-oxohexyl)benzo[d]thiazole-2(3H)-ylidene)methyl)-1-methylquinolinium bromide with a linker (a polymethylene chain) having a carbon number n of 5 and 4-((3-(4-(succinimidyloxy)-4-oxoheptyl)benzo[d]thiazole-2(3H)-ylidene) methyl)-1-methylquinolinium bromide with a linker (a polymethylene chain) having a carbon number n of 6 were synthesized in the same manner.

(5) Synthesis of DNA Oligomer (Oligonucleotide) 110 Modified with Two Molecules of Thiazole Orange A DNA oligomer (oligonucleotide) 105 having two active amino groups was synthesized by an ordinary method with the use of an automated DNA synthesizer in the same manner as in Intermediate Synthesis Example 4. Next, this DNA oligomer (oligonucleotide) 105 was reacted with N-hydroxysuccinimidyl ester (Compound 109), thus synthesizing DNA oligomer (oligonucleotide) 110, which was a nucleic acid molecule having, in one molecule, structures derived from thiazole orange in two places. More specifically, first, 30 μl of the DNA oligomer 105 (with a strand concentration of 320 μM), 10 μl of $Na_2CO_3/NaHCO_3$ buffer (1 M, pH 9.0), and 60 μl of $H_2O$ were mixed together. Thereafter, 100 μl of DMF solution (20 mM) of N-hydroxysuccinimidyl ester (Compound 109) was added thereto and mixed well. This was allowed to stand still at 25° C. for 16 hours. Thereafter, 800 μl of $H_2O$ was added thereto, which then was passed through a 0.45-μm filter and purified by reversed-phase HPLC (CHEMCOBOND 5-ODS-H 10×150 mm, 3 ml/min, 5-30% $CH_3CN$/50 mM TEAA buffer (20 minutes), detected at 260 nm).

Example 1

The 3' end of the DNA oligomer 110 (Eprobe), which was the nucleic acid molecule synthesized in the above nucleic acid molecule synthesis example, was chemically modified with a phosphate group or a C3 linker OH group (3-hydroxypropyl group) so as to prevent an extension reaction. Thus, nucleic acid probes (Eprobes) of the present invention were synthesized. The chemical modification with the C3 linker OH group was achieved using a "3'-Spacer C3 CPG" (trade name, GLEN RESEARCH). The chemical modification and the elimination of a protecting group (CPG carrier) were carried out under the same conditions as in an ordinary phosphoramidite method using an automated DNA synthesizer. The chemically-modified DNA oligomers were subjected to a PCR reaction. As a result, the DNA oligomer chemically-modified with the phosphate group was extended slightly in the PCR reaction, whereas substantially no extension was observed in the DNA oligomer chemically-modified with the C3 linker OH group (see FIG. 2).

The PCR reaction was carried out by a real-time PCR system "CFX96" (Bio-Rad) using a reaction reagent "AmpliTaqGold Master Mix" (Life Technologies) in a specified manner (template DNA-containing sample: 5 μl, primer solutions (10 μM): 2.5 μl each, Eprobe solution (2 μM): 2.5 μl, the total amount of reaction solution: 25 μl). As primer sequences, 5'-CCTCACAGCAGGGTCTTCTC-3' (SEQ ID NO: 1) and 5'-CCTGGTGTCAGGAAAATGCT-3' (SEQ ID NO: 2) were used. As a template, plasmid DNA (SEQ ID NO: 3) that encodes an EGFR Exon21 sequence was used. As a mutant, an L858R mutant (SEQ ID NO: 4) was used.

(SEQ ID NO: 3)
5'-TGAACATGACCCTGAATTCGGATGCAGAGCTTCTTCCCATGATGATC

TGTCCCTCACAGCAGGGTCTTCTCTGTTTCAGGGCATGAACTACTTGGAG

GACCGTCGCTTGGTGCACCGCGACCTGGCAGCCAGGAACGTACTGGTG

AAAACACCGCAGCATGTCAAGATCACAGATTTTGGGCTGGCCAAACTGC

TGGGTGCGGAAGAGAAAGAATACCATGCAGAAGGAGGCAAAGTAAGGA

GGTGGCTTTAGGTCAGCCAGCATTTTCCTGACACCAGGGACCAGGCTGC

CTTCCCACT-3'

(SEQ ID NO: 4)
5'-AGCCTGGCATGAACATGACCCTGAATTCGGATGCAGAGCTTCTTCCC

ATGATGATCTGTCCCTCACAGCAGGGTCTTCTCTGTTTCAGGGCATGAAC

TACTTGGAGGACCGTCGCTTGGTGCACCGCGACCTGGCAGCCAGGAACG

TACTGGTGAAAACACCGCAGCATGTCAAGATCACAGATTTTGGGCGGGC

CAAACTGCTGGGTGCGGAAGAGAAAGAATACCATGCAGAAGGAGGCAA

AGTAAGGAGGTGGCTTTAGGTCAGCCAGCATTTTCCTGACACCAGGGAC

CAGGCTGCCTTCCCACTAGCTGTATTGTTTAACACATGCAGGGGAGGAT

GCTCTCCAG-3'

As the Eprobe for detection, 5'-AGATTTTGGGCZGGC-CAAACTG-X-3' (SEQ ID NO: 5) was used (Z denotes dT to which dye labels that exhibit an excitonic effect had been introduced, and X denotes the phosphate group or the C3 linker OH group). The PCR conditions were as follows. An initial thermal denaturation at 95° C. for 10 minutes was conducted, and then a cycle of a thermal denaturation at 95° C. for 12 seconds, annealing at 56° C. for 30 seconds, and an extension reaction at 72° C. for 12 seconds was repeated to a total of 50 cycles. Melting curve analysis of an amplification product with respect to fluorescence intensity was carried out using CFX Manager Software version 1.6. The melting curve analysis was carried out with a temperature increase from 30° C. to 95° C. at 0.1° C./second.

Figure 2:
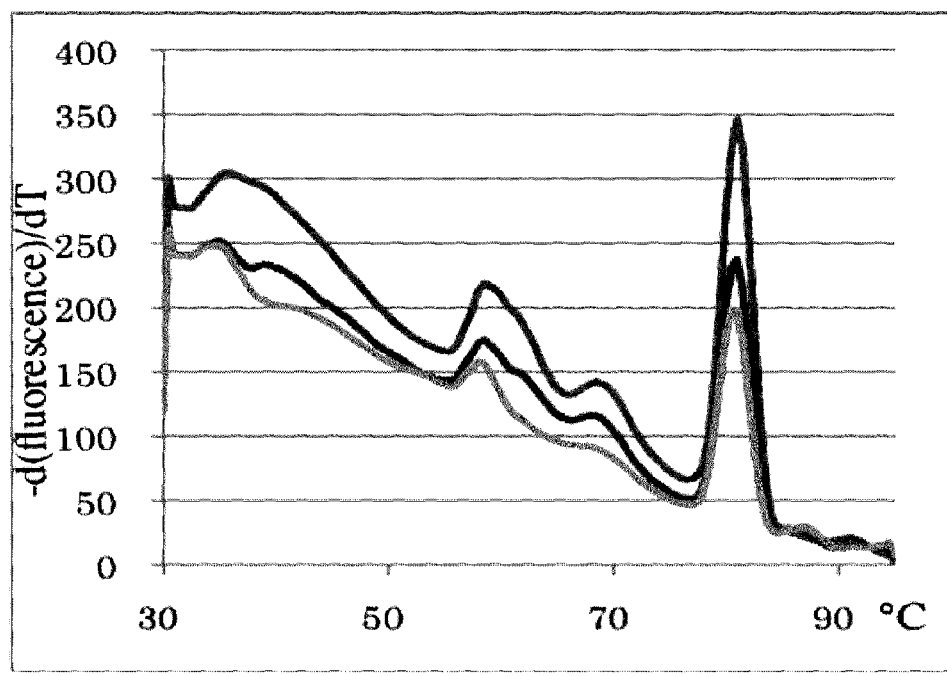
FIG. 2 shows graphs illustrating the influence on the melting curve analysis due to the difference in modification of the 3' end in an Example.
Figure 2:
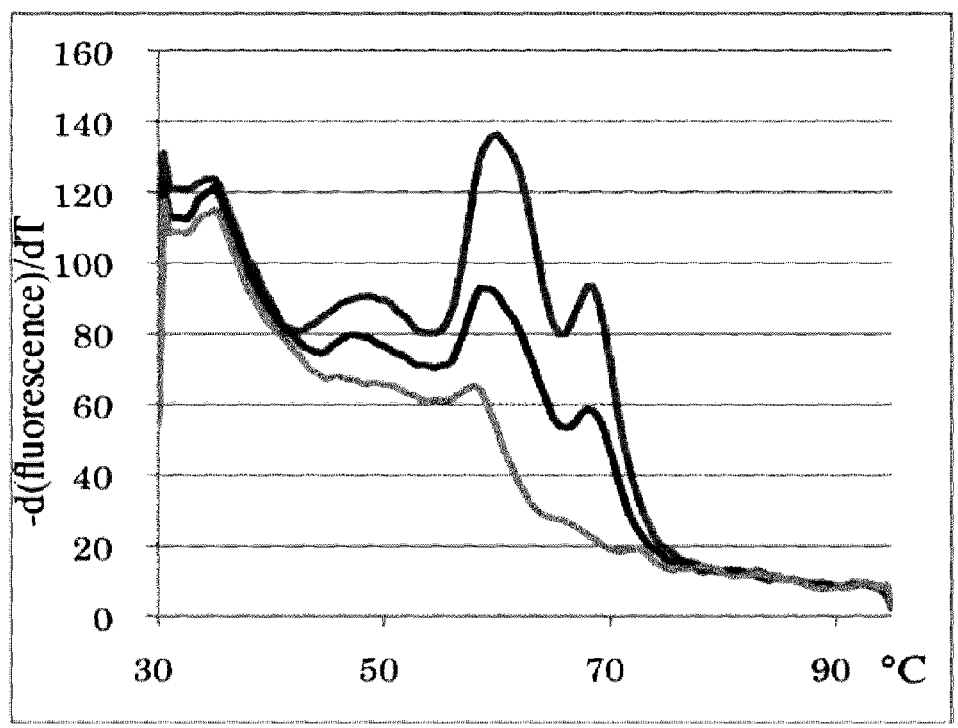

FIG. 2 shows graphs illustrating the influence on the melting curve analysis due to the difference in modification of the 3' end in the above-described measurement. In FIG. 2, the horizontal axis indicates the temperature (° C.), and the vertical axis indicates –dF/dT, i.e., the differential value of the fluorescence value (the numerical value obtained by differentiating the fluorescence value with respect to the temperature). The upper graph shows the melting curve analysis in the case of the chemical modification with the phosphoric acid, and a peak was observed at around 80° C., which is considered to result from extension caused by elimination of the phosphoric acid. The lower graph shows the melting curve analysis in the case of the chemical modification with the linker OH group, and a peak was not observed at around 80° C. The curves represent, from the top, the results obtained when the template DNA-containing sample contained: 100% wild-type DNA; 50% wild-type DNA and 50% mutant-type DNA; and 100% mutant-type DNA.

Example 2

The 3' end of the nucleic acid molecule (DNA oligomer 110) was chemically modified in the same manner as in Example 1 to synthesize each nucleic acid probe of the present invention (Eprobe). As a control, a nucleic acid probe (Eprobe) in which the 3' end of the nucleic acid molecule (DNA oligomer 110) was not chemically modified also was used. The detection efficiency was checked with varying a position labeled with exciton in each Eprobe and a position of a mutation site relative to the labeled position. As a result, it was demonstrated that the detection sensitivity was improved by designing the Eprobe so as to satisfy the following conditions.
(1) In the Eprobe, the label is added to a base at a position at least three bases inward from each end of the Eprobe (see FIGS. 3 and 4).
(2) In a target sequence having a mutation (mismatch), the mismatch is at a position at least four bases inward from each end of a region to which the Eprobe hybridizes.
(3) When it is required to make a difference in detection peak intensity between a sequence that does not have the mutation in the target sequence (full match) and a sequence that has the mutation in the target sequence (mismatch) by the labeled position in the Eprobe, the mutation site is at a position three or fewer bases away from a base to be paired with the labeled base in the Eprobe, and when it is required not to make the difference, the mutation site is at a position at least four bases away from the base to be paired with the labeled base in the Eprobe (see FIGS. 5 and 6).

Figure 3:
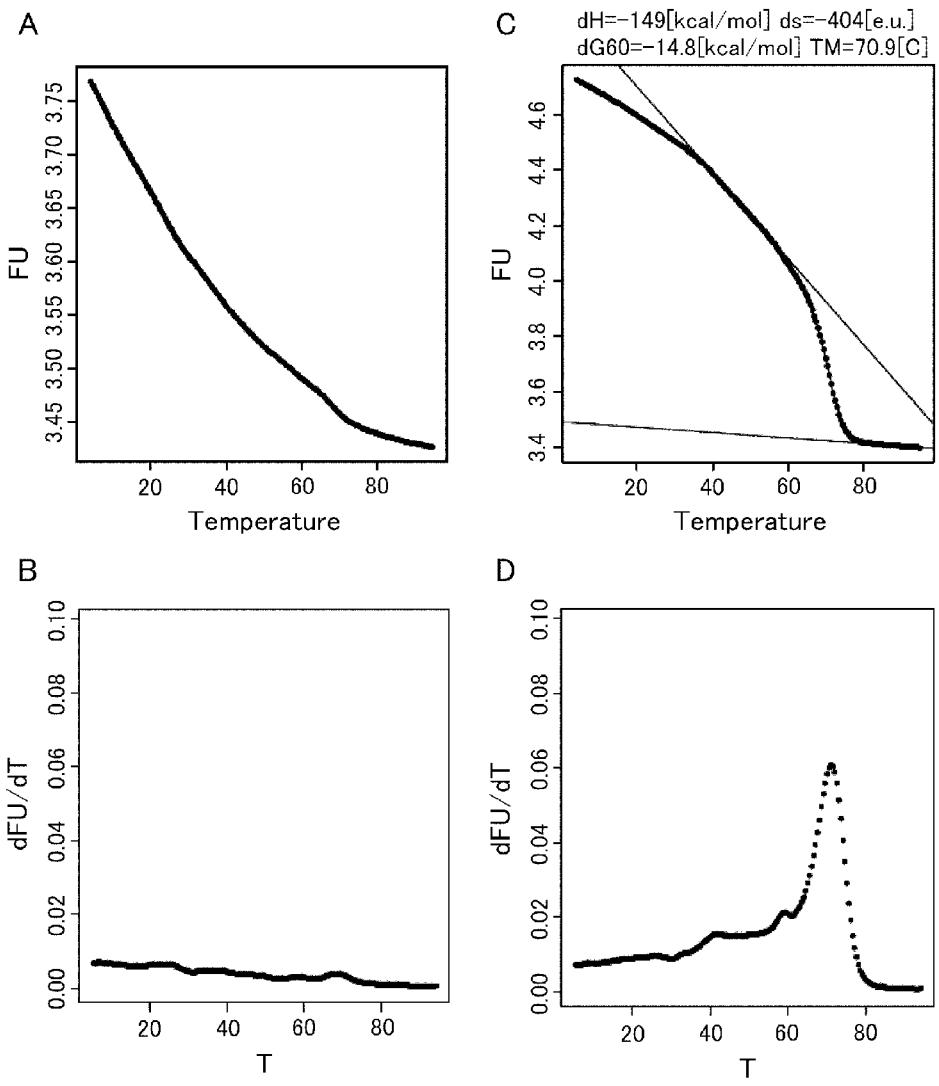
FIG. 3 shows the melting curves (A, C) for the Eprobe and the sequence complementary thereto and the primary differential curves (B, D) of the melting curves in an Example.
Figure 4:
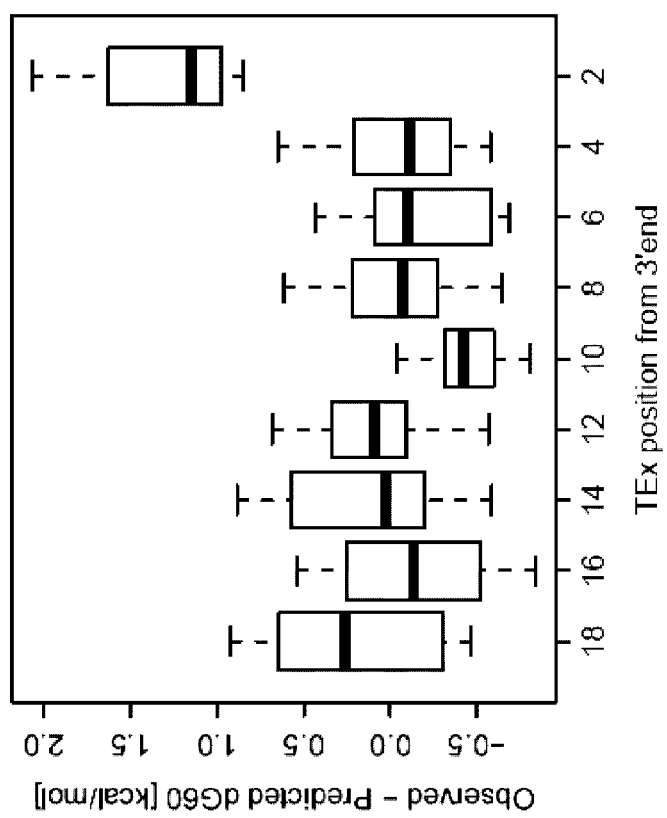
FIG. 4 shows graphs illustrating the relationship between the position of the dye and the "binding free energy actual measured value–predicted value" in an Example.
Figure 4:
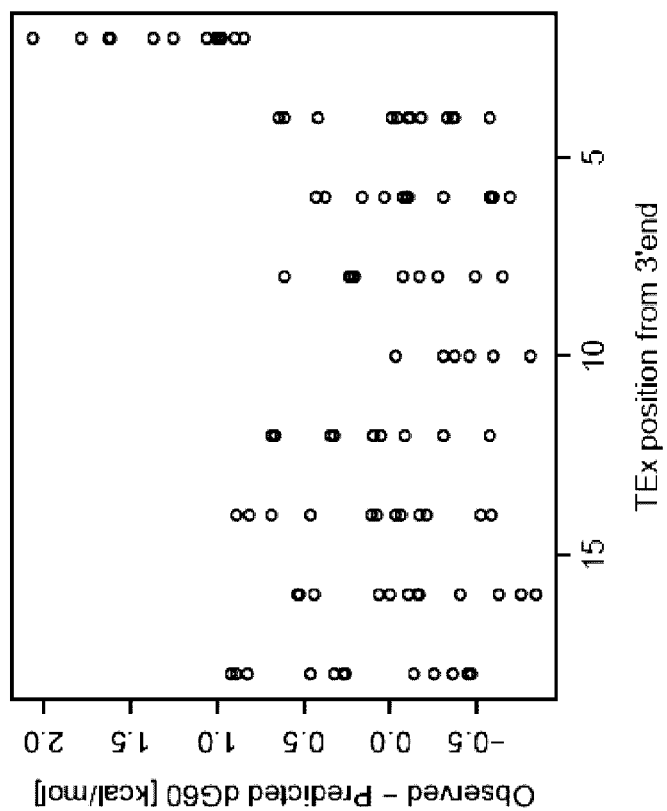
Figure 6:
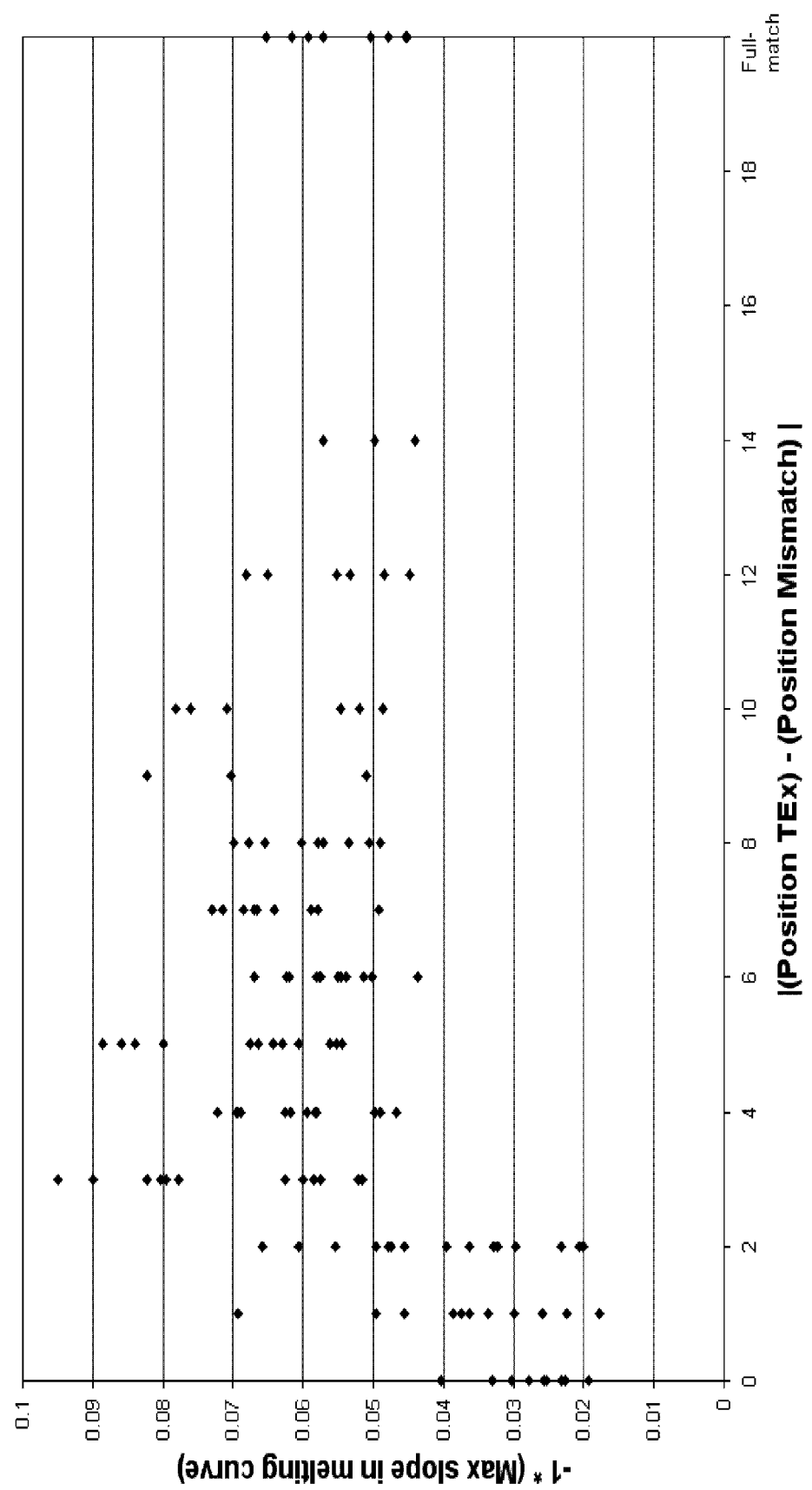
FIG. 6 shows a graph illustrating the relationship between the distance (the number of bases) between the dye and the mismatch and the height of a peak in the melting curve in an Example.

In the experiments of FIGS. 3, 4, and 6, the following sequences were used. Each of ten Eprobes was designed by introducing dye labels into a base of a 20-mer sequence. In the thus-obtained ten Eprobes, the position of the labeled base corresponds to every other base (Z denotes dT in which dye labels that exhibit an excitonic effect had been introduced).

```
                                   (SEQ ID NO: 6)
20-mer. EX20 5'-ZGTGTATCTTTCTCTTTCTC-3'

(SEQ ID NO: 7)
20-mer. EX18 5'-TGZGTATCTTTCTCTTTCTC-3'

(SEQ ID NO: 8)
20-mer. EX16 5'-TGTGZATCTTTCTCTTTCTC-3'

(SEQ ID NO: 9)
20-mer. EX14 5'-TGTGTAZCTTTCTCTTTCTC-3'

(SEQ ID NO: 10)
20-mer. EX12 5'-TGTGTATCZTTCTCTTTCTC-3'

(SEQ ID NO: 11)
20-mer. EX10 5'-TGTGTATCTTZCTCTTTCTC-3'

(SEQ ID NO: 12)
20-mer. EX8  5'-TGTGTATCTTTCZCTTTCTC-3'

(SEQ ID NO: 13)
20-mer. EX6  5'-TGTGTATCTTTCTCZTTCTC-3'

(SEQ ID NO: 14)
20-mer. EX4  5'-TGTGTATCTTTCTCTTZCTC-3'

(SEQ ID NO: 15)
20-mer. EX2  5'-TGTGTATCTTTCTCTTTCZC-3'
```

As DNA sequences complementary to the Eprobes, a full match sequence and sequences each having a mismatch at the 4th base, 9th base, 11th base, or 16th base from the 5' end were designed.

```
Full match
EX_TM.rdm_885.full
                                   (SEQ ID NO: 16)
5'-GAGAAAGAGAAAGATACACA-3'

Mismatch
4th base: C, G, T
EX_TM.rdm_885.m4_c
                                   (SEQ ID NO: 17)
5'-GAGcAAGAGAAAGATACACA-3'

EX_TM.rdm_885.m4_g
                                   (SEQ ID NO: 18)
5'-GAGgAAGAGAAAGATACACA-3'

EX_TM.rdm_885.m4_t
                                   (SEQ ID NO: 19)
5'-GAGtAAGAGAAAGATACACA-3'

9th base: C, A, T
EX_TM.rdm_885.m9_a
                                   (SEQ ID NO: 20)
5'-GAGAAAGAaAAAGATACACA-3'

EX_TM.rdm_885.m9_c
                                   (SEQ ID NO: 21)
5'-GAGAAAGAcAAAGATACACA-3'

EX_TM.rdm_885.m9_t
                                   (SEQ ID NO: 22)
5'-GAGAAAGAtAAAGATACACA-3'

10th base: C, G, T
EX_TM.rdm_885.m10_c
                                   (SEQ ID NO: 23)
5'-GAGAAAGAGcAAGATACACA-3'

EX_TM.rdm_885.m10_g
                                   (SEQ ID NO: 24)
5'-GAGAAAGAGgAAGATACACA-3'

EX_TM.rdm_885.m10_t
                                   (SEQ ID NO: 25)
5'-GAGAAAGAGtAAGATACACA-3'

11th base: C, G, T
EX_TM.rdm_885.m11_c
```

-continued

```
                                         (SEQ ID NO: 26)
5'-GAGAAAGAGAcAGATACACA-3'

EX_TM.rdm_885.m11_g
                                         (SEQ ID NO: 27)
5'-GAGAAAGAGAgAGATACACA-3'

EX_TM.rdm_885.m11_t
                                         (SEQ ID NO: 28)
5'-GAGAAAGAGAtAGATACACA-3'

16th base: C, G, T
EX_TM.rdm_885.m16_c
                                         (SEQ ID NO: 29)
5'-GAGAAAGAGAAAGATcCACA-3'

EX_TM.rdm_885.m16_g
                                         (SEQ ID NO: 30)
5'-GAGAAAGAGAAAGATgCACA-3'

EX_TM.rdm_885.m16_t
                                         (SEQ ID NO: 31)
5'-GAGAAAGAGAAAGATtCACA-3'
```

Figure 11:
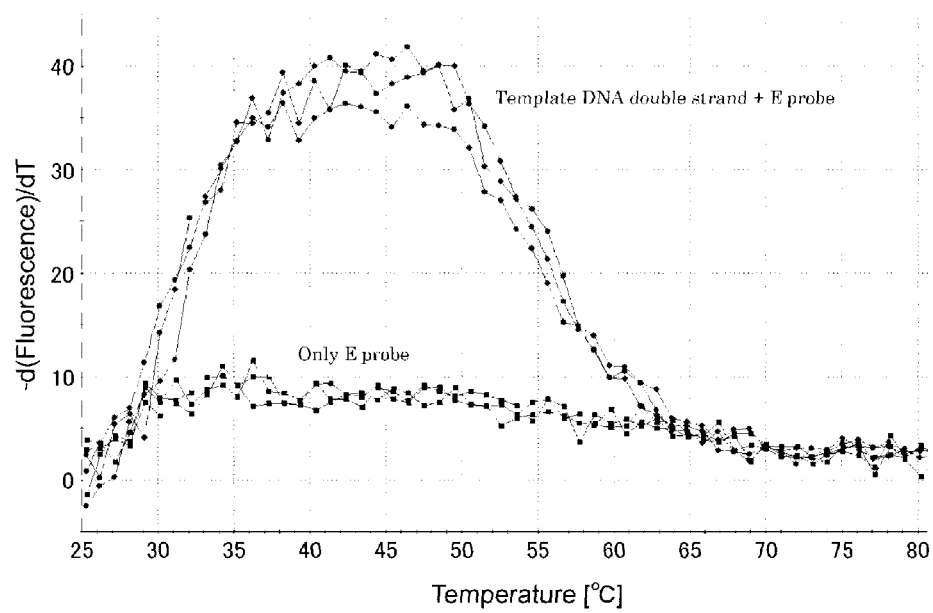
FIG. 11 shows a graph illustrating the melting curve analysis result for confirming the detection of a target sequence in a double-stranded nucleic acid by the Eprobe in an Example.

Melting curve experiments of FIGS. 3, 4, 6, and 11 were carried out under the following conditions. The fluorescence intensity and the melting curves of the nucleic acid double-strands were analyzed using the Bio-Rad Laboratories CFX96. In FIGS. 3, 4, and 6, 1 µM of each Eprobe and DNA complementary to the Eprobe were dissolved in a buffer containing 980 mM NaCl, 10 mM Na$_2$HPO$_4$, and 0.1 mM Na$_2$EDTA. In FIG. 11, 1 µM of the Eprobe was dissolved in the buffer. Thus, each measurement sample was obtained. The sample was heated to 95° C., kept at this temperature for 5 minutes, and then cooled to room temperature. The melting curve analysis was carried out by measuring emitted light at 530 nm using excitation light at 510 nm while keeping the sample at 4° C. for 30 seconds and then heating it from 4° C. to 95° C. at 0.1° C./second. After the measurement, the logarithms of the obtained fluorescence values were taken, and each melting curve was analyzed. In this reaction, an extension reaction of DNA did not occur because no DNA polymerase was used in the reaction. On this account, the 3' end of each Eprobe used in these experiments was not chemically modified with a phosphate group or a C3 linker OH group. Also in the case where Eprobes with their 3' ends being chemically modified with a phosphate group or a C3 linker OH group were used, the same results were obtained.

The reaction conditions in FIG. 5 were as follows. PCR was carried out by a real-time PCR system "LightCycler system" (Roche Diagnostics) using a reaction reagent "AmpliTaqGold Master Mix" (Life Technologies) in a specified manner (template DNA-containing sample: 5 µl, primer solutions (10 µM): 2.5 µl each, Eprobe solution (2 µM): 2.5 µl, the total amount of reaction solution: 25 µl). As primer sequences, 5'-TTATAAGGCCTGCTGAAAAT-GACTGAA-3' (SEQ ID NO: 32) and 5'-TGAATTAGCTG-TATCGTCAAGGCACT-3' (SEQ ID NO: 33) were used, and as a template, plasmid DNA (SEQ ID NO: 34) that encodes a Kras sequence was used. As a mutant, a G12D mutant (SEQ ID NO: 35) having a mutation in codon 12 (hereinafter referred to as "Codon 12 G12D mutant") was used.

```
                                         (SEQ ID NO: 34)
5'-CAAACTTACAGGGGCTCGACGAGCTAGGTTCCCGGACACGACAAAG

GCGGCCGCGGGAATTGCGTTGGAGGAGTTTGTAAATAAAGTACAGTTCA

TTACGATACACGTCTGCAGTCAACTGGAATTTTCATGATTGAATTTTGT
```

-continued

```
AAGGTATTTTGAAATAATTTTTCATATAAAGGTGAGTTTGTATTAAAAG

GTACTGGTGGAGTATTTGATAGTGTATTAACCTTATGTGTGACATGTTC

TAATATAGTCACATTTTCATTATTTTTATTATAAGGCCTGCTGAAAATG

ACTGAATATAAACTTGTGGTAGTTGGAGCTGGTGGCGTAGGCAAGAGTG

CCTTGACGATACAGCTAATTCAGAATCATTTTGTGGACGAATATGATCC

AACAATAGAGGTAAATCTTGTTTTAATATGCATATTACTGGTGCAGGAC

CATTCTTTGATACAGATAAAGGTTTCTCTGACCATTTTCATGAGTACTT

ATTACAAGATAATTATGCTGAAAGTTAAGTTATCTGAAATGTACCTTGG

GTTTCAAGTTATATGTAACCATTAATATGGGAACTTTACTTTCCTTGGG

AGTATGAATCACTAGTGAATTCGCGGCCGCCTGCAGGTCGACCATATGG

GAGAGCTCCAACGCGTTGGATGCATAGCTTGAGTATTCTATAGTGTCAC

CTAAATAGCTTGGCGTAATCATGGTCATAGCTGTTTCCTGTGTGAAATT

GTTATCCGCTCACATTTCCACACACATACGAGCCGGAAGCATAAAGTGT

AAAGCCTGGGGTGCTCAATGAGTGAGCTAACTCACATTATTGCGTTGCG

CTCACTGCC-3'
```

```
                                         (SEQ ID NO: 35)
5'-ACCTCTAGGGACGCCGAATCACGCGGTATCCCGGCCGCCATAGAGA

CGGCCGCGGGAATTCGATTGGAGGAGTTTGTAAATAAAGTACAGTTCAT

TACGATACACGTCTGCAGTCAACTGGAATTTTCATGATTGAATTTTGTA

AGGTATTTTGAAATAATTTTTCATATAAAGGTGAGTTTGTATTAAAAGG

TACTGGTGGAGTATTTGATAGTGTATTAACCTTATGTGTGACATGTTCT

AATATAGTCACATTTTCATTATTTTTATTATAAGGCCTGCTGAAAATGA

CTGAATATAAACTTGTGGTAGTTGGAGCTGATGGCGTAGGCAAGAGTGC

CTTGACGATACAGCTAATTCAGAATCATTTTGTGGACGAATATGATCCA

ACAATAGAGGTAAATCTTGTTTTAATATGCATATTACTGGTGCAGGACC

ATTCTTTGATACAGATAAAGGTTTCTCTGACCATTTTCATGAGTACTTA

TTACAAGATAATTATGCTGAAAGTTAAGTTATCTGAAATGTACCTTGGG

TTTCAAGTTATATGTAACCATTAATATGGGAACTTTACTTTCCTTGGGA

GTATGAATCACTAGTGAATTCGCGGCCGCCTGCAGGTCGACCATATGGG

AGAGCTCCAACGCGTTGGATGCATAGCTTGAGTATTCTATAGTGTCAC

CTAAATAGCTTGGGCGTAATCATGGTCATAGC-3'
```

As an Eprobe, 5'-AGCTGGTGGCGZAG-3' (SEQ ID NO: 36) was used in a system in which a mutation was also to be detected, and 5'-AGCTG<u>G</u>ZGGCGTAG-3' (SEQ ID NO: 37) was used in a system in which mutation detection was to be suppressed (Z denotes dT to which dye labels that exhibit an excitonic effect had been introduced, and <u>G</u> denotes a mutation site). The PCR conditions were as follows. An initial thermal denaturation at 95° C. for 10 minutes was conducted, and then a cycle of a thermal denaturation at 95° C. for 12 seconds, annealing at 56° C. for 30 seconds, and an extension reaction at 72° C. for 12 seconds was repeated to a total of 50 cycles. The fluorescence intensity and the melting curves of the amplification products were analyzed using LightCycler Software version 1.2.0.169. The melting curve analysis was carried out with a temperature increase from 37° C. to 95° C. at 0.1° C./second.

FIG. 3 shows the melting curves (A, C) for the Eprobe and the sequence complementary thereto and the primary differential curves (B, D) of the melting curves in the above-described measurement. In the case where the label was present at the 5' end (A, B), melting curves could not be drawn on the basis of fluorescence, and thus, the labeling at the end is inappropriate. In the case where the label was present at the third base from the 5' end (C, D), melting curves could be drawn on the basis of fluorescence. In FIGS. 3A and 3C, the horizontal axis indicates the temperature (° C.), and the vertical axis indicates the fluorescence intensity value. In FIGS. 3B and 3D, the horizontal axis indicates the temperature (° C.), and the vertical axis indicates the value obtained by differentiating the fluorescence intensity with respect to the temperature.

FIG. 4 shows graphs illustrating the relationship between the position of the dye and the "binding free energy actual measured value—predicted value" in the above-described measurement. In the analysis, a full match sequence or a sequence with a mismatch at a position at least three bases away from the position of the dye was used. The predicted value was calculated using parameters (Table 1 below) of the nearest neighbor method, which were determined using a 11-mer sequence having dyes at its center. In FIG. 4, the horizontal axis indicates the distance (the number of bases) from the 3' end to the base to which the dyes (fluorescent dye moieties) had been added, and the vertical axis indicates the "binding free energy actual measured value—predicted value". As shown in FIG. 4, in the case where the dyes were present at the second base from the 3' end, the measured stability of the double strand was lower than the predicted value.

TABLE 1

Parameters of nearest neighbor method used for prediction

| nearest neighbor (5' to 3'/5' to 3') | ΔΔH° [kcal mol⁻¹] | ΔΔS° [cal mol⁻¹ K⁻¹] | ΔΔG°₃₇ [kcal mol⁻¹] | ΔΔG°₆₀ [kcal mol⁻¹] |
|---|---|---|---|---|
| full-match | | | | |
| AT$^E$/AT | −1.8 ± 1.7 | −1.2 ± 3.0 | −1.4 ± 0.4 | −1.3 ± 0.2 |
| CT$^E$/AG | 1.4 ± 1.3 | 8.4 ± 2.3 | −1.2 ± 0.4 | −1.6 ± 0.3 |
| GT$^E$/AC | 10.6 ± 1.3 | 34.6 ± 2.3 | −0.5 ± 0.4 | −1.4 ± 0.2 |
| TT$^E$/AA | −0.1 ± 1.4 | 3.9 ± 2.3 | −1.3 ± 0.4 | −1.4 ± 0.2 |
| T$^E$A/TA | −5.4 ± 1.6 | −11.0 ± 2.7 | −1.8 ± 0.4 | −1.5 ± 0.2 |
| T$^E$C/GA | 6.7 ± 1.5 | 24.4 ± 2.5 | −0.9 ± 0.4 | −1.3 ± 0.3 |
| T$^E$G/CA | 8.3 ± 1.3 | 29.0 ± 2.2 | −0.8 ± 0.4 | −1.2 ± 0.2 |
| T$^E$T/AA | 0.4 ± 1.3 | 3.4 ± 2.3 | −0.9 ± 0.4 | −1.7 ± 0.2 |
| mis-match T$^E$•C | | | | |
| AT$^E$/CT | 5.4 ± 1.3 | 19.1 ± 2.3 | −0.7 ± 0.2 | −0.9 ± 0.2 |
| CT$^E$/CG | −8.1 ± 1.3 | −21.2 ± 2.2 | −1.4 ± 0.5 | −1.2 ± 0.2 |
| GT$^E$/CC | −4.5 ± 2.0 | −9.7 ± 3.5 | −1.3 ± 0.3 | −1.3 ± 0.3 |
| TT$^E$/CA | −4.4 ± 1.6 | −8.3 ± 2.9 | −1.9 ± 0.4 | −1.7 ± 0.3 |
| T$^E$A/TC | −1.3 ± 1.3 | −0.3 ± 2.1 | −1.5 ± 0.3 | −1.4 ± 0.3 |
| T$^E$G/CC | 6.7 ± 1.6 | 25.0 ± 2.9 | −1.0 ± 0.4 | −1.7 ± 0.3 |
| T$^E$C/GC | −10.3 ± 1.4 | −28.5 ± 2.6 | −1.3 ± 0.4 | −1.0 ± 0.2 |
| T$^E$T/AC | −6.6 ± 1.9 | −16.3 ± 3.3 | −1.6 ± 0.3 | −1.0 ± 0.4 |
| mis-match T$^E$•G | | | | |
| AT$^E$/GT | 2.4 ± 1.0 | 9.4 ± 1.8 | −0.6 ± 0.3 | −0.7 ± 0.2 |
| CT$^E$/GG | −2.5 ± 1.4 | −3.1 ± 2.4 | −1.5 ± 0.5 | −1.5 ± 0.3 |
| GT$^E$/GC | 1.2 ± 1.3 | 6.8 ± 2.3 | −1.4 ± 0.2 | −0.8 ± 0.3 |
| TT$^E$/GA | −5.0 ± 1.6 | −11.3 ± 2.7 | −1.2 ± 0.4 | −1.5 ± 0.3 |
| T$^E$A/TG | 8.3 ± 1.1 | 29.9 ± 1.8 | −1.0 ± 0.2 | −1.6 ± 0.2 |
| T$^E$C/GG | −12.4 ± 1.3 | −35.3 ± 2.3 | −1.5 ± 0.4 | −0.9 ± 0.2 |
| T$^E$G/CG | 6.1 ± 1.6 | 22.7 ± 2.7 | −0.7 ± 0.5 | −0.8 ± 0.2 |
| T$^E$T/AG | −6.0 ± 1.3 | −15.6 ± 2.2 | −1.5 ± 0.4 | −1.1 ± 0.3 |
| mis-match T$^E$•T | | | | |
| AT$^E$/TT | 0.7 ± 1.2 | 7.1 ± 2.1 | −1.4 ± 0.3 | −1.5 ± 0.2 |
| CT$^E$/TG | −0.7 ± 1.3 | 3.6 ± 2.3 | −1.7 ± 0.3 | −1.6 ± 0.2 |

TABLE 1-continued

Parameters of nearest neighbor method used for prediction

| nearest neighbor (5' to 3'/5' to 3') | ΔΔH° [kcal mol⁻¹] | ΔΔS° [cal mol⁻¹ K⁻¹] | ΔΔG°₃₇ [kcal mol⁻¹] | ΔΔG°₆₀ [kcal mol⁻¹] |
|---|---|---|---|---|
| GT$^E$/TC | 6.5 ± 1.6 | 23.1 ± 2.8 | −0.8 ± 0.3 | −1.5 ± 0.3 |
| TT$^E$/TA | −6.7 ± 1.6 | −16.0 ± 2.8 | −2.2 ± 0.3 | −1.8 ± 0.2 |
| T$^E$A/TT | 4.3 ± 1.6 | 18.6 ± 2.8 | −1.9 ± 0.4 | −2.0 ± 0.3 |
| T$^E$C/GT | −2.9 ± 1.3 | −3.6 ± 2.3 | −1.6 ± 0.3 | −1.5 ± 0.3 |
| T$^E$G/CT | 2.6 ± 1.5 | 11.5 ± 2.7 | −1.0 ± 0.4 | −1.4 ± 0.2 |
| T$^E$T/AT | −4.2 ± 1.2 | −8.8 ± 2.1 | −1.6 ± 0.3 | −1.5 ± 0.2 |

Figure 5:
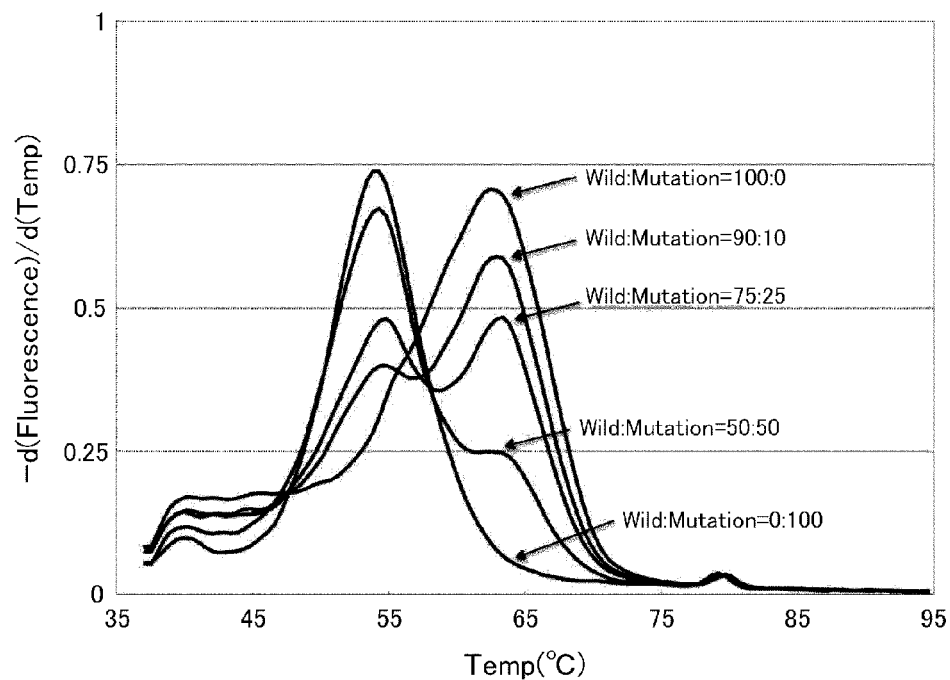
FIG. 5 shows graphs illustrating the difference in the melting curve analysis between the cases where the position of the dye differs between the same sequences in an Example.
Figure 5:
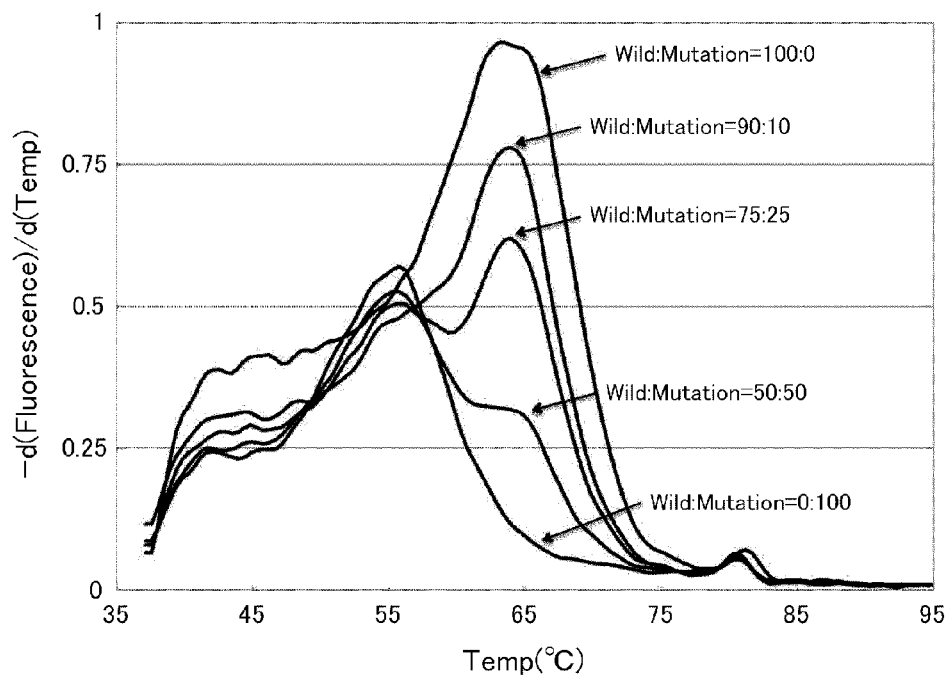

FIG. 5 shows graphs illustrating melting curve analysis in the case where the position of the dye differs between the same sequences in the above-described measurement. The upper graph shows the result obtained regarding 5'-AGCTG GTGGCGZAG-3' (SEQ ID NO: 38), and the lower graph shows the result obtained regarding 5'-AGCTG GZGGCGTAG-3' (SEQ ID NO: 39) (Z denotes the position of the dye, G denotes the position to be paired with the mutation site). In the upper graph, Z and G are at least four bases away from each other. In the lower graph, Z and G are three or fewer bases away from each other. In FIG. 5, the horizontal axis indicates the temperature (° C.), and the vertical axis indicates −dF/dT, i.e., the differential value of the fluorescence value (the numerical value obtained by differentiating the fluorescence value with respect to the temperature).

FIG. 6 shows a graph illustrating the relationship between the distance (the number of bases) between the dye and the mismatch and the height of the peak of the melting curve in the above-described measurement. In FIG. 6, the horizontal axis indicates the distance (the number of bases) between the dye and the mismatch, and the vertical axis indicates the height of the peak of the melting curve. As shown in FIG. 6, it was demonstrated that the peak was low in the case where the distance between the dye and the mismatch is two bases or less.

Example 3

The 3' end of the nucleic acid molecule (DNA oligomer 110) was chemically modified in the same manner as in Example 1 to synthesize each nucleic acid probe of the present invention (Eprobe). In the present example, it was demonstrated that, when the full-match Eprobe was added to a PCR reaction system, the Eprobe hybridized to a target region in a template sequence, whereby the clumping effect of suppressing the amplification of a sequence including this region was obtained. At that time, with a template having a mismatch to the Eprobe, the Eprobe hybridized weakly so that no clumping effect was obtained. That is, it was demonstrated that the mutant-type sequence that was present in a small amount could be detected easily by performing enrichment of the mutant-type sequence through an amplification reaction using a wild-type Eprobe.

The reaction was carried out as follows. First, PCR was carried out by a real-time PCR system "CFX96" (Bio-Rad) using a reaction reagent "AmpliTaqGold Master Mix" (Life Technologies) in a specified manner (template DNA-containing sample: 5 µl, primer solutions (10 µM): 2.5 µl each, Eprobe solution (2 µM): 2.5 µl, the total amount of reaction solution: 25 µl). The PCR conditions were as follows. An initial thermal denaturation at 95° C. for 10 minutes was conducted, and then a cycle of a thermal denaturation at 95° C. for 12 seconds, annealing at 56° C. for 30 seconds, and an extension reaction at 72° C. for 12 seconds was repeated to a total of 50 cycles. As primer sequences, 5'-TTATAAGGCCTGCTGAAAATGACTGAA-3' (SEQ ID NO: 32) and 5'-TGAATTAGCTGTATCGTCAAGGCACT-3' (SEQ ID NO: 33) were used, and as a template, plasmid DNA that encodes a Kras sequence was used. As a mutant, a Codon 12 G12D mutant was used. As an Eprobe for detection, 5'-GTZGGAGCTGGTGG-3' (SEQ ID NO: 40) was used. Z denotes dT to which dye labels that exhibit an excitonic effect had been introduced. The fluorescence intensity and the melting curves of the amplification products were analyzed using the CFX Manager Software version 1.6. The melting curve analysis was carried out with a temperature increase from 30° C. to 95° C. at 0.1° C./second. As a control, the melting curve analysis in a system in which the Eprobe was not added was carried out in the same manner as described above immediately after addition of 2.5 μl of the Eprobe solution (2 μM).

Figure 7:
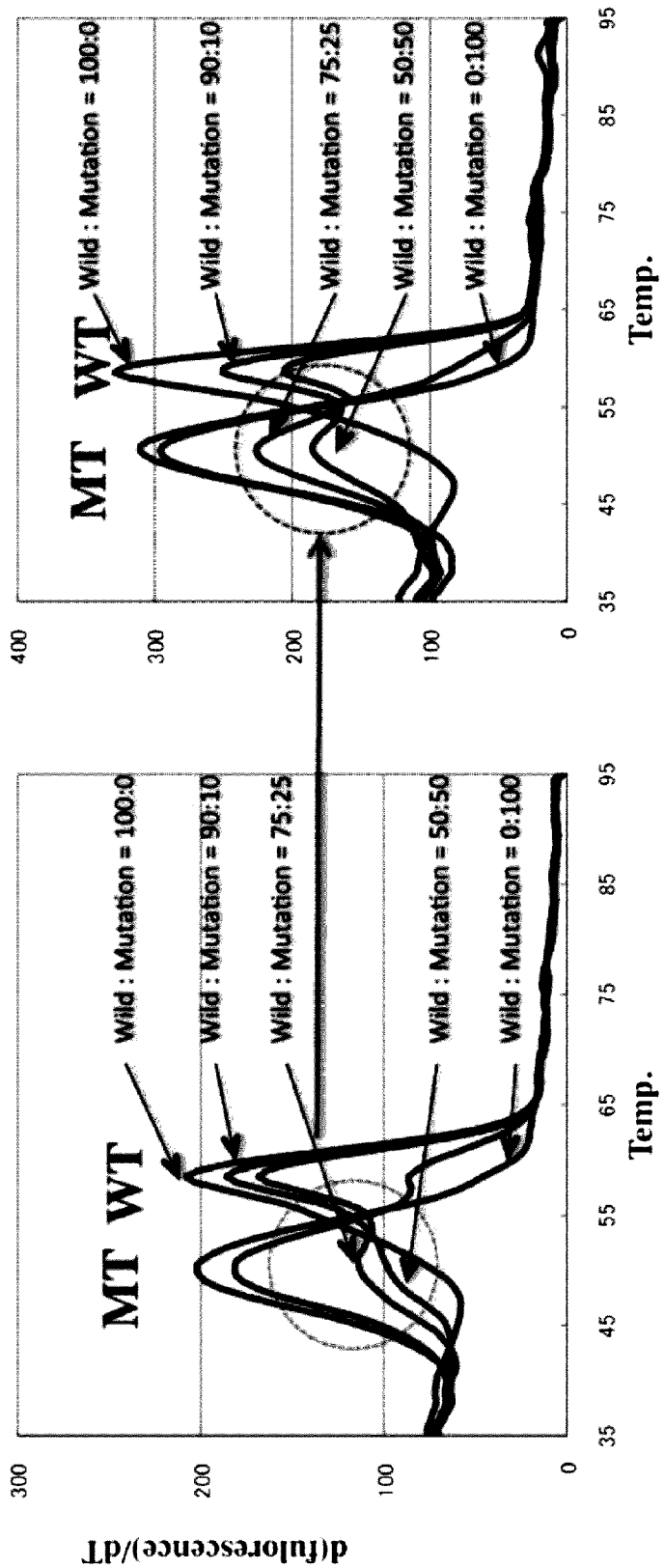
FIG. 7 shows graphs illustrating the melting curve analysis result for confirming the clumping effect in an Example.

FIG. 7 shows the melting curve analysis result for confirming the clumping effect in the above-described measurement. The right graph shows melting curves obtained when the Eprobe was added to the PCR reaction system in advance to verify the clumping effect. The left graph shows melting curves obtained when the Eprobe was added after the PCR reaction. In each of the right graph and the left graph of FIG. 7, the horizontal axis indicates the temperature (° C.), and the vertical axis indicates the value obtained by differentiating the fluorescence intensity with respect to the temperature. As shown in FIG. 7, by adding the Eprobe in advance, a peak of the mutation was obviously increased.

Example 4

The 3' end of the nucleic acid molecule (DNA oligomer 110) was chemically modified in the same manner as in Example 1 to synthesize each nucleic acid probe of the present invention (Eprobe). In the present example, as in Example 3, it was demonstrated that, when the full-match Eprobe was added to a PCR reaction system, the Eprobe hybridized to a target region in a template sequence, whereby the clumping effect of suppressing the amplification of a sequence including this region was obtained. As in Example 3, with a template having a mismatch to the Eprobe, the Eprobe hybridized weakly so that no clumping effect was obtained. Thus, the mutant-type sequence that was present in a small amount could be detected easily by performing enrichment of the mutant-type sequence through an amplification reaction using a wild-type probe. Further, in the present example, an effect obtained by designing the full-match Eprobe so that the sequence to which the primer used in the PCR method hybridizes competes with (is close to or overlaps with) the target sequence to which the full-match Eprobe hybridizes was confirmed. That is, by designing the full-match Eprobe so as to cause the above-described competition, an extension reaction from the primer hardly occur or does not at all occur, so that the effect of the enrichment by the clumping effect further can be increased.

The reaction of the present example was carried out as follows. First, PCR was carried out by a real-time PCR system "RotorGeneQ" (trade name, Qiagen) using a reaction reagent "Genotyping Master Mix" (trade name, Roche) in a specified manner (template DNA-containing sample: 5 μl, primer solutions (100 μM): 0.2 μl (Reverse) and 1 μl (Forward), Eprobe solution (2 μM): 2 μl, the total amount of reaction solution: 20 μl). The PCR conditions were as follows. An initial thermal denaturation at 95° C. for 10 minutes was conducted, and then a cycle of a thermal denaturation at 95° C. for 12 seconds, annealing at 63° C. for 15 seconds, and an extension reaction at 72° C. for 12 seconds was repeated to a total of 50 cycles. As primer sequences, 5'-TTATAAGGCCTGCTGAAAATGACTGAA-3' (SEQ ID NO: 32) and 5'-TGAATTAGCTGTATCGT-CAAGGCACT-3' (SEQ ID NO: 33) were used, and as a template, plasmid DNA that encodes a Kras sequence was used. As a mutant, a Codon 12 G12D mutant was used. As Eprobes for detection, 5'-TTGGAGCTGGTGGCGZAG-GCAA-C3-3' (SEQ ID NO: 41) (general Eprobe) and 5'-CTCZTGCCTACGCCACCAG-C3-3' (SEQ ID NO: 42) (competitive Eprobe) were used. Z denotes dT to which fluorescent dye moieties (dye labels) that exhibit an excitonic effect had been introduced. The "general Eprobe" does not compete with the primer sequence because the general Eprobe is at a position at which there is no competitive relationship with the primer sequence, and the Tm value of the general Eprobe is lower than that of the primer sequence. In contrast, the "competitive Eprobe" competes with the primer sequence because the competitive Eprobe is at a position at which there is a competitive relationship with the primer sequence, and the Tm value of the competitive Eprobe is higher than that of the primer sequence. The fluorescence intensity and high resolution melting of amplification products were analyzed using RotorGene Q Software Version: 2.0.2 (Build 4). The high resolution melting was carried out with a temperature increase from 40° C. to 95° C. at 0.5° C./4 seconds. As a control, high resolution melting analysis in a system in which the Eprobe had not been added was carried out in the same manner as described above immediately after addition of 2 μl of the Eprobe solution (2 μM).

Figure 8:
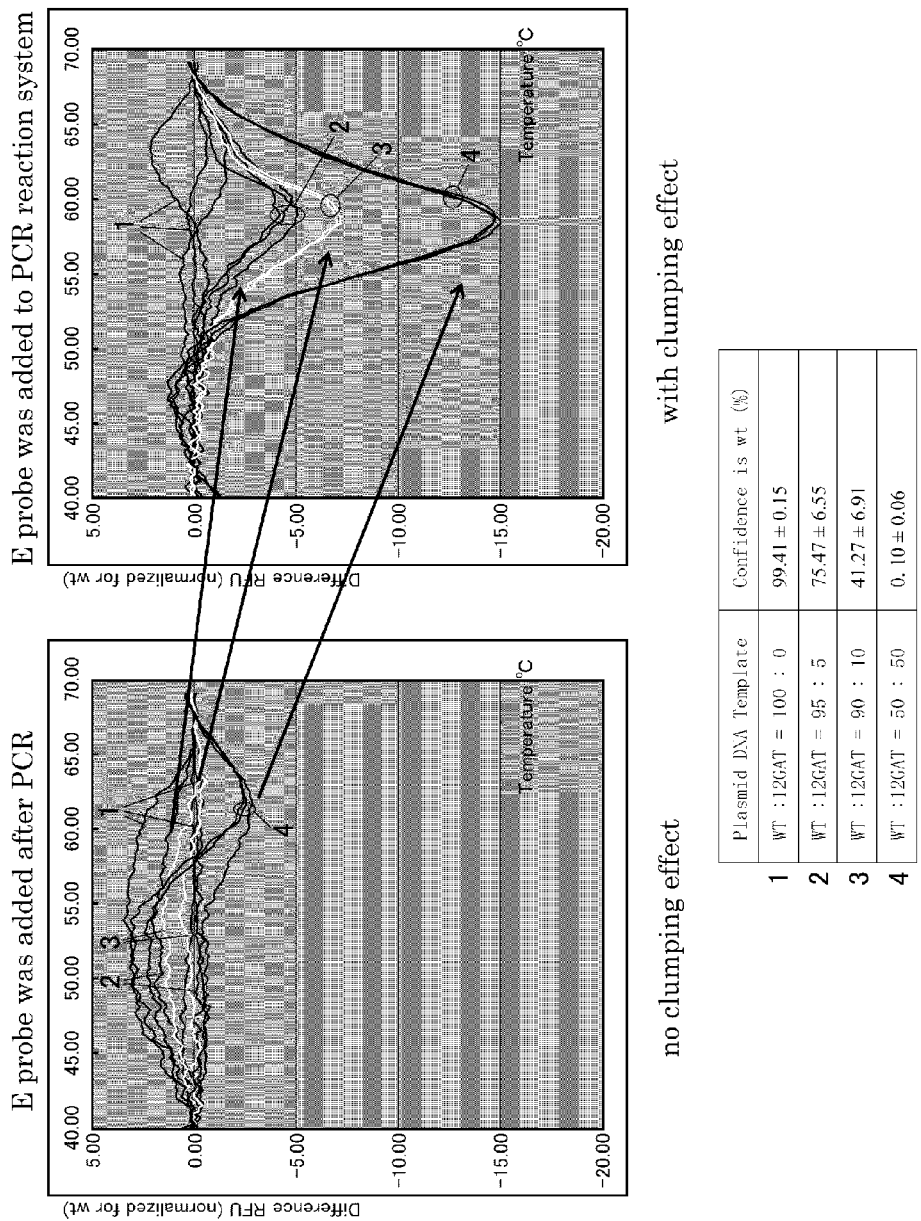
FIG. 8 shows other graphs illustrating the melting curve analysis result for confirming the clumping effect in an Example.

FIG. 8 shows graphs illustrating the results of the high resolution melting curve analysis using the general Eprobe. In FIG. 8, the left graph shows the result in the case where no Eprobe was added to the PCR reaction system and the Eprobe was added after the PCR reaction, and the right graph shows the result in the case where the Eprobe was added to the PCR reaction system. In each of the graphs, the vertical axis indicates the difference RFU of the fluorescence value, and the smaller the numerical value on the vertical axis, the greater the degree of the amplification (enrichment) of the nucleic acid sequence. In the graphs, the numeral "1" denotes the result of the reaction using templates (plasmid DNAs) with WT: 12GAT=100:0 (no mutation, 100% wild-type). The numeral "2" denotes the result of the reaction using templates (plasmid DNAs) with WT: 12GAT=95:5 (5% of Codon 12 G12D mutant). The numeral "3" denotes the result of the reaction using templates (plasmid DNAs) with WT: 12GAT=90:10 (10% of Codon 12 G12D mutant). The numeral "4" denotes the result of the reaction using templates (plasmid DNAs) with WT: 12GAT=50:50 (50% of Codon 12 G12D mutant). Each of the results denoted with the numerals "1" to "4" was obtained by performing the reaction and the analysis three times under the same conditions with respect to the same templates. In the table shown below the graphs, the "Confidence is wt (%)" means the statistical certainty of being determined as a wild-type, and when this value is small, it can be determined that the mutant is present statistically significantly. As shown in FIG. 8, from the data regarding the high resolution melting, it was really clearly demonstrated that the mutant-type nucleic acid sequence was enriched in the case where the Eprobe was added to the PCR reaction system (right graph) as compared with the case where no Eprobe was added to the PCR reaction system (left graph).

Figure 9:
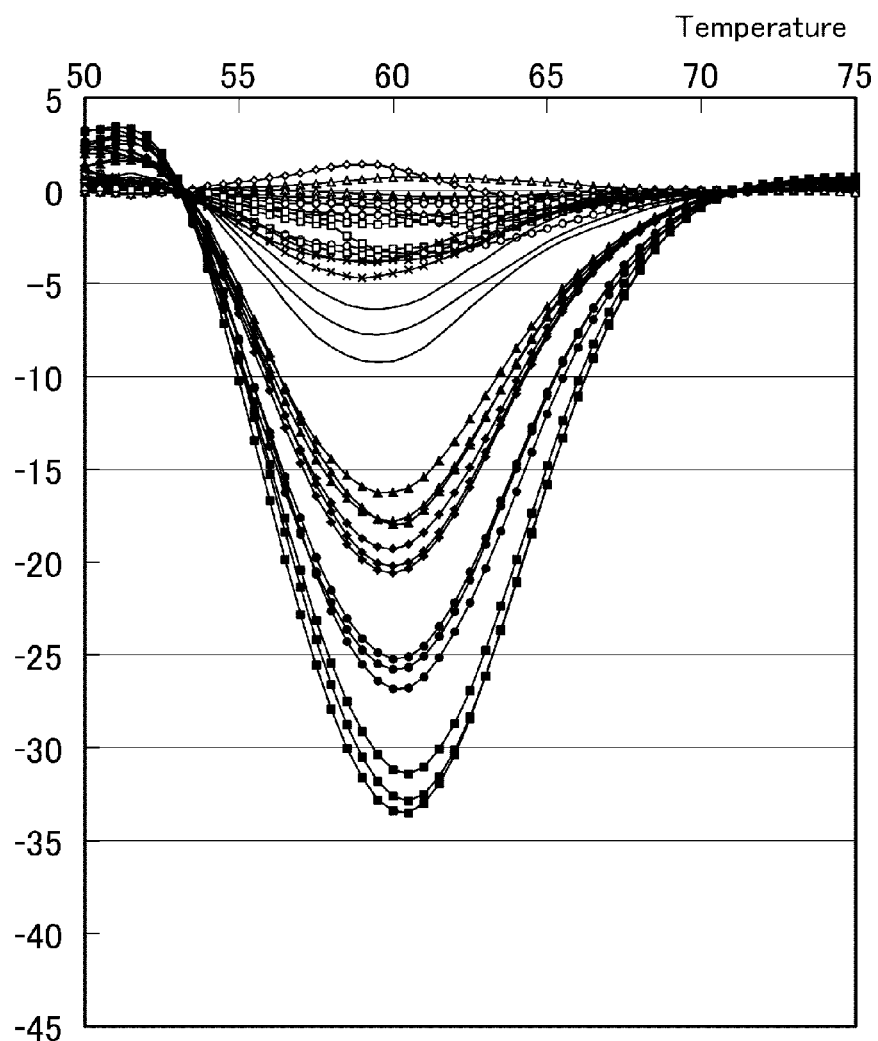
FIG. 9 shows another graph illustrating the melting curve analysis result for confirming the clumping effect in an Example.

FIG. 9 shows a graph illustrating the results of the high resolution melting analysis in the case where the competitive Eprobe was added to the PCR reaction system. In FIG. 9, the vertical axis indicates the difference RFU of the fluorescence value, and the smaller the numerical value on the vertical axis, the greater the degree of the amplification (enrichment) of the nucleic acid sequence. In the graph, curves indicated with "open triangles (Δ)" show the results (high resolution melting analysis results) of the reaction using a WT template (plasmid DNA) (no mutation, 100% wild-type). Curves indicated with "open rhombi (◇)" show the results of the reaction using templates (plasmid DNAs) with 0.05% of the Codon 12 G12D mutant. Curves indicated with "open circles (○)" show the results of the reaction using templates (plasmid DNAs) with 0.10% of the Codon 12 G12D mutant. Curves indicated with "open squares (□)" show the results of the reaction using templates (plasmid DNAs) with 0.20% of the Codon 12 G12D mutant. Curves indicated with "crosses (x)" show the results of the reaction using templates (plasmid DNAs) with 0.50% of the Codon 12 G12D mutant. Curves with no sign show the results of the reaction using templates (plasmid DNAs) with 1.00% of the Codon 12 G12D mutant. Curves indicated with "filled triangles (▲)" show the results of the reaction using templates (plasmid DNAs) with 2.50% of the Codon 12 G12D mutant. Curves indicated with "filled rhombi (◆)" show the results of the reaction using templates (plasmid DNAs) with 5% of the Codon 12 G12D mutant. Curves indicated with "filled circles (●)" show the results of the reaction using templates (plasmid DNAs) with 10% of the Codon 12 G12D mutant. Curves indicated with "filled squares (■)" show the results of the reaction using templates (plasmid DNAs) with 50% of the Codon 12 G12D mutant. With respect to the same templates, the reaction and the analysis were carried out three times under the same conditions. In the table on the lower side of the graph, the "Confidency" means the statistical certainty of being determined as a wild-type, and when this value is small, it can be determined that the mutant is present statistically significantly. As shown in FIG. 8, the competitive Eprobe caused more effective suppression of the amplification of the wild-type sequence by the competitive effect with the primer sequence, as compared with the general Eprobe.

Example 5

The 3' end of the nucleic acid molecule (DNA oligomer 110) was chemically modified in the same manner as in Example 1 to synthesize each nucleic acid probe of the present invention (Eprobe). In the present example, classification (identification) of the mutation was carried out by the wild-type Eprobe utilizing the melting curve analysis. Specifically, the Tm values of the Eprobes used in the present example are slightly different from one another depending on sequence with which the probe mismatches. It was demonstrated that, by utilizing the difference, target sequences containing a mismatch can be identified. As mentioned above, in conventional art, detection probes corresponding to respective mutations are required for classification (identification). However, it was demonstrated that, according to the Eprobe of the present invention, the classification (identification) of mutant-type base sequences can be carried out using a wild-type sequence.

The reaction of the present example was carried out as follows. First, PCR was carried out by a real-time PCR system "RotorGeneQ" (trade name, Quiagen) using a reaction reagent "Genotyping Master Mix" (trade name, Roche) in a specified manner (template DNA-containing sample: 2.5 μl, primer solutions (100 μM): 0.02 μl (Reverse) and 0.1 μl (Forward), Eprobe solution (4 μM): 1 μl, the total amount of reaction solution: 10 μl). The PCR conditions were as follows. An initial thermal denaturation at 95° C. for 10 minutes was conducted, and then a cycle of a thermal denaturation at 95° C. for 12 seconds, annealing at 63° C. for 15 seconds, and an extension reaction at 72° C. for 12 seconds was repeated for a total of 50 cycles. As primer sequences, 5'-TTATAAGGCCTGCTGAAAATGACTGAA-3' (SEQ ID NO: 32) and 5'-TGAATTAGCTGTATCGT-CAAGGCACT-3' (SEQ ID NO: 33) were used, and as a template, plasmid DNA that encodes a Kras sequence was used. As mutants, a G12S mutant having a mutation in codon 12 (hereinafter referred to as "Codon 12 G12S mutant") and a G13D mutant were used. As an Eprobe for detection, 5'-CTCZTGCCTACGCCACCAG-C3-3' (SEQ ID NO: 42) (competitive Eprobe) was used. Z denotes dT to which dye labels that exhibit an excitonic effect had been introduced. The fluorescence intensity and high resolution melting of amplification products were analyzed using RotorGene Q Software Version: 2.0.2 (Build 4). The high resolution melting was carried out with a temperature increase from 40° C. to 95° C. at 0.5° C./4 seconds.

Figure 10:
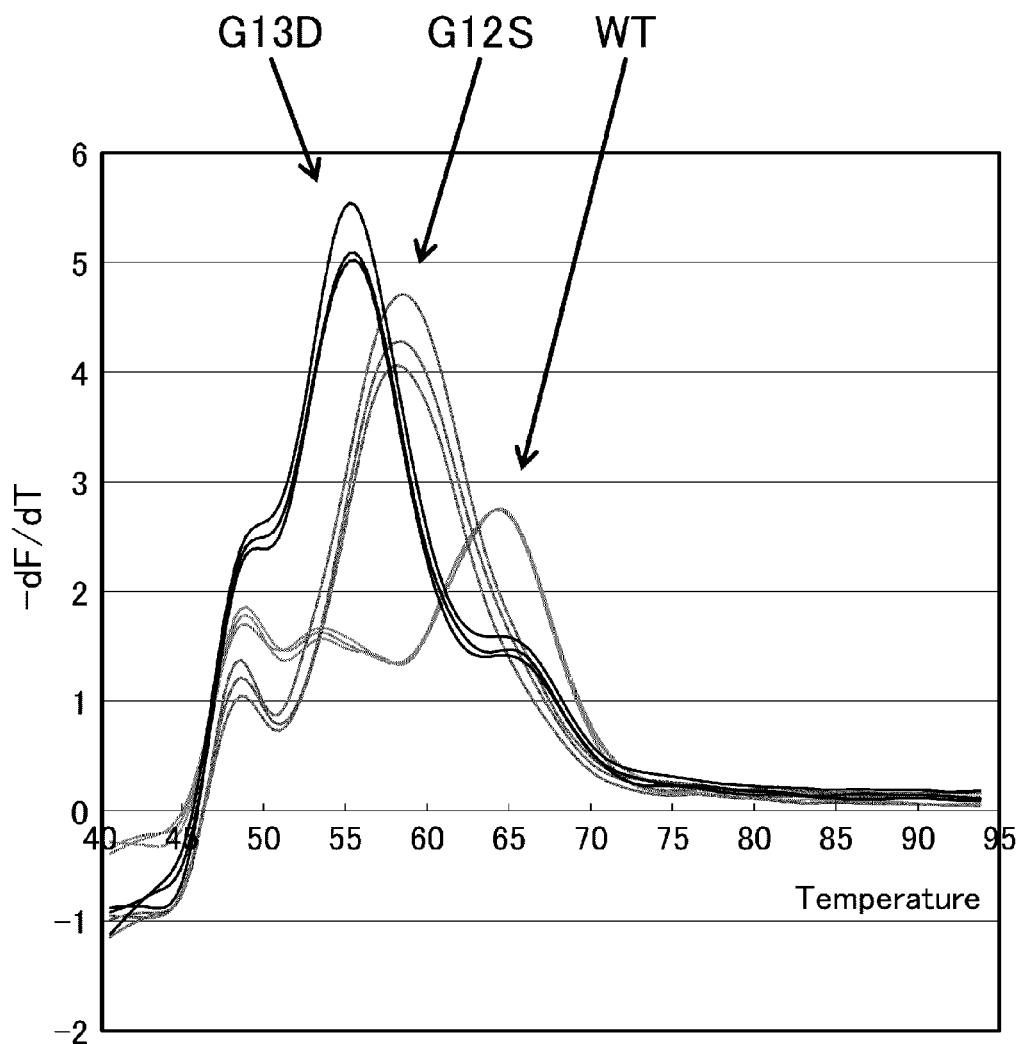
FIG. 10 shows a graph illustrating the type classification (identification) of a mutant-type nucleic acid by the wild-type Eprobe in an Example.

The measurement results are shown in the graph of FIG. 10. In FIG. 10, the horizontal axis indicates the temperature (° C.), and the vertical axis indicates −dF/dT, i.e., the differential value of the fluorescence value (the numerical value obtained by differentiating the fluorescence value with respect to the temperature). With respect to the same templates, the reaction and the analysis were carried out three times under the same conditions. In the present example, as shown in FIG. 10, G12S (Tm: 57.5° C.) and G13D (Tm: 54.8° C.) could be classified (identified) clearly using the wild-type Eprobe on the basis of the difference in Tm value as compared with the wild-type Eprobe owing to the respective mismatches.

Example 6

In the present example, a target sequence contained in a double-stranded nucleic acid was detected using a nucleic acid probe of the present invention (Eprobe).

First, an Eprobe (HCV_1b.Cf.188-13.E6) having a sequence of 5'-TCTTGGAZCAACC-3' (SEQ ID NO: 43) was synthesized using an automated DNA synthesizer under the same condition as in an ordinary phosphoramidite method (Z denotes dT to which dye labels that exhibit an excitonic effect had been introduced). As a template DNA sense strand ((sense) DNA), HCV_1b.Of.209-48 (SEQ ID NO: 44) was used, and as a template DNA antisense strand ((anti-sense) DNA) having a sequence complementary thereto, HCV_1b.Or.162-48 (SEQ ID NO: 45) was used. In SEQ ID NO: 44 ((anti-sense) DNA) below, the underlined portion denotes a target sequence complementary to the nucleic acid sequence of the Eprobe (SEQ ID NO: 43). In SEQ ID NO: 45 ((sense) DNA) below, the underlined portion denotes a sequence (the same sequence as the Eprobe) complementary to the target sequence.

```
                                              (SEQ ID NO: 44)
5'-ACGACCGGGTCCTTTCTTGGATCAACCCGCTCAATGCCTGGAGATTT
G-3'

(SEQ ID NO: 45)
5'-CAAATCTCCAGGCATTGAGCGGGTTGATCCAAGAAAGGACCCGGTCG
T-3'
```

0.5 μM of the Eprobe (SEQ ID NO: 43), 0.5 μM of the (sense) DNA (SEQ ID NO: 44), and 0.5 μM of the (anti-sense) DNA (SEQ ID NO: 45) were dissolved in a buffer (50 mM KCl, 1.5 mM MgCl$_2$, 10 mM Tris-HCl, pH 8.3). Thus, a measurement sample was obtained. This measurement sample was heated to 95° C. and kept at this temperature for 1 minute, and then cooled to the room temperature. Thereafter, emitted light at 530 nm was measured using excitation light at 510 nm while keeping the sample at 25° C. for 30 seconds and then heating it from 25° C. to 95° C. The differential values of the obtained fluorescence values with respect to the temperature were taken, and each melting curve was analyzed. The fluorescence intensity and the melting curves of the nucleic acid triple strand were analyzed using Agilent Technologies Mx3000. As a control, a sample containing no template nucleic acid and containing only the Eprobe was subjected to the melting curve analysis in the same manner as described above.

The results of the melting curve analysis are shown in the graph of FIG. 11. In FIG. 11, the horizontal axis indicates the temperature (° C.), and the vertical axis indicates –dF/dT, i.e., the differential value of the fluorescence value (the numerical value obtained by differentiating the fluorescence value with respect to the temperature). In FIG. 11, plots on the upper side (filled circles (●)) show the results of the melting cure analysis regarding the sample containing the template DNA double strand and the Eprobe. Plots on the lower side (filled squares (■)) show the results of the melting curve analysis regarding the sample containing only the Eprobe and not containing the template nucleic acid. With respect to the same sample, the reaction and the analysis were carried out three times under the same conditions. As can be seen from the plots on the upper side of FIG. 11 (template DNA double strand+Eprobe), the Eprobe exhibited strong fluorescence even when the template nucleic acid was a double strand. In contrast, in the plots on the lower side (only Eprobe), fluorescence was not at all exhibited. That is, it was demonstrated that the Eprobe of the present invention can detect a target sequence with high sensitivity even when a template nucleic acid is a double strand.

Example 7

In the present example, it was demonstrated that the nucleic acid probe of the present invention (Eprobe) may exhibit fluorescence even when a labeled base to which fluorescent dye moieties that exhibit an excitonic effect (dyes) are bound does not hybridize to a target sequence.

First, an Eprobe (TE_TM_25P.Of.1-25.E23) having a sequence of 5'-TTZCCTACCCACTTTTCTCCCATTT-3' (SEQ ID NO: 46) was synthesized using an automated DNA synthesizer under the same conditions as in an ordinary phosphoramidite method (Z denotes dT to which dye labels that exhibit an excitonic effect had been introduced). As a template nucleic acid (complementary strand DNA having a sequence complementary to a partial sequence of the Eprobe), TE_ext_25P.Or.1-15 (SEQ ID NO: 47) having a sequence of 5'-AAATGGGAGAAAAGT-3' was used. The base sequence of the template nucleic acid (15 bases) was complementary to 15 bases on the 3'-end side of the Eprobe. In the Eprobe, Z (dT to which dye labels that exhibit an excitonic effect had been introduced) was 8 bases away from the sequence complementary to the template nucleic acid.

1.0 μM of the Eprobe (SEQ ID NO: 46) and 1.0 μM of the template nucleic acid (SEQ ID NO: 47) were dissolved in a buffer (1.4 mM dNTP, 20 mM Tris-HCl, 10 mM $(NH_4)_2SO_4$, 8 mM $MgSO_4$, 0.1% Tween-20, 10 mM KCl). Thus, a measurement sample was obtained. The melting curve analysis was carried out as follows using a CFX96 (Bio-Rad Laboratories). More specifically, first, emitted light at 530 nm was measured using excitation light at 510 nm while heating the measurement sample from 4° C. to 95° C. After the measurement, the differential values of the obtained fluorescence values with respect to the temperature were taken, and each melting curve was analyzed. In this reaction, an extension reaction of DNA did not occur because no DNA polymerase was used in the reaction. On this account, the 3' end of each Eprobe used in these experiments was not chemically modified with a phosphate group or a C3 linker OH group. Also in the case where Eprobes with their 3' ends being chemically modified with a phosphate group or a C3 linker OH group were used, the same results were obtained. A sample obtained in the same manner as described above except that only the Eprobe (SEQ ID NO: 46) was dissolved in the buffer without adding the template nucleic acid (SEQ ID NO: 47) was subjected to melting curve analysis in the same manner as described above.

Figure 12:
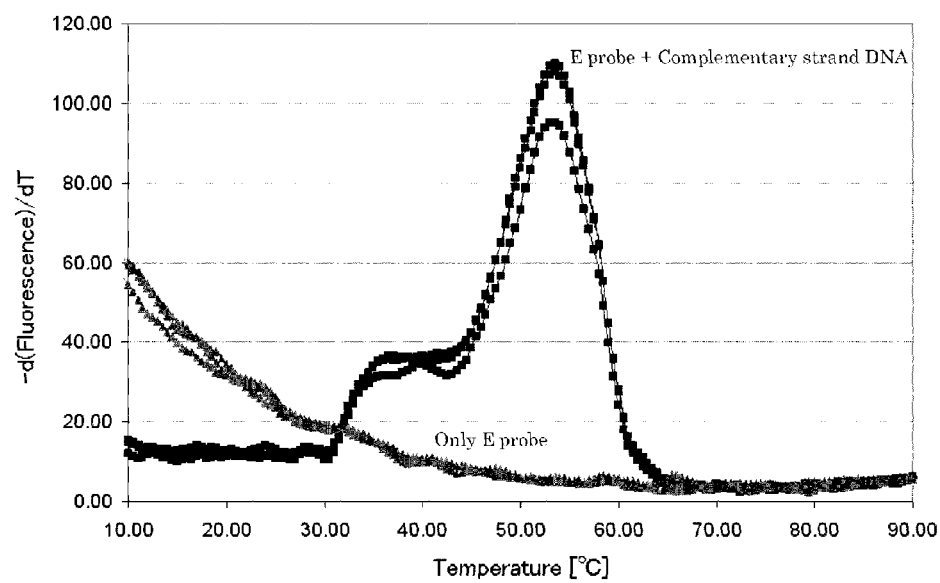
FIG. 12 shows a graph illustrating the fluorescence emission by the secondary structure formation in an Example.

The results of the melting curve analysis are shown in the graph of FIG. 12. In FIG. 12, the horizontal axis indicates the temperature (° C.), and the vertical axis indicates –dF/dT, i.e., the differential value of the fluorescence value (the numerical value obtained by differentiating the fluorescence value with respect to the temperature). Curves indicated with "filled squares (■)" show the analysis results regarding the sample containing the Eprobe (SEQ ID NO: 46) and the template nucleic acid (complementary strand DNA, SEQ ID NO: 47). Curves indicated with "filled triangles (▲)" show the analysis results regarding the sample containing only the Eprobe (SEQ ID NO: 46) and containing no template nucleic acid (SEQ ID NO: 47). With respect to the same sample, the reaction and the analysis were carried out three times under the same conditions. As can be seen from the curves indicated with "filled squares (■)", it was found that, even if the Eprobe has the base labeled with the fluorescent dye moieties (dyes) at a position not hybridizing to the target sequence, the Eprobe may exhibit strong fluorescence and a high Tm value may be obtained. Although the mechanism thereof is unknown, it is speculated to be as follows, for example: the base sequence that forms the Eprobe folds back (U-turns), whereby the labeled base and the fluorescent dye moieties (dyes) approach the double strand formed by hybridization between the Eprobe and the target sequence, and the fluorescent dye moieties then enter the double strand to emit fluorescence. In contrast, as can be seen from the curves indicated with "filled triangles (▲)", in the case of the sample containing no template nucleic acid of SEQ ID NO: 47 (containing only the Eprobe of SEQ ID NO: 46), undesirable fluorescence that might be confused with the fluorescence derived from the template nucleic acid was not observed. By utilizing this phenomenon, even with respect to a target sequence for which it is usually difficult to design a corresponding probe, the detection of fluorescence becomes possible with a simple probe design by placing the labeled base at a position corresponding to the outside of the target sequence (a position not included in the sequence that hybridizes to the target sequence).

SEQUENCE LISTING

TF13024WO sequence list 2013.07.10_ST25.txt

The invention claimed is:

1. A method for producing a nucleic acid probe comprising artificially synthesizing a nucleic acid molecule that is configured to detect a target sequence that has a mutation, wherein the nucleic acid probe is synthesized by a phosphoramidite method so that:

the nucleic acid molecule comprises a plurality of fluorescent dye moieties that exhibit an excitonic effect;

at least two of the fluorescent dye moieties that exhibit an excitonic effect are bound to the same base or two adjacent bases in the nucleic acid molecule with each fluorescent dye moiety being bound via a linker (a linking atom or a linking atomic group);

an extension-side end of the nucleic acid molecule is chemically modified, thereby preventing an extension reaction of the nucleic acid molecule; and the nucleic acid probe satisfies the following conditions (1) and (2) and also satisfies the following condition (3) or (4):

(1) a labeled base to which the fluorescent dye moieties that exhibit an excitonic effect are bound is a base other than the first base at each end of the nucleic acid probe;

(2) the target sequence to which the nucleic acid probe hybridizes is a sequence that has a mutation, and the mutation is a base other than the first to second bases from each end of the target sequence;

(3) the labeled base is at a position at least four bases away from a base to be paired with the mutation so that a detection peak fluorescence intensity of a sequence that has the mutation in the target sequence is not lower than a detection peak fluorescence intensity of a sequence that does not have the mutation in the target sequence, with the detection peak fluorescence intensities of both the sequences being measured under the same conditions; and (4) the labeled base is at a position three or fewer bases away from the base to be paired with the mutation, so that a detection peak fluorescence intensity of a sequence that has the mutation in the target sequence is lower than a detection peak fluorescence intensity of a sequence that does not have the mutation in the target sequence, with the detection peak fluorescence intensities of both the sequences being measured under the same conditions.

2. The method according to claim 1, wherein
an extension-side end of the nucleic acid molecule is composed of an atomic group having a deoxyribose skeleton, or a ribose skeleton, and the extension-side end is chemically modified by substituting a hydrogen atom of a 3' end hydroxyl group (OH) in the atomic group with a substituent.

3. The method according to claim 2, wherein
the substituent with which the hydrogen atom of the 3' end hydroxyl group (OH) is substituted is any one of the following (A) to (C):

(A) a substituent represented by the following chemical formula (1001):

$$*\text{-}L^{1000}\text{-}X \qquad (1001)$$

where in the chemical formula (1001),

X is a hydroxyl group (OH), an amino group ($NH_2$), or a group obtained by substitution of at least one hydrogen atom thereof with a substituent, $L^{1000}$ is a linear or branched alkylene group with a carbon number of 1 to 20, and the mark "*" indicates a position at which the substituent is bound to the oxygen atom of the 3' end hydroxyl group (OH);

(B) a dideoxynucleotide group that does not have a 3' end OH (hydroxyl group) and thus prevents an extension reaction caused by polymerase; and (C) a thiophosphoric acid diester group.

4. The method according to claim 1, wherein
the nucleic acid molecule comprises at least one of structures represented by the following formulae (16), (16b), (17), and (17b):

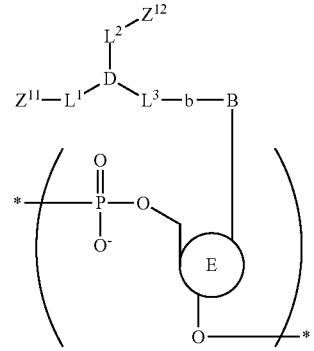

(16)

-continued (16b)
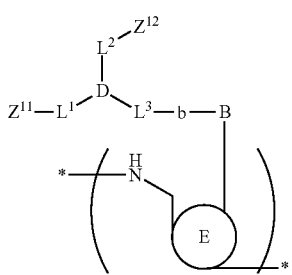

(17)
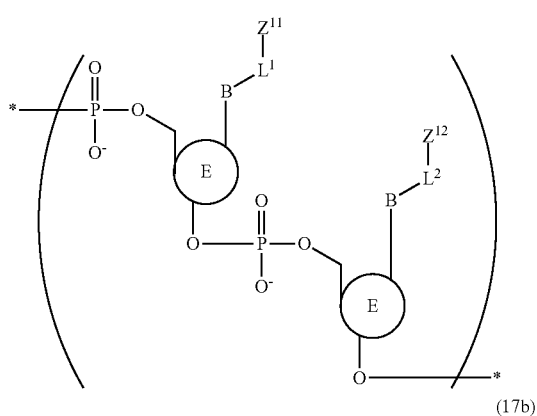

(17b)
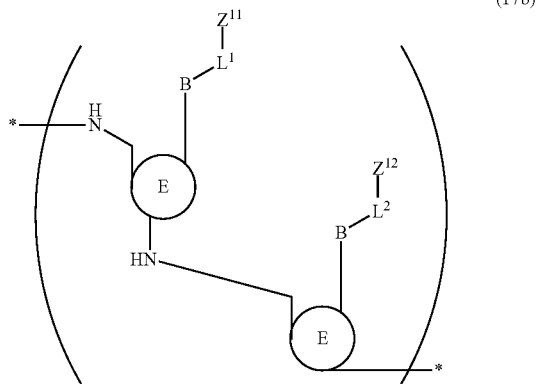

where in the formulae (16), (16b), (17), and (17b),
B is an atomic group having a natural nucleobase (adenine, guanine, cytosine, thymine, or uracil) skeleton or an artificial nucleobase skeleton,
E is:
(i) an atomic group having a deoxyribose skeleton, or a ribose skeleton, or
(ii) an atomic group having a peptide structure or a peptoid structure,
$Z^{11}$ and $Z^{12}$ are each a fluorescent dye moiety that exhibits an excitonic effect, and may be identical to or different from each other,
$L^1$, $L^2$, and $L^3$ are each a linker (a linking atom or a linking atomic group), the main chain length (the number of main chain atoms) thereof is arbitrary, $L^1$, $L^2$, and $L^3$ each may or may not contain each of C, N, O, S, P, and Si in the main chain, $L^1$, $L^2$, and $L^3$ each may or may not contain each of a single bond, a double bond, a triple bond, an amide bond, an ester bond, a disulfide bond, an imino group, an ether bond, a thioether bond, and a thioester bond in the main chain, and $L^1$, $L^2$, and $L^3$ may be identical to or different from each other,
D is CR, N, P, P=O, B, or SiR where R is a hydrogen atom or an alkyl group, and b is a single bond, a double bond, or a triple bond, or alternatively,
in the formulae (16) and (16b), $L^1$ and $L^2$ are each a linker, $L^3$, D, and b may not be present, and $L^1$ and $L^2$ may be bonded directly to B, provided that:
in the formulae (16) and (17), E is an atomic group described in the item (i), and at least one O atom in a phosphoric acid linkage may be substituted with an S atom;
in the formulae (16b) and (17b), E is an atomic group described in the item (ii); and
in the formulae (17) and (17b), the respective Bs may be identical to or different from each other, and the respective Es may be identical to or different from each other.
5. The method according to claim 4, wherein,
in the formulae (16), (17), (16b), and (17b), the main chain length (the number of main chain atoms) of each of $L^1$, $L^2$, and $L^3$ is an integer of 2 or more.
6. The method according to claim 4, wherein
in the formulae (16), (17), (16b), and (17b),
$Z^{11}$ and $Z^{12}$ are each independently any one of thiazole orange, oxazole yellow, cyanine, hemicyanine, cyanine dyes, methyl red, azo dyes, and biotin.
7. The method according to claim 4, wherein
$Z^{11}$ and $Z^{12}$ are each independently an atomic group represented by any one of the following formulae (7) to (9):

(7)
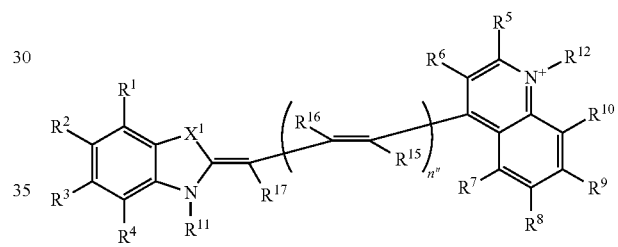

(8)
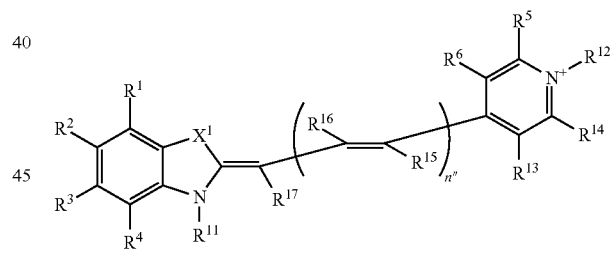

(9)
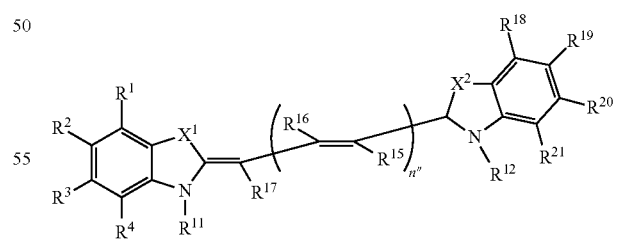

where in the formulae (7) to (9),
$X^1$ and $X^2$ are S, O, or Se,
n″ is 0 or a positive integer,
$R^1$ to $R^{10}$ and $R^{13}$ to $R^{21}$ are each independently a hydrogen atom, a halogen atom, a lower alkyl group, a lower alkoxyl group, a nitro group, or an amino group,
one of $R^{11}$ and $R^{12}$ is a linking group that is bound to $L^1$ or $L^2$ in the formulae (16), (17), (16b), and (17b), and the other is a hydrogen atom or a lower alkyl group, when a plurality of $R^{15}$s are present in the formula (7), (8), or (9), they may be identical to or different from each other, when a plurality of $R^{16}$s are present in the formula (7), (8), or (9), they may be identical to or different from each other, and $X^1$, $X^2$, and $R^1$ to $R^{21}$ in $Z^{11}$ and $X^1$, $X^2$, and $R^1$ to $R^{21}$ in $Z^{12}$ may be identical to or different from each other, respectively.

8. The method according to claim 7, wherein in the formulae (7) to (9), in $R^1$ to $R^{21}$, the lower alkyl group is a linear or branched alkyl group with a carbon number of 1 to 6, and the lower alkoxyl group is a linear or branched alkoxyl group with a carbon number of 1 to 6.

9. The method according to claim 7, wherein in the formulae (7) to (9), in $R^{11}$ and $R^{12}$, the linking group is a polymethylene carbonyl group with a carbon number of 2 or more and is bound to $L^1$ or $L^2$ in the formulae (16), (16b), (17), and (17b) in a carbonyl group moiety.

10. The method according to claim 7, wherein $Z^{11}$ and $Z^{12}$ are each independently an atomic group represented by the formula (7) or (8), and $Z^{11}$ and $Z^{12}$ represented by the formula (7) or (8) is a group represented by the following formula (19) or (20):

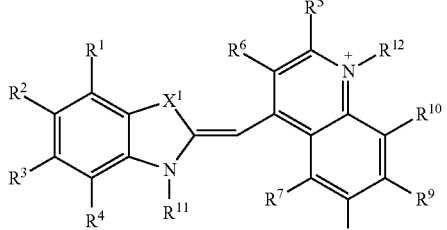

(19)

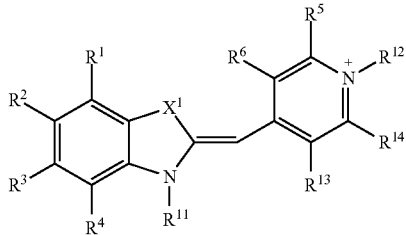

(20)

where in the formulae (19) and (20), $X^1$, $R^1$ to $R^{10}$, $R^{13}$ and $R^{14}$, and $R^{11}$ and $R^{12}$ are identical to those in the formulae (7) to (9).

11. The method according to claim 10, wherein $Z^{11}$ and $Z^{12}$ are each independently an atomic group represented by the above formula (19), where in the formula (19), $X^1$ is S, $R^1$ to $R^{10}$ are hydrogen atoms, and one of $R^{11}$ and $R^{12}$ is a linking group that is bound to $L^1$ or $L^2$ in the formulae (16), (17), (16b), and (17b), and the other is a methyl group.

12. The method according to claim 10, wherein $Z^{11}$ and $Z^{12}$ are each independently an atomic group represented by the above formula (19), where in the formula (19), $X^1$ is S, $R^1$, $R^4$, $R^5$, $R^6$, $R^7$, $R^9$, and $R^{10}$ are hydrogen atoms, $R^2$, $R^3$, and $R^{12}$ are methyl groups, $R^8$ is a halogen atom, and $R^{11}$ is a linking group that is bound to $L^1$ or $L^2$ in the formulae (16), (17), (16b), and (17b).

13. The method according to claim 7, wherein $Z^{11}$ and $Z^{12}$ are each independently an atomic group represented by the above formula (7), where in the formula (7), $X^1$ is S, n″ is 1, $R^1$ to $R^{10}$, $R^{15}$, $R^{16}$, and $R^{17}$ are hydrogen atoms, $R^{11}$ is a linking group that is bound to $L^1$ or $L^2$ in the formulae (16), (17), (16b), and (17b), and $R^{12}$ is a methyl group.

14. The method according to claim 7, wherein $Z^{11}$ and $Z^{12}$ are each independently an atomic group represented by any one of the following formulae:

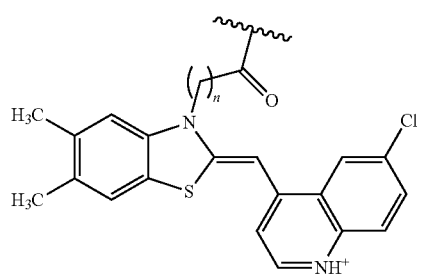

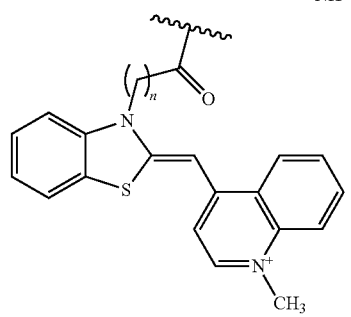

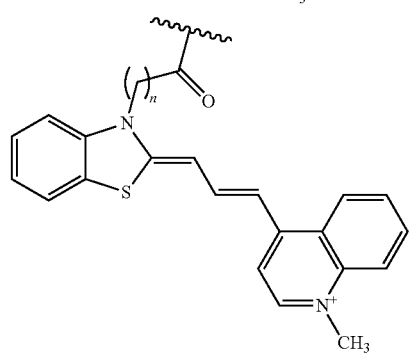

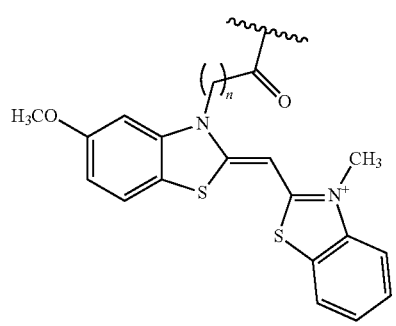

-continued

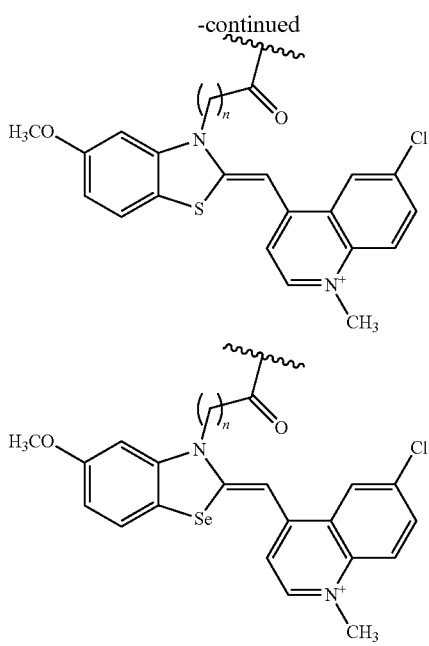

where in each of the above chemical formula,
n is a positive integer.

15. The method according to claim 14, wherein
the linker length n is in the range from 2 to 6.

16. The method according to claim 4, wherein
in the formulae (16), (17), (16b), and (17b),
B is an atomic group having a natural nucleobase (adenine, guanine, cytosine, thymine, or uracil) skeleton.

17. The method according to claim 4, wherein
in the formulae (16), (17), (16b), and (17b),
B is an atomic group having an artificial nucleobase skeleton, and the artificial nucleobase is 2-amino-6-(N, N-dimethylamino)purine pyridin-2-one, 5-methylpyridin-2-one, 2-amino-6-(2-thienyl)purine, pyrrole-2-carbaldehyde, 9-methylimidazo[(4,5)-b]pyridine, 5-iodo-2-oxo(1H)pyridine 2-oxo-(1H)pyridine, 2-amino-6-(2-thiazolyl)purine, 7-(2-thienyl)-imidazo[4,5-b]pyridine, bromothymine, azaadenine, or azaguanine.

18. The method according to claim 4, wherein
in the formulae (16), (17), (16b), and (17b),
B is an atomic group having an artificial nucleobase skeleton, and the artificial nucleobase is Py, Py der., Pu, or Pu der.,
the Py is an atomic group having a covalent bond to E in the 1-position and a covalent bond to a linker moiety in the 5-position in a six-membered ring represented by the following formula (11):

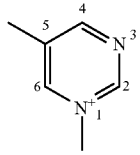

(11)

the Py der. is an atomic group in which at least one of all the atoms of the six-membered ring of the Py has been substituted with an N, C, S, or O atom,
the Pu is an atomic group having a covalent bond to E in the 9-position and a covalent bond to a linker moiety in the 8-position in a condensed ring represented by the following formula (12):

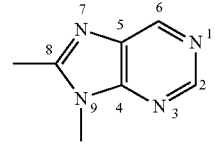

(12)

and the Pu der. is an atomic group in which at least one of all the atoms of a five-membered ring of the Pu has been substituted with an N, C, S, or O atom.

19. The method according to claim 4, wherein
the structure represented by the formula (16) is a structure represented by the following formula (16-1) or (16-2),
the structure represented by the formula (16b) is a structure represented by the following formula (16b-1) or (16b-2),
the structure represented by the formula (17) is a structure represented by the following formula (17-1), and
the structure represented by the formula (17b) is a structure represented by the following formula (17b-1):

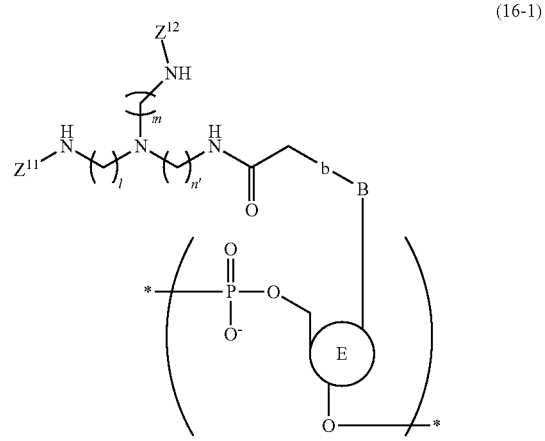

(16-1)

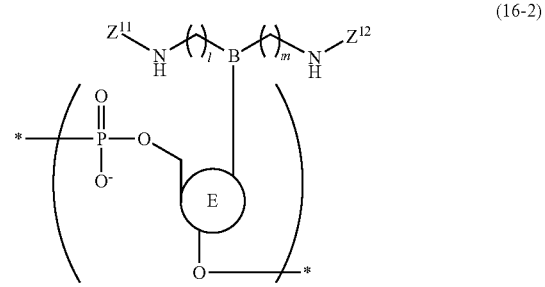

(16-2)

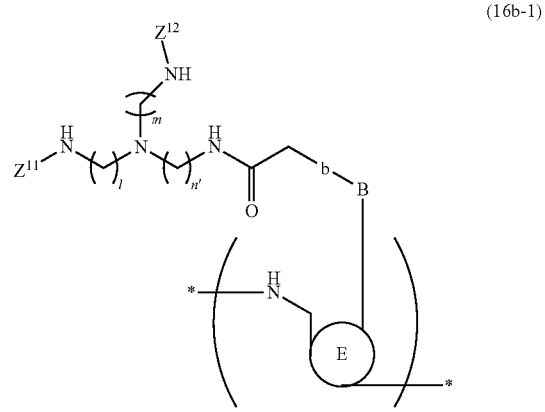

(16b-1)

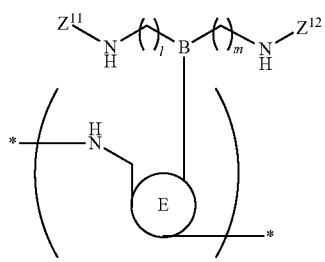
(16b-2)

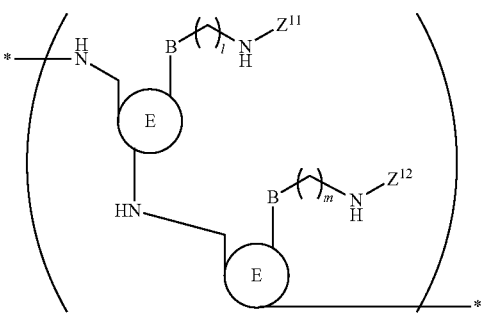
(17b-1)

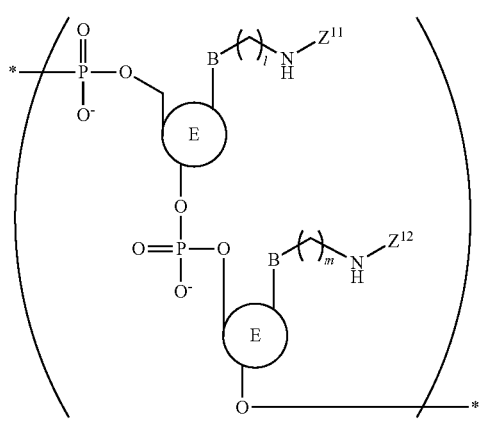
(17-1)

where in the formulae (16-1), (16-2), (16b-1), (16b-2), (17-1), and (17b-1), l, m and n' are positive integers, l, m and n' may be identical to or different from each other, l, m and n' each may or may not contain each of C, N, O, S, P, and Si in a main chain thereof, and l, m and n' each may or may not contain each of a single bond, a double bond, a triple bond, an amide bond, an ester bond, a disulfide bond, an imino group, an ether bond, a thioether bond, and a thioester bond in the main chain, B, E, $Z^{11}$, $Z^{12}$, and b are identical to those in the formulae (16), (16b), (17), and (17b), and in the formulae (16-1), (16-2), and (17-1), at least one O atom in a phosphoric acid linkage may be substituted with an S atom.

20. The method according to claim 19, wherein
in the formulae (16-1), (16-2), (16b-1), (16b-2), (17-1), and (17b-1), l, m, and n are each an integer of 2 or more.

21. The method according to claim 4, wherein the nucleic acid probe comprises at least one of nucleotide structures represented by the following chemical formulae 106, 110, 113, 117, 120, 122, 123, 124, and 114-2, geometric isomers and stereoisomers thereof, and salts thereof:

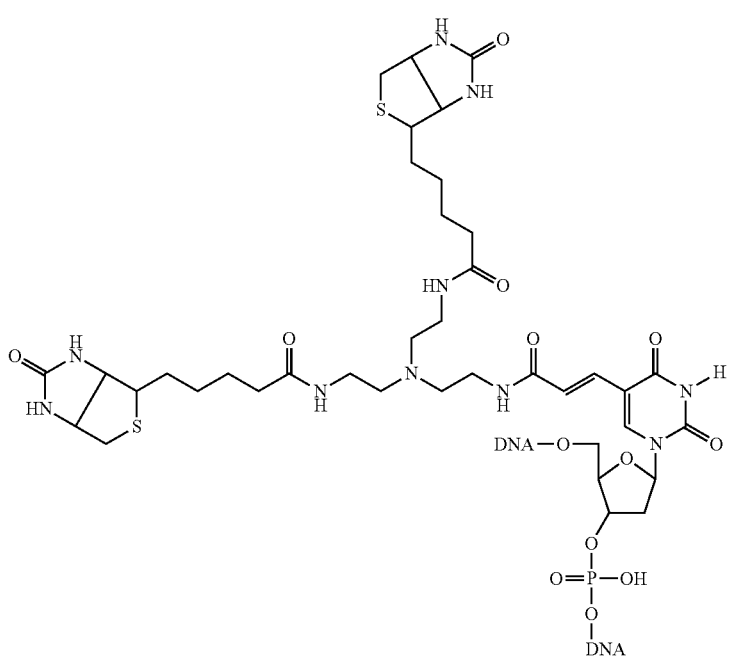

106

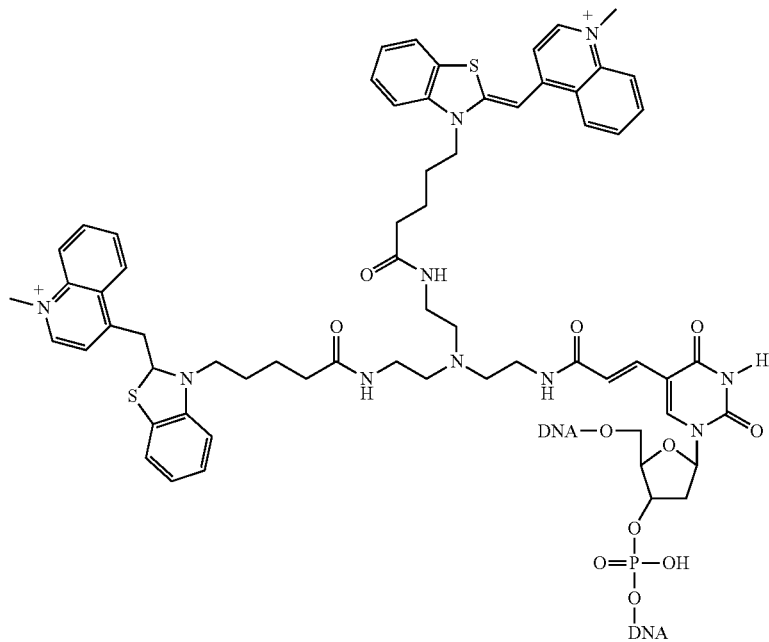
110
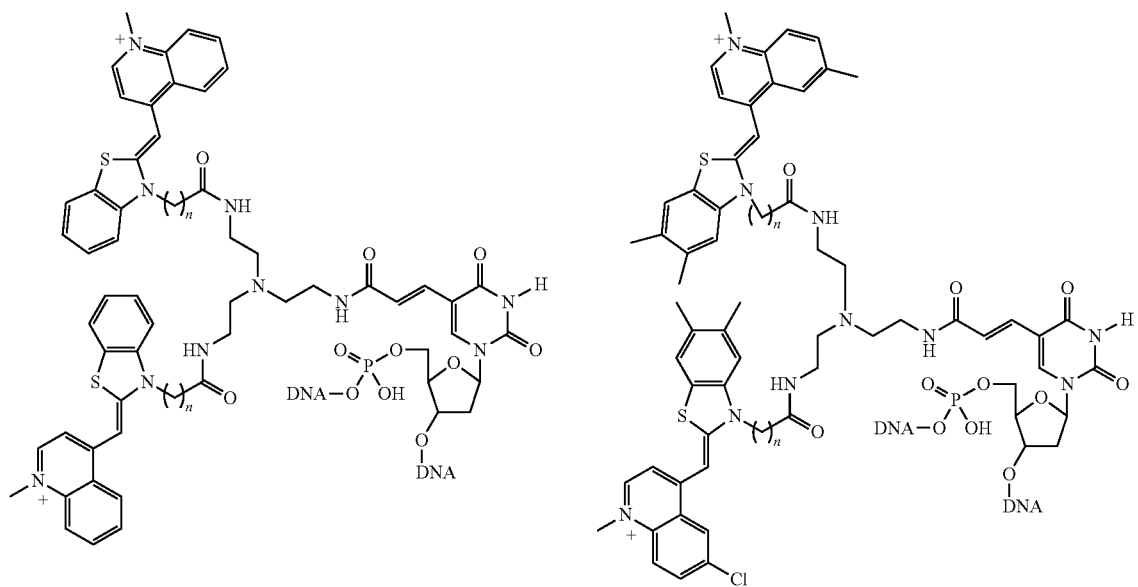
113
117

-continued
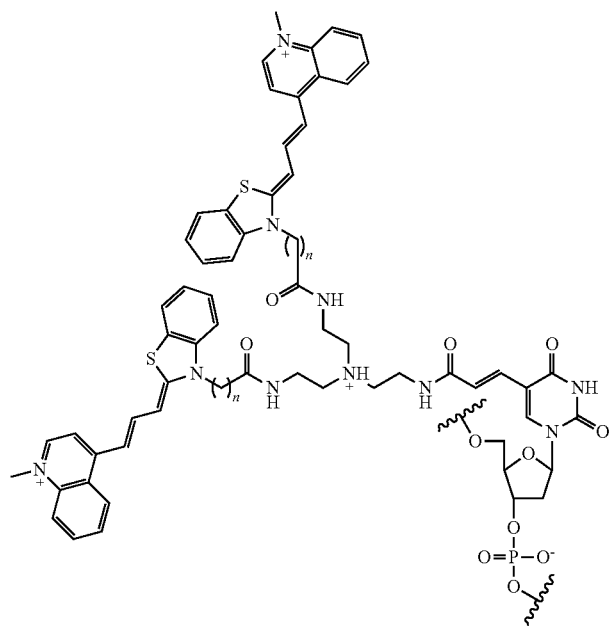
(120)
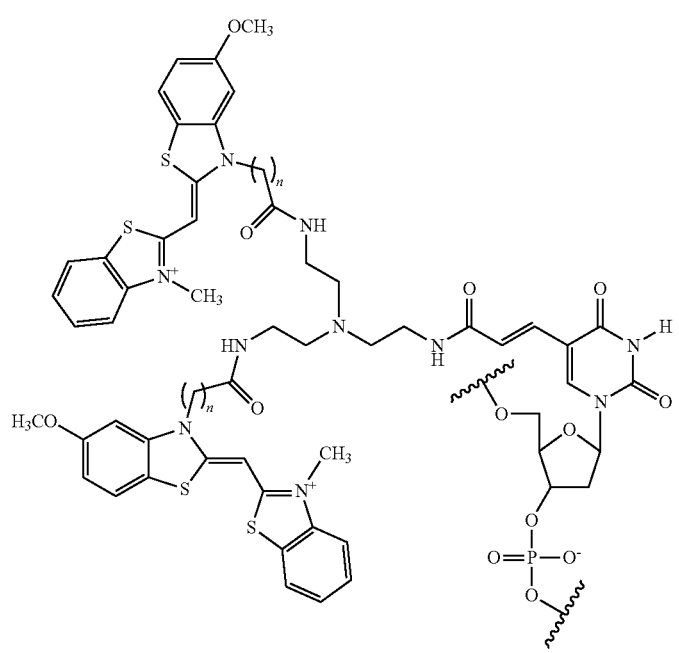
(122)

(123)
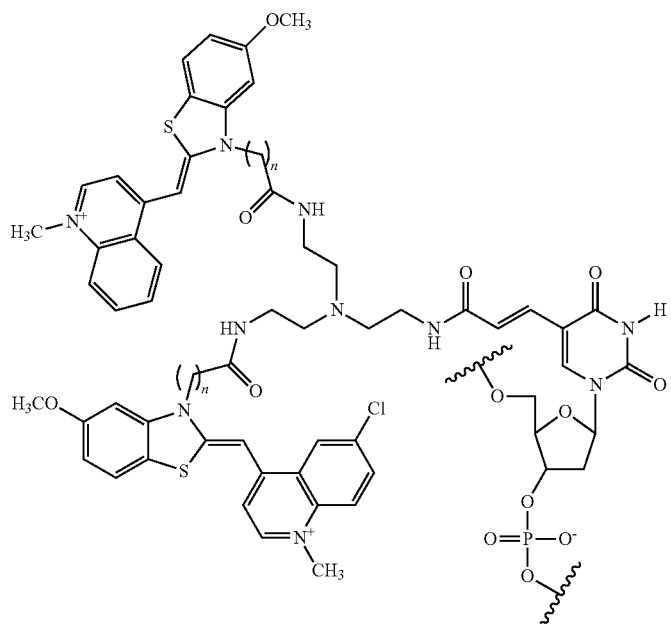
(124)
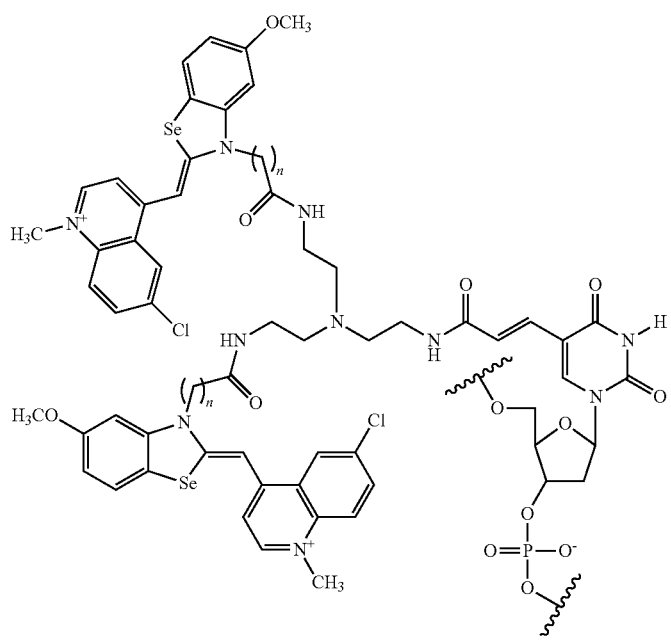

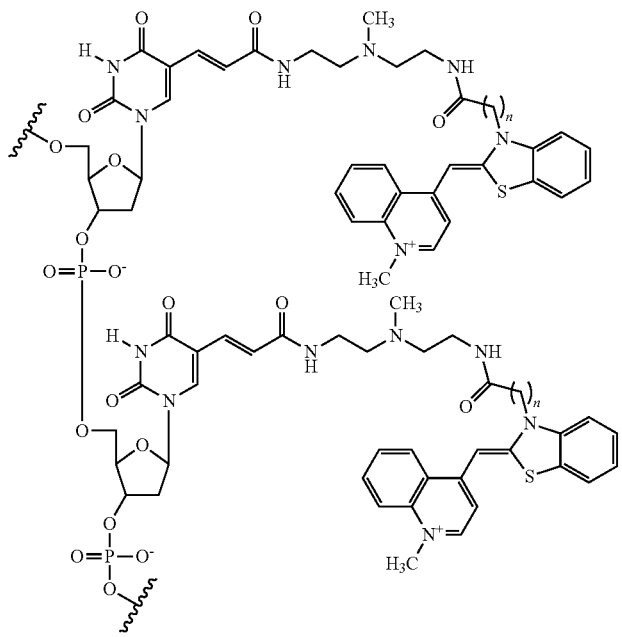

(114-2)

where in the chemical formulae 106, 110, 113, 117, 120, 122, 123, 124, and 114-2,
n is a positive integer.

22. The method according to claim 1, wherein the nucleic acid probe is provided so that a region composed of a labeled base to which the fluorescent dye moieties that exhibit an excitonic effect are bound, two bases immediately upstream from the labeled base, and two bases immediately downstream from the labeled base does not self-hybridize to any other region in the nucleic acid probe.

23. The method according claim 1, wherein
the nucleic acid probe is for use in detection of a target sequence in a nucleic acid, and
in the method for producing the nucleic acid probe, the nucleic acid probe is provided so that the nucleic acid probe comprises a sequence that hybridizes to the target sequence and a sequence that does not hybridize to the target sequence, and
a labeled base to which the fluorescent dye moieties that exhibit an excitonic effect are bound is included in the sequence that does not hybridize to the target sequence.

24. A method comprising detecting a target sequence in a nucleic acid by hybridizing a nucleic acid probe to the target sequence, wherein
the nucleic acid probe is a nucleic acid probe produced by the method according to claim 1.

25. The method according to claim 24, wherein the target sequence comprises a mutation.

26. The method according to claim 25, comprising:
a nucleic acid amplification step of amplifying the target sequence in a nucleic acid amplification reaction by a PCR method,
wherein the nucleic acid probe is provided so that, in the nucleic acid amplification step, the nucleic acid probe in a reaction system fully matches with the target sequence.

27. The method according to claim 26, wherein
in the nucleic acid comprising the target sequence, there is at least one base overlap between a sequence to which a primer used in the PCR method hybridizes and the target sequence.

28. The method according to claim 26, wherein
in the nucleic acid comprising the target sequence, the number of bases present between a sequence to which a primer used in the PCR method hybridizes and the target sequence is 7 or less.

29. The method according to claim 24, wherein
the target sequence comprises a plurality of mutations.

30. The method according to claim 24, wherein
the nucleic acid comprising the target sequence is a double-stranded nucleic acid.

* * * * *